US012648999B2

United States Patent
(12) United States Patent

Doppalapudi et al.

(10) Patent No.: US 12,648,999 B2

(45) **Date of Patent: *Jun. 9, 2026**

(54) COMPOSITIONS AND METHODS OF TREATING MUSCLE DYSTROPHY

(71) Applicant: Avidity Biosciences, Inc., San Diego, CA (US)

(72) Inventors: Venkata Ramana Doppalapudi, San Diego, CA (US); Michael David Hood, San Diego, CA (US); Rob Burke, Carlsbad, CA (US); Michael Caramian Cochran, Palo Alto, CA (US); Beatrice Diana Darimont, San Diego, CA (US); Yunyu Shi, La Jolla, CA (US); Gulin Erdogan Marelius, Encinitas, CA (US); Barbora Malecova, San Diego, CA (US)

(73) Assignee: Avidity Biosciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/263,325

(22) Filed: Jul. 8, 2025

(65) Prior Publication Data

US 2025/0381285 A1 Dec. 18, 2025

Related U.S. Application Data

(63) Continuation of application No. 18/326,903, filed on May 31, 2023, now Pat. No. 12,427,202, which is a continuation of application No. 17/818,319, filed on Aug. 8, 2022, now Pat. No. 11,707,532, which is a continuation of application No. 17/214,525, filed on Mar. 26, 2021, now Pat. No. 11,446,387.

(60) Provisional application No. 63/001,211, filed on Mar. 27, 2020.

(51) Int. Cl.

*A61K 47/68* (2017.01)

*C12N 15/113* (2010.01)

(52) U.S. Cl.

CPC ...... *A61K 47/6807* (2017.08); *A61K 47/6849* (2017.08); *C12N 15/1137* (2013.01); *C12N 2310/14* (2013.01); *C12N 2310/315* (2013.01); *C12N 2310/321* (2013.01); *C12N 2310/322* (2013.01); *C12N 2310/3513* (2013.01)

(58) Field of Classification Search

None

See application file for complete search history.

(56) References Cited

U.S. PATENT DOCUMENTS 5,142,047 A 8/1992 Summerton et al.
5,334,711 A 8/1994 Sproat et al.
5,627,053 A 5/1997 Usman et al.
5,716,824 A 2/1998 Beigelman et al.
5,736,557 A 4/1998 Hofheinz et al.
5,889,136 A 3/1999 Scaringe et al.
5,898,031 A 4/1999 Crooke
6,008,400 A 12/1999 Scaringe et al.
6,111,086 A 8/2000 Scaringe
6,821,783 B1 11/2004 Comely et al.
6,884,869 B2 4/2005 Senter et al.
7,244,724 B2 7/2007 Liu et al.
7,250,496 B2 7/2007 Bentwich
7,276,497 B2 10/2007 Chari et al.
7,452,987 B2 11/2008 Giese et al.
7,498,298 B2 3/2009 Doronina et al.
7,528,126 B2 5/2009 Howard et al.
7,612,062 B2 11/2009 Gregson et al.
7,659,241 B2 2/2010 Senter et al.
7,691,997 B2 4/2010 Khvorova et al.
7,709,226 B2 5/2010 Foote
7,750,116 B1 7/2010 Doronina et al.
7,833,992 B2 11/2010 Vargeese et al.
7,850,975 B2 12/2010 Mullis
7,893,245 B2 2/2011 Giese et al.
7,923,547 B2 4/2011 McSwiggen et al.
7,943,762 B2 5/2011 Weller et al.
7,964,566 B2 6/2011 Doronina et al.
8,084,598 B1 12/2011 Bentwich
8,090,542 B2 1/2012 Khvorova et al.
8,163,736 B2 4/2012 Gauzy et al.
8,202,979 B2 6/2012 Mcswiggen et al.
8,273,866 B2 9/2012 McSwiggen et al.
8,288,352 B2 10/2012 Doronina et al.
8,324,370 B2 12/2012 Giese et al.
8,404,678 B2 3/2013 Bouchard et al.
8,426,402 B2 4/2013 Li et al.
8,501,934 B2 8/2013 Howard et al.

(Continued)

FOREIGN PATENT DOCUMENTS

CA 2123307 A1 6/1993
EP 1579015 A2 9/2005

(Continued)

OTHER PUBLICATIONS

Aartsma-Rus et al. Guidelines for antisense oligonucleotide design and insight into splice-modulating mechanisms. Mol Ther 17(3):548-53 (2009).

(Continued)

*Primary Examiner* — Phuong Huynh

(74) *Attorney, Agent, or Firm* — Finnegan, Henderson, Farabow, Garrett & Dunner, LLP

(57) ABSTRACT

Disclosed herein are polynucleic acid molecules, pharmaceutical compositions, and methods for treating muscle dystrophy (DM1).

18 Claims, 5 Drawing Sheets

Specification includes a Sequence Listing.

(56) References Cited

U.S. PATENT DOCUMENTS

| | | | | |
|---|---|---|---|---|
| 8,580,820 | B2 | 11/2013 | Zanda et al. | |
| 8,604,184 | B2 | 12/2013 | Mullis et al. | |
| 8,609,105 | B2 | 12/2013 | Senter et al. | |
| 8,618,277 | B2 | 12/2013 | Beigelman et al. | |
| 8,648,185 | B2 | 2/2014 | McSwigen et al. | |
| 8,697,688 | B2 | 4/2014 | Howard et al. | |
| 8,703,714 | B2 | 4/2014 | Doronina et al. | |
| 8,802,667 | B2 | 8/2014 | Li et al. | |
| 8,835,402 | B2 | 9/2014 | Kole et al. | |
| 8,871,720 | B2 | 10/2014 | Doronina et al. | |
| 8,933,215 | B2 | 1/2015 | Giese et al. | |
| 8,936,910 | B2 | 1/2015 | Mitsch et al. | |
| 8,980,833 | B2 | 3/2015 | Richter | |
| 9,089,614 | B2 | 7/2015 | Lin et al. | |
| 9,181,551 | B2 | 11/2015 | McSwiggen et al. | |
| 9,222,092 | B2 | 12/2015 | Giese et al. | |
| 9,242,013 | B2 | 1/2016 | Howard et al. | |
| 9,260,471 | B2 | 2/2016 | Cancilla et al. | |
| 9,605,019 | B2 | 3/2017 | Verdine et al. | |
| 9,657,294 | B2 | 5/2017 | Beigelman et al. | |
| 9,695,211 | B2 | 7/2017 | Wada et al. | |
| 9,695,423 | B2 | 7/2017 | Giese et al. | |
| 9,732,344 | B2 | 8/2017 | Beigelman et al. | |
| 9,765,338 | B2 | 9/2017 | Bennett et al. | |
| 9,771,588 | B2 | 9/2017 | McSwiggen et al. | |
| 9,796,974 | B2 | 10/2017 | Rajeev et al. | |
| 9,890,379 | B2 | 2/2018 | De Kimpe et al. | |
| 9,982,257 | B2 | 5/2018 | Butler et al. | |
| 10,000,754 | B2 | 6/2018 | Beigelman et al. | |
| 10,087,210 | B2 | 10/2018 | Prakash et al. | |
| 10,323,089 | B2 | 6/2019 | Dengl et al. | |
| 10,612,027 | B2 | 4/2020 | Maier et al. | |
| 10,881,743 | B2 | 1/2021 | Geall et al. | |
| 10,913,800 | B2 * | 2/2021 | Darimont | C07K 16/2881 |
| 10,994,020 | B2 | 5/2021 | Levin et al. | |
| 11,028,179 | B2 | 6/2021 | Darimont et al. | |
| 11,179,472 | B2 | 11/2021 | Levin et al. | |
| 11,246,941 | B2 | 2/2022 | Geall et al. | |
| 11,253,607 | B2 | 2/2022 | Geall et al. | |
| 11,427,838 | B2 | 8/2022 | Lundberg et al. | |
| 11,446,387 | B2 * | 9/2022 | Doppalapudi | C07K 16/2881 |
| 11,497,814 | B2 | 11/2022 | Geall et al. | |
| 11,504,391 | B1 | 11/2022 | Schlegel et al. | |
| 11,554,176 | B2 | 1/2023 | Geall et al. | |
| 11,576,980 | B2 | 2/2023 | Geall et al. | |
| 11,583,591 | B2 | 2/2023 | Geall et al. | |
| 11,707,532 | B2 * | 7/2023 | Doppalapudi | C12N 15/1137 424/178.1 |
| 11,712,478 | B2 | 8/2023 | Geall et al. | |
| 11,834,510 | B2 | 12/2023 | Darimont et al. | |
| 11,872,287 | B2 | 1/2024 | Geall et al. | |
| 12,263,224 | B2 | 4/2025 | Geall et al. | |
| 12,370,264 | B1 | 7/2025 | Subramanian et al. | |
| 12,427,202 | B2 * | 9/2025 | Doppalapudi | C07K 16/28 |
| 2004/0224893 | A1 | 11/2004 | Wang et al. | |
| 2008/0038257 | A1 | 2/2008 | Han et al. | |
| 2008/0097092 | A1 | 4/2008 | Khvorova et al. | |
| 2008/0160030 | A1 | 7/2008 | Banchereau et al. | |
| 2009/0092985 | A1 | 4/2009 | Cardozo et al. | |
| 2009/0227655 | A1 | 9/2009 | Khan | |
| 2011/0081362 | A1 | 4/2011 | Elledge et al. | |
| 2012/0065169 | A1 | 3/2012 | Hanson et al. | |
| 2012/0094299 | A1 | 4/2012 | Ranum et al. | |
| 2013/0028919 | A1 | 1/2013 | Howard et al. | |
| 2013/0029900 | A1 | 1/2013 | Widdison | |
| 2013/0217638 | A1 | 8/2013 | Wessjohann et al. | |
| 2013/0224228 | A1 | 8/2013 | Jackson et al. | |
| 2013/0237585 | A1 * | 9/2013 | Bennett | A61P 21/00 536/24.5 |
| 2013/0309256 | A1 | 11/2013 | Lyon et al. | |
| 2013/0323268 | A1 | 12/2013 | Chari et al. | |
| 2014/0127239 | A1 | 5/2014 | Howard | |
| 2014/0194610 | A1 | 7/2014 | Verdine et al. | |
| 2014/0286970 | A1 | 9/2014 | Jeffrey et al. | |
| 2014/0294851 | A1 | 10/2014 | Nguyen | |
| 2014/0294868 | A1 | 10/2014 | Howard et al. | |
| 2014/0296321 | A1 | 10/2014 | Iversen | |
| 2014/0363454 | A1 | 12/2014 | Jackson et al. | |
| 2015/0037360 | A1 | 2/2015 | Smith | |
| 2015/0064181 | A1 | 3/2015 | Armstrong | |
| 2015/0105539 | A1 | 4/2015 | Miao et al. | |
| 2015/0105540 | A1 | 4/2015 | Miao et al. | |
| 2015/0110791 | A1 | 4/2015 | Zhang et al. | |
| 2015/0211006 | A1 | 7/2015 | Butler et al. | |
| 2016/0193355 | A1 | 7/2016 | Qin et al. | |
| 2016/0304877 | A1 | 10/2016 | Swayze et al. | |
| 2017/0281795 | A1 | 10/2017 | Geall et al. | |
| 2017/0342416 | A1 | 11/2017 | McSwiggen et al. | |
| 2018/0112214 | A1 | 4/2018 | De Kimpe et al. | |
| 2018/0127758 | A1 | 5/2018 | Bennett | |
| 2018/0163209 | A1 | 6/2018 | Bennett et al. | |
| 2018/0305689 | A1 | 10/2018 | Sætrom et al. | |
| 2018/0344817 | A1 | 12/2018 | Smith et al. | |
| 2019/0083662 | A1 | 3/2019 | Burak et al. | |
| 2019/0240346 | A1 | 8/2019 | Sugo et al. | |
| 2019/0298847 | A1 | 10/2019 | Geall et al. | |
| 2021/0228730 | A1 | 7/2021 | Subramanian et al. | |
| 2021/0299266 | A1 | 9/2021 | Doppalapudi et al. | |
| 2022/0008550 | A1 | 1/2022 | Geall et al. | |
| 2022/0040323 | A1 | 2/2022 | Geall et al. | |
| 2022/0062434 | A1 | 3/2022 | Geall et al. | |
| 2022/0096647 | A1 | 3/2022 | Geall et al. | |
| 2022/0133900 | A1 | 5/2022 | Geall et al. | |
| 2022/0409735 | A1 | 12/2022 | Doppalapudi et al. | |
| 2023/0047754 | A1 | 2/2023 | Geall et al. | |
| 2023/0201362 | A1 | 6/2023 | Geall et al. | |
| 2023/0201363 | A1 | 6/2023 | Geall et al. | |
| 2023/0398231 | A1 | 12/2023 | Doppalapudi et al. | |
| 2024/0132611 | A1 | 4/2024 | Darimont et al. | |
| 2025/0195676 | A1 | 6/2025 | Geall et al. | |
| 2025/0381286 | A1 | 12/2025 | Levin et al. | |

FOREIGN PATENT DOCUMENTS

| | | | |
|---|---|---|---|
| EP | 2049664 | B1 | 9/2011 |
| EP | 2278004 | B1 | 10/2012 |
| EP | 1423406 | B2 | 11/2015 |
| EP | 3031920 | A1 | 6/2016 |
| EP | 2287306 | B2 | 10/2016 |
| EP | 3030658 | A4 | 3/2017 |
| EP | 2287305 | B2 | 11/2017 |
| EP | 2902406 | B1 | 1/2018 |
| EP | 2595664 | B1 | 10/2018 |
| EP | 3644416 | A2 | 4/2020 |
| JP | 2002095476 | A | 4/2002 |
| KR | 20140026045 | A | 3/2014 |
| WO | WO-9104753 | A1 | 4/1991 |
| WO | WO-9207065 | A1 | 4/1992 |
| WO | WO-9315187 | A1 | 8/1993 |
| WO | WO-9726270 | A2 | 7/1997 |
| WO | WO-9734631 | A1 | 9/1997 |
| WO | WO-9813526 | A1 | 4/1998 |
| WO | WO-0050008 | A2 | 8/2000 |
| WO | WO-0149698 | A1 | 7/2001 |
| WO | WO-2004009851 | A2 | 1/2004 |
| WO | WO-2006006948 | A2 | 1/2006 |
| WO | WO-2008036127 | A2 | 3/2008 |
| WO | WO-2009099942 | A2 | 8/2009 |
| WO | WO-2009099991 | A2 | 8/2009 |
| WO | WO-2009126933 | A2 | 10/2009 |
| WO | WO-2011150408 | A2 | 12/2011 |
| WO | WO-2012012443 | A2 | 1/2012 |
| WO | WO-2012125850 | A1 | 9/2012 |
| WO | WO-2013138662 | A1 | 9/2013 |
| WO | WO-2013166155 | A1 | 11/2013 |
| WO | WO-2014080251 | A1 | 5/2014 |
| WO | WO-2014140317 | A2 | 9/2014 |
| WO | WO-2014145090 | A1 | 9/2014 |
| WO | WO-2014177042 | A1 | 11/2014 |
| WO | WO-2014189973 | A2 | 11/2014 |
| WO | WO-2014197854 | A1 | 12/2014 |
| WO | WO-2015021457 | A2 | 2/2015 |
| WO | WO-2015038426 | A1 | 3/2015 |
| WO | WO-2015057699 | A2 | 4/2015 |

(56) References Cited

FOREIGN PATENT DOCUMENTS

| | | | |
|---|---|---|---|
| WO | WO-2015069587 | A2 | 5/2015 |
| WO | WO-2015107425 | A2 | 7/2015 |
| WO | WO-2016081643 | A1 | 5/2016 |
| WO | WO-2016207240 | A1 | 12/2016 |
| WO | WO-2018002812 | A1 | 1/2018 |
| WO | WO-2018078131 | A1 | 5/2018 |
| WO | WO-2018078134 | A1 | 5/2018 |
| WO | WO-2018129384 | A1 | 7/2018 |
| WO | WO-2018142322 | A1 | 8/2018 |
| WO | WO-2019060775 | A1 | 3/2019 |
| WO | WO-2019071028 | A1 | 4/2019 |
| WO | WO-2019113393 | A1 | 6/2019 |
| WO | WO-2020028861 | A1 | 2/2020 |
| WO | WO-2020132584 | A1 | 6/2020 |
| WO | WO-2021195469 | A1 | 9/2021 |

OTHER PUBLICATIONS

Aartsma-Rus et al. Progress in therapeutic antisense applications for neuromuscular disorders. Eur J Hum Genet 18(2):146-153 (2010).

Abramova, T. et al., Novel oligonucleotide analogues based on morpholino nucleoside subunits antisense technologies: New chemical possibilities. Indian Journal of Chemistry 48B:1721-1726 (2009).

Agarwal, Paresh et al. A Pictet-Spengler Ligation for Protein Chemical Modification. PNAS USA 110(1):46-51 (2013).

Albarran, Brian et al. Efficient intracellular delivery of a proapoptotic peptide with a pH-responsive carrier. Reactive and Functional Polymers 71(3):261-265 (2011).

Alegre, Maria-Luisa et al. Effect of a Single Amino Acid Mutation on the Activating and Immunosuppressive Properties of a “Humanized” OKT3 Monoclonal Antibody. Journal of Immunology 148(11):3461-3468 (1992).

Al-Lazikani, Bissan et al. Standard Conformations for the Canonical Structures of Immunoglobulins. Journal of Molecular Biology 273(4):927-948 (1997).

Almagro, Juan C. et al. Humanization of Antibodies. Frontiers in Bioscience. A Journal and Virtual Library 13:1619-1633 (2008).

Axup, Jun Y. et al. Synthesis of Site-specific Antibody-drug Conjugates Using Unnatural Amino Acids. PNAS USA 109(40):16101-16106 (2012).

Ballangrud et al. Response of LNCaP Spheroids After Treatment With an Alpha-Particle Emitter (213Bi)-labeled Anti-Prostate-Specific Membrane Antigen Antibody (J591) Cancer Res. 61:2008-2014 (2001).

Beduneau et al. Design of targeted lipid nanocapsules by conjugation of whole antibodies and antibody Fab' fragments. Biomaterials 28(33):4978-4990 (2007).

Beigelman, Leonid et al. Chemical Modification of Hammerhead Ribozymes: Catalytic Activity and Nuclease Resistance. Journal of Biological Chemistry 270(43):25702-25708 (1995).

Bird, Robert E. et al. Single-chain Antigen-binding Proteins. Science 242(4877):423-426 (1988).

Blaney, Paul et al. Traceless Solid-phase Organic Synthesis. Chemical Reviews 102(7):2607-2624 (2002).

Bodine, Sue c et al. Identification of Ubiquitin Ligases Required for Skeletal Muscle Atrophy. Science 294(5547)1704-1708 (2001).

Borchardt et al. Targeted actinium-225 in Vivo Generators for Therapy of Ovarian Cancer Cancer Res. 63:5084-50 (2003).

Brinkmann, Ulrich et al. The making of bispecific antibodies. MAbs 9(2):182-212 (2017).

Bulmus et al. A new pH-responsive and glutathione-reactive, endosomal membrane-disruptive polymeric carrier for intracellular delivery of biomolecular drugs. J Controlled Release 93:105-120 (2003).

Burke et al. siRNA-mediated knockdown of P450 oxidoreductase in rats: a tool to reduce metabolism by CYPs and increase exposure of high clearance compounds. Pharm. Res. 31(12):3445-3460 (2014).

Burlina, Fabienne et al. Chemical Engineering of RNase Resistant and Catalytically Active Hammerhead Ribozymes. Bioorganic and Medicinal Chemistry 5(11):1999-2010 (1997).

Casi, Giulio et al. Site-specific Traceless Coupling of Potent Cytotoxic Drugs to Recombinant Antibodies for Pharmacodelivery. Journal of the American Chemical Society 134(13):5887-5892 (2012).

Casset, Florence et al. A Peptide Mimetic Of An Anti-CD4 Monoclonal Antibody by Rational Design. Biochemical and Biophysical Research Communication 307(1):198-205 (2003).

Chen et al. Selection and analysis of an optimized anti-VEGF antibody: Crystal structure of an affinity-matured Fab in complex with antigen. J Mol Bio 293:865-881 (1999).

Chen, Yvonne et al. Selection and Analysis of an Optimized Anti-VEGF Antibody: Crystal Structure of an Affinity-matured Fab in Complex With Antigen. Journal of Molecular Biology 293(4):865-881 (1999).

Chothia, Cyrus et al. Canonical Structures for the Hypervariable Regions of Immunoglobulins. Journal of Molecular Biology 196(4):901-917 (1987).

Chothia, Cyrus et al. Structural Repertoire of the Human VH Segments. Journal of Molecular Biology 227(3):799-817 (1992).

Clackson, Tim et al. Making Antibody Fragments using Phage Display Libraries. Nature 352(6336):624-628 (1991).

Colbere-Garapin, Florence et al. A New Dominant Hybrid Selective Marker for Higher Eukaryotic Cells. Journal of Molecular Biology 150(1):1-14 (1981).

Cole, S.P.C. et al. The EBV-Hybridoma Technique and its Application to Human Lung Cancer. Monoclonal Antibodies and Cancer Therapy 27:77-96 (1985).

Co-pending U.S. Appl. No. 19/263,372, inventors Doppalapudi; Venkata Ramana et al., filed Jul. 8, 2025.

Crouse, Gray F. et al. Expression and Amplification of Engineered Mouse Dihydrofolate Reductase Minigenes. Molecular Cell Biology 3(2):257-266 (1983).

Darimont et al. 8-05 Abstract: A novel Antibody-Oligonucleotide Conjugate (AOC) platform enables efficient regulation of muscle targets in mice. Journal Of Cachexia, Sarcopenia And Muscle 8:999-1080 (2017).

Dawson, Philip E. et al. Modulation of Reactivity in Native Chemical Ligation through the Use of Thiol Additives. Journal of American Chemical Society 119(19):4325-4329 (1997).

Dawson, Philip E. et al. Synthesis of Proteins by Native Chemical Ligation. Science 266(5186):776-779 (1994).

De Pascalis, Roberto et al. Grafting of “Abbreviated” Complementarity-Determining Regions Containing Specificity-Determining Residues Essential for Ligand Contact to Engineer a Less Immunogenic Humanized Monoclonal Antibody. The Journal of Immunology 169(6):3076-3084 (2002).

Dean, Nicholas M. et al. Antisense Oligonucleotide-based Therapeutics for Cancer. Oncogene vol. 22(56):9087-9096 (2003).

Debinski et al. Monovalent immunotoxin containing truncated form of Pseudomonas exotoxin as potent antitumor agent. Cancer Research 52(19):5379-5385 (1992).

Dimasi, Nazzareno et al. Development of a Trispecific Antibody Designed to Simultaneously and Efficiently Target Three Different Antigens on Tumor Cells. Molecular Pharmaceutics 12(9):3490-3501 (2015).

Domingo et al. Transferrin receptor as a target for antibody-drug conjugates. Methods in Enzymology 112:238-247 (1985).

Earnshaw, David J. et al. Modified Oligoribonucleotides as Site-Specific Probes of RNA Structure and Function. Biopolymers (Nucleic Acid Sciences) 48(1):39-55 (1998).

El-Sayed et al. Rational design of composition and activity correlations for pH-responsive and glutathione-reactive polymer therapeutics. J Control Release 104:417-427 (2005).

Flanary et al. Antigen delivery with poly(propylacrylic acid) conjugation enhanced MHC-1 presentation and T-cell activation. Bioconjugate Chem. 20:241-248 (2009).

Fortini et al. DNA damage response by single-strand breaks in terminally differentiated muscle cells and the control of muscle integrity. Cell Death Diff 19(11):1741-1749 (2012).

Goldspiel, Barry R. et al. Human Gene Therapy. Clinical Pharmacy 12(7):488-505 (1993).

Griffey, Richard H. et al. 2'-O-aminopropyl Ribonucleotides: A Zwitterionic Modification that Enhances the Exonuclease Resis-

(56) References Cited

OTHER PUBLICATIONS tance and Biological Activity of Antisense Oligonucleotides. Journal of Medicinal Chemistry 39(26):5100-5109 (1997).
Hackeng, Tilman M et al. Protein Synthesis by Native Chemical Ligation: Expanded Scope by Using Straightforward Methodology. PNAS USA 96(18):10068-10073 (1999).
Hanes, Jozef et al. In Vitro Selection and Evolution of Functional Proteins by Using Ribosome Display. Pnas USA 94(10):4937-4942 (1997).
Hejesen, Christian et al. A Traceless Aryl-triazene Linker for DNA-directed Chemistry. Organic and Biomolecular Chemistry 11(15):2493-2497 (2013).
Henry et al. pH-responsive poly(styrene-alt-maleic anhydride) alkylamide copolymers for intracellular drug delivery. Biomacromolecules 7:2407-2414 (2006).
Hitachi et al. Role of microRNAs in skeletal muscle hypertrophy. Front Physiol 16(4):408 (2014).
*Homo sapiens* DM1 protein kinase (DMPK), transcript variant 7, mRNA. NCBI reference sequence NM_001288766 (Mar. 12, 2019).
Hudson et al. Cellular delivery of hammerhead ribozymes conjugated to a transferrin receptor antibody. Int J Pharmaceuticals 182(1):49-58 (1999).
Huse, William D. et al. Generation of a Large Combinatorial Library of the Immunoglobulin Repertoire in Phage Lambda. Science 246(4935):1275-1281 (1989).
Huston, James S. et al. Protein Engineering of Antibody Binding Sites: Recovery of Specific Activity in an Anti-digoxin Single-chain Fv Analogue Produced in *Escherichia coli.* PNAS USA 85(16):5879-5883 (1988).
Idusogie, Eshoe E. et al. Mapping of the C1q Binding Site on Rituxan, A Chimeric Antibody with a Human IgG1 Fc. The Journal of Immunology 164(8):4178-4184 (2000).
Ishikawa et al. Preparation of monomeric Fab'-horseradish peroxidase conjugate using thiol groups in the hinge and its evaluation in enzyme immunoassay and immunohistochemical staining. Ann N Y Acad Sci. 420:74-89 (1983).
Jones et al. Poly(2-alkylacrylic acid) polymers deliver molecules to the cytosol by pH-sensitive disruption of endosomal vesicles. Biochem J 372:65-75 (2003).
Kabat, Elvin A. et al. Attempts to Locate Complementarity-Determining Residues in the Variable Positions of Light and Heavy Chains. Annals of the New York Academy of Sciences 190:382-393 (1971).
Kabat, Elvin A. et al. Sequences of Proteins of Immunological Interest, 5th Edition. U.S. Department of Health and Human Services NIH Publication No. 91-3242 (1991).
Kaneko, Etsuji et al. Optimizing Therapeutic Antibody Function: Progress with Fc Domain Engineering. Bio Drugs 25(1):1-11 (2011).
Karpeisky, Alexander et al. Highly Efficient Synthesis of 2-O-amino Nucleosides and their Incorporation in Hammerhead Ribozymes. Tetrahedron Letters 39(10):1131-1134 (1998).
Khan et al. Silencing Myostatin Using Cholesterol-conjugated siRNAs Induces Muscle Growth. Molecular Therapy-Nucleic Acids 5:e342 (2016).
Köhler, G. et al. Continuous Cultures of Fused Cells Secreting Antibody of Predefined Specificity. Nature 256(5517):495-497 (1975).
Khormaee et al. Endosomolytic anionic polymer for the cytoplasmic delivery of siRNAs in localized in vivo applications. Adv Funct Mater 23:565-574 (2013).
Koizumi, M. ENA Oligonucleotides as Therapeutics. Current Opinion in Molecular Therapeutics 8(2):144-149 (2006).
Kozbor, Danuta et al. The Production of Monoclonal Antibodies From Human Lymphocytes. Immunology Today 4(3):72-79 (1983).
Kutmeier, G. et al. Assembly of Humanized Antibody Genes from Synthetic Oligonucleotides Using a Single-round PCR. Biotechniques 17(2):242-246 (1994).
Lamminnnaki et al. Crystal structure of a recombinant anti-estradiol fab fragment in complex with 17Beta-Estradiol. J Biol Chem. 276:36687-36694 (2001).
Langlois et al. Cytoplasmic and Nuclear Retained DMPK mRNAS Are Targets for RNA Interference in Myotonic Dystrophy Cells. J biol Chem 280(17):16949-16954 (2005).
Lazar, Greg A. et al. Engineered Antibody Fc Variants with Enhanced Effector Function. PNAS USA 103(11):4005-4010 (2006).
Lefranc, Marie-Paule et al. IMGT, The International ImMunoGeneTics Database. Nucleic Acids Research 27(1):209-212 (1999).
Lefranc, Marie-Paule et al. The IMGT Unique Numbering for Immunoglobulins, T-Cell Receptors and Ig-Like Domains. The Immunologist 7(4):132-136 (1999).
Loakes, David. Survey and Summary: The applications of universal DNA base analogues. Nucleic Acids Research 29(12):2437-2447 (2001).
Lowy, Israel et al. Isolation of Transforming DNA: Cloning the Hamster aprt Gene. Cell 22(3):817-823 (1980).
Lyon, Robert P. et al. Self-Hydrolyzing Maleimides improve the Stability and Pharmacological Properties of Antibody-drug Conjugates. Nature Biotechnology 32(10):1059-1062 (2014).
Maccallum, Robert M. et al. Antibody-antigen interactions: contact analysis and binding site topography. Journal of molecular biology 262(5):732-745 (1996).
Martin, Andrew C. et al., Chapter 3: Protein Sequence and Structure Analysis of Antibody Variable Domains. In: Antibody Engineering Lab Manual (Ed: Duebel, S. and Kontermann, R., Springer-Verlag, Heidelberg) 2:33-51 (2010).
Martinez, Javier et al. Single-Stranded Antisense siRNAs Guide Target RNA Cleavage in RNAi. Cell 110(5):563-574 (2002).
Mcdevitt et al. Tumor Therapy With Targeted Atomic Nanogenerators. Science 294:1537-1540 (2001).
Mcenaney, Patrick J. et al. Antibody-Recruiting Molecules: An Emerging Paradigm for Engaging Immune Function in Treating Human Disease. ACS Chemical Biology 7(7):1139-1151 (2012).
Mei et al. FBXO32 Targets c-Myc for Proteasomal Degradation and Inhibits c-Myc Activity. J Biol Chem 290:16202-16214 (2015).
Miyagishi, et al. Comparison of the Suppressive Effects of Antisense Oligonucleotides and siRNAs Directed Against the Same Targets in Mammalian Cells. Antisense and Nucleic Acid Drug Development 13(1):1-7 (2003).
Miyata et al. Polymer nanotechnology for nucleic acid delivery. Drug Delivery System 31(1):44-53 (2016) (English Abstract).
Moore, Gregory L. et al. Engineered Fc Variant Antibodies with Enhanced Ability to Recruit Complement and Mediate Effector Functions. mAbs 2(2):181-189 (2010).
Morgan, Richard A. et al. Human Gene Therapy. Annual Review of Biochemistry 62:191-217 (1993).
Morrison, Sherie L. et al. Chimeric human antibody molecules: mouse antigen-binding domains with human constant region domains. PNAS USA 81(21):6851-6855 (1984).
Mulders et al. Molecular therapy in myotonic dystrophy: focus on RNA gain-of-function. Hum Mol Gen 19(R1):R90-R97 (2010).
Mulders et al. Supporting Information for Triplet-repeat oligonucleotide-mediated reversal of RNA toxicity in myotonic dystrophy. PNAS 106(33):13915-13920 (2009) (13 pgs).
Mulders et al. Triplet-repeat oligonucleotide-mediated reversal of RNA toxicity in myotonic dystrophy. PNAS 106(33):13915-13920 (2009).
Mulligan, R. C. et al. Selection for Animal Cells That Express the *Escherichia coli* Gene Coding for Xanthine-guanine Phosphoribosyltransferase. PNAS USA 78(4):2072-2076 (1981).
Mulligan, Richard C. The Basic Science of Gene Therapy. Science 260(5110):926-932 (1993).
Naisbitt, D J. et al. Disposition of Amodiaquine and Related Antimalarial Agents in Human Neutrophils: Implications for Drug Design. The Journal of Pharmacology and Experimental Therapeutics 280(2):884-893 (1997).
Natsume, Akito et al. Engineered Antibodies of IgG1/IgG3 Mixed Isotype with Enhanced Cytotoxic Activities. Cancer Research 68(10):3863-3872 (2008).
Neuberger, Michael S. et al. Recombinant Antibodies Possessing Novel Effector Functions. Nature 312(5995):604-608 (1984).
Normand-Sdiqui et al. Oligonucleotide delivery: Uptake of rat transferrin receptor antibody (OX / 26) conjugates into an in vitro

(56) References Cited

OTHER PUBLICATIONS immortalised cell line model of the blood, brain barrier. Int J Pharmaceuticals 163:63-71 (1998).
Obika, Satosh et al. Synthesis of 2'-0,4'-C-methyleneuridine and -cytidine. Novel bicyclic nucleosides having a fixed C3'-endo sugar puckering. Tetrahedron Letters 38(50):8735-8738 (1997).
O'Hare, K. et al. Transformation of Mouse Fibroblasts to Methotrexate Resistance by a Recombinant Plasmid Expressing a Prokaryotic Dihydrofolate Reductase. PNAS USA 78(3):1527-1531 (1981).
Padlan et al. Structure of an antibody-antigen complex: Crystal structure of the HyHEL-10 Fab-lysozyme complex. PNAS USA 86:5938-5942 (1989).
Parmar, Rubina et al. 5'-(E)-Vinylphosphonate: A Stable Phosphate Mimic Can Improve the RNAi Activity of siRNA-GalNAc Conjugates. Chembiochem Communications 17(11):985-989 (2016).
PCT/US2018/064359 International Search Report and Written Opinion dated Apr. 11, 2019.
PCT/US2019/068078 International Search Report and Written Opinion dated Apr. 24, 2020.
PCT/US2021/024303 International Search Report and Written Opinion dated Aug. 31, 2021.
PCT/US2021/024303 Invitation to Pay Additional Fees dated Jun. 24, 2021.
Pei et al. Quantitative evaluation of siRNA delivery in vivo. RNA 16:2553-2563 (2010).
Perrault, Jean-Pierre et al. Mixed Deoxyribo- and Ribo-Oligonucleotides with Catalytic Activity. Nature 344(6266):565-568 (1990).
Pieken, Wolfgang A. et al. Kinetic Characterization of Ribonuclease-Resistant 2'-Modified Hammerhead Ribozymes. Science 253(5017):314-317 (1991).
Pizzamiglio et al. Expression of iron-related proteins differentiate non-cancerous and cancerous breast tumors. Int J Mol Sci. 18(2):410 (2017).
Rangasamy et al. New mechanism for release of endosomal contents: osmotic lysis via nigeri-cin-mediated K+/H+ exchange. Bioconjugate Chem. 29:1047-1059 (2018).
Rosager et al., Transferrin receptor-1 and ferritin heavy and light chains in astrocytic brain tu-mors: Expression and prognostic value. PLoS One 12:e0182954 (2017).
Rudikoff, Stuart et al. Single amino acid substitution altering antigen-binding specificity. Pnas USA 79(6):1979-1983 (1982).
Rychtarcikova et al. Tumor-initiating cells of breast and prostate origin show alterations in the expression of genes related to iron metabolism. Oncotarget. 8:6376-6398 (2017).
Sacheck et al. Rapid disuse and denervation atrophy involve transcriptional changes similar to those of muscle wasting during systemic diseases. FASEB J. 21(1):140-155 (2007).
Santerre, Robert F. et al. Expression of Prokaryotic Genes for Hygromycin B and G418 Resistance as Dominant-selection Markers in Mouse L Cells. Gene 30(1-3): 147-156 (1984).
Sartori et al. Smad2 and 3 transcription factors control muscle mass in adulthood. Am J Physiol Cell Physiol 296:C1248-C1257 (2009).
Schiaffino et al. Mechanisms regulating skeletal muscle growth and atrophy. FEBS J 280(17):4294-4314 (2013).
Schnyder et al. Targeting of skeletal muscle in vitro using biotinylated immunoliposomes. Biochem J 377(Pt.1):61-67 (2004).
Schwarz, Dianne S. et al. Evidence that siRNAs Function as Guides, not Primers, in the *Drosophila* and Human RNAi Pathways. Molecular Cell 10:537-548 (2002).
Sekyere et al. Examination of the distribution of the transferrin homologue, melanotransferrin (tumour antigen p97), in mouse and human. Biochimica et Biophysica Acta 1722(2):131-142 (2005).
Shields, Robert L. et al. High Resolution Mapping of the Binding Site on Human IgG1 for Fc Gamma RI, Fc Gamma RII, Fc Gamma RIII, and FcRn and design of IgG1 Variants with Improved Binding to the Fc Gamma R. Journal of Biological Chemistry 276(9):6591-6604 (2001).
Singh et al. Recent developments in oligonucleotide conjugation. Chem Soc Rev 39(6):2054- 2070 (2010).
Skerra, Arne et al. Assembly of a Functional Immunoglobulin Fv Fragment in *Escherichia coli.* Science 240(4855):1038-1041 (1988).
Stavenhagen, Jeffrey B. et al. Enhancing the Potency of Therapeutic Monoclonal Antibodies via Fc Optimization. Advances in Enzyme Regulation 48(1):152-164 (2008).
Stavenhagen, Jeffrey B. et al. Fc Optimization of Therapeutic Antibodies Enhances their Ability to Kill Tumor Cells In vitro and Controls Tumor Expansion In vivo via Low-Affinity Activating Fcgamma Receptors. Cancer Research 67(18):8882-8890 (2007).
Strop, Pavel et al. Location Matters: Site of Conjugation Modulates Stability and Pharmacokinetics of Antibody Drug Conjugates. Chemistry and Biology 20(2):161-167 (2013).
Sugo et al. Development of antibody-siRNA conjugate targeted to cardiac and skeletal muscles. J Control release 237:1-13 (2016).
Szybalska, Elizabeth Hunter et al. Genetics of Human Cell Lines, IV. DNA-mediated Heritable Transformation of a Biochemical Trait. PNAS USA 48(12):2026-2034 (1962).
Takeda, Shun-Ichi et al. Construction of Chimaeric Processed Immunoglobulin Genes Containing Mouse Variable and Human Constant Region Sequences. Nature 314(6010):452-454 (1985).
Tolstoshev, Paul. Gene Therapy, Concepts, Current Trials and Future Directions. Annual Review Pharmacology and Toxicology 32:573-596 (1993).
Tramontano, Anna et al. Framework Residue 71 Is a Major Determinant of the Position and Conformation of the Second Hypervariable Region in the VH Domains of Immunoglobulins. Journal of Molecular Biology 215(1):175-182 (1990).
Turner et al. The myotonic dystrophies: diagnosis and management. J Neurol Neurosurg Psychiatry 81:358-367 (2010).
Udd, Bjarne et al. The Myotonic Dystrophies: Molecular, Clinical, and Therapeutic Challenges. The Lancet Neurology 11(10):891-905 (2012).
UniProtKB Accession No. A0A2A5YEL5 "Uncharacterized protein", Dec. 20, 2017 [online]. 2-4, 68 [Retrieved on Jul. 29, 2021). Retrieved from the internet: https://www.uniprot.org/uniprot/AOA2A5YEL5.
U.S. Appl. No. 16/435,422 Miscellaneous Communication re: Third Party Submission dated Apr. 1, 2020.
U.S. Appl. No. 16/435,422 Office Action dated Apr. 15, 2020.
U.S. Appl. No. 16/435,422 Office Action dated Jul. 2, 2020.
U.S. Appl. No. 16/435,422 Office Action dated Oct. 31, 2019.
U.S. Appl. No. 16/896,995 Office Action dated Sep. 2, 2020.
U.S. Appl. No. 17/024,624 Office Action dated Jul. 6, 2021.
U.S. Appl. No. 17/024,624 3rd Party Submission filed Feb. 23, 2021.
U.S. Appl. No. 17/024,624 Office Action dated Mar. 19, 2021.
U.S. Appl. No. 17/187,650 Office Action dated Aug. 31, 2021.
U.S. Appl. No. 17/187,650 Office Action dated May 20, 2021.
U.S. Appl. No. 17/214,525 Office Action dated Jan. 27, 2022.
U.S. Appl. No. 17/243,362 Office Action dated Mar. 16, 2023.
U.S. Appl. No. 17/464,607 Office Action dated Jan. 18, 2022.
U.S. Appl. No. 17/464,607 Office Action dated May 5, 2022.
U.S. Appl. No. 17/464,618 Office Action dated Jan. 31, 2022.
U.S. Appl. No. 17/464,618 Office Action dated May 20, 2022.
U.S. Appl. No. 17/499,796 Office Action dated Dec. 3, 2021.
U.S. Appl. No. 17/499,796 Office Action dated Jun. 6, 2022.
U.S. Appl. No. 17/499,800 Office Action dated Feb. 10, 2022.
U.S. Appl. No. 17/529,197 Office Action dated Apr. 27, 2022.
U.S. Appl. No. 17/529,207 Office Action dated Jun. 3, 2022.
U.S. Appl. No. 17/822,342 Office Action dated Aug. 30, 2024.
U.S. Appl. No. 17/822,342 Office Action dated Jun. 16, 2025.
U.S. Appl. No. 17/822,342 Office Action dated Mar. 3, 2025.
U.S. Appl. No. 17/935,922 Office Action dated Feb. 15, 2023.
U.S. Appl. No. 17/935,922 Office Action dated Jun. 13, 2023.
U.S. Appl. No. 18/056,664 Office Action dated May 22, 2024.
U.S. Appl. No. 18/326,903 Office Action dated Apr. 10, 2025.
U.S. Appl. No. 18/326,903 Office Action dated Nov. 8, 2024.
Usman, Nassim et al. Exploiting the Chemical Synthesis of RNA. Trends in Biochemical Sciences 17:334-339 (1992).
Vajdos et al. Comprehensive functional maps of the antigen-binding site of an anti-ErbB2 antibody obtained with shotgun scanning mutagenesis. J Mol Biol 320:415-428 (2002).

(56) References Cited

OTHER PUBLICATIONS

Vajdos, Felix F. et al. Comprehensive functional maps of the antigen-binding site of an anti-ErbB2 antibody obtained with shotgun scanning mutagenesis. Journal of molecular biology 320(2):415-428 (2002).
Verma, Sandeep et al. Modified Oligonucleotides: Synthesis and Strategy for Users. Annual Review of Biochemistry 67(1):99-134 (1998).
Vickers, Timothy A. et al. Efficient Reduction of Target RNAs by Small Interfering RNA and RNase H-dependent Antisense Agents. The Journal of Biological Chemistry 278(9):7108-7118 (2003).
Vignaud, Alban et al. Progressive Skeletal Muscle Weakness in Transgenic Mice Expressing CTG Expansions is Associated With the Activation of the Ubiquitin-proteasome Pathway. Neuromuscular Disorders 20(5):319-325 (2010).
Walker et al. Improved cellular delivery of antisense oligonucleotides using transferrin receptor antibody-oligonucleotide conjugates. Pharmaceutical research 12(10):1548-1553 (1995).
Ward, E Sally et al. Binding Activities of a Repertoire of Single Immunoglobulin Variable Domains Secreted from *Escherichia coli.* Nature 341(6242):544-546 (1989).
Watts, Jonathan K. et al., Chemically Modified siRNA: Tools and Applications. Drug Discovery Today 13(19-20):842-855 (2008).
Wheeler et al. Targeting nuclear RNA for in vivo correction of myotonic dystrophy. Nature 488(7409):111-5 (2012).
Wigler, M. et al. Transformation of Mammalian Cells With an Amplifiable Dominant-acting Gene. PNAS USA 77(6):3567-3570 (1980).
Wigler, Michael et al. Transfer of Purified Herpes Virus Thymidine Kinase Gene to Cultured Mouse Cells. Cell 11(1):223-232 (1977).
Wojtkowiak-Szlachcic et al. Short antisense-locked nucleic acids (all-LNAs) correct alternative splicing abnormalities in myotonic dystrophy. Nucleic Acids Res 43(6):3318-3331 (2015).
Wu, Bin et al. Building Complex Glycopeptides: Development of a Cysteine-free Native Chemical Ligation Protocol. Angewandte Chemie 45(25):4116-4125 (2006).
Wu, George Y. et al. Delivery systems for Gene Therapy. Biotherapy 3(1):87-95 (1991).
Wu, Herren et al. Humanization of a Murine Monoclonal Antibody by Simultaneous Optimization of Framework and CDR residues. Journal of Molecular Biology 294(1):151-162 (1999).
Wu, Peng et al. Site-specific Chemical Modification of Recombinant Proteins Produced in Mammalian Cells by Using the Genetically Encoded Aldehyde Tag. PNAS USA 106(9):3000-3005 (2009).
Xia et al. Intravenous siRNA of brain cancer with receptor targeting and avidin-biotin technology. Pharm Res 24(12):2309-16 (2007).
Xu et al. Delivery systems for siRNA drug development in cancer therapy. Asian Journal of Pharmaceutical Sciences 10(1):1-12 (2015).
Zapata, Gerardo et al. Engineering Linear F(ab')2 Fragments for Efficient Production in *Escherichia coli* and Enhanced Antiproliferative Activity. Protein Engineering 8(10):1057-1062 (1995).
Zhang, Andrew X. et al. A Remote Arene-Binding Site on Prostate Specific Membrane Antigen Revealed by Antibody-Recruiting Small Molecules. Journal of the American Chemical Society 132(36):12711-12716 (2010).
Co-pending U.S. Appl. No. 19/331,924, inventors Geall; Andrew John et al., filed Sep. 17, 2025.
Ghosh, Preetam et al. Comparing 2-nt 3' overhangs against blunt-ended siRNAs: a systems biology based study. BMC Genomics 10 Suppl 1(Suppl 1):S17, 1-14 (2009).
Rodríguez, José A. et al. Binding specificity and internalization properties of an antibody-avidin fusion protein targeting the human transferrin receptor. J Control Release 124(1-2):35-42 (2007).
Watts, Jonathan K. et al. Silencing disease genes in the laboratory and the clinic. The Journal of pathology 226(2):365-379 (2012).

* cited by examiner

SEQUENCE LISTING

```
Sequence total quantity: 116
SEQ ID NO: 1            moltype = RNA  length = 19
FEATURE                 Location/Qualifiers
misc_feature            1..19
                        note = Description of Artificial Sequence: Synthetic
                         oligonucleotide
source                  1..19
                        mol_type = other RNA
                        organism = synthetic construct
SEQUENCE: 1
ccctagaact gtcttcgaa                                              19
```

-continued

```
SEQ ID NO: 2           moltype = RNA  length = 21
FEATURE                Location/Qualifiers
misc_feature           1..21
                       note = Description of Artificial Sequence: Synthetic
                        oligonucleotide
source                 1..21
                       mol_type = other RNA
                       organism = synthetic construct
SEQUENCE: 2
ttcgaagaca gttctagggt t                                          21

SEQ ID NO: 3           moltype = RNA  length = 19
FEATURE                Location/Qualifiers
misc_feature           1..19
                       note = Description of Artificial Sequence: Synthetic
                        oligonucleotide
modified_base          1
                       mod_base = OTHER
                       note = 2'-O-methyl ribonucleoside
modified_base          1..3
                       mod_base = OTHER
                       note = phosphorothioate internucleotide linkage
modified_base          2
                       mod_base = OTHER
                       note = 2'-O-methyl ribonucleoside
modified_base          3
                       mod_base = OTHER
                       note = 2'-O-methyl ribonucleoside
modified_base          4
                       mod_base = OTHER
                       note = 2'-O-methyl ribonucleoside
modified_base          5
                       mod_base = OTHER
                       note = 2'-O-methyl ribonucleoside
modified_base          6
                       mod_base = OTHER
                       note = 2'-O-methyl ribonucleoside
modified_base          7
                       mod_base = OTHER
                       note = 2'-fluoro nucleoside
modified_base          8
                       mod_base = OTHER
                       note = 2'-fluoro nucleoside
modified_base          9
                       mod_base = OTHER
                       note = 2'-fluoro nucleoside
modified_base          10
                       mod_base = OTHER
                       note = 2'-O-methyl ribonucleoside
modified_base          11
                       mod_base = OTHER
                       note = 2'-O-methyl ribonucleoside
modified_base          12
                       mod_base = OTHER
                       note = 2'-O-methyl ribonucleoside
modified_base          13
                       mod_base = OTHER
                       note = 2'-O-methyl ribonucleoside
modified_base          14
                       mod_base = OTHER
                       note = 2'-O-methyl ribonucleoside
modified_base          15
                       mod_base = OTHER
                       note = 2'-O-methyl ribonucleoside
modified_base          16
                       mod_base = OTHER
                       note = 2'-O-methyl ribonucleoside
modified_base          17
                       mod_base = OTHER
                       note = 2'-O-methyl ribonucleoside
modified_base          17..19
                       mod_base = OTHER
                       note = phosphorothioate internucleotide linkage
modified_base          18
                       mod_base = OTHER
                       note = 2'-O-methyl ribonucleoside
modified_base          19
                       mod_base = OTHER
                       note = 2'-O-methyl ribonucleoside
```

-continued

```
source                  1..19
                        mol_type = other RNA
                        organism = synthetic construct
SEQUENCE: 3
ccctagaact gtcttcgaa                                                  19

SEQ ID NO: 4            moltype = RNA  length = 21
FEATURE                 Location/Qualifiers
misc_feature            1..21
                        note = Description of Artificial Sequence: Synthetic
                         oligonucleotide
modified_base           1
                        mod_base = OTHER
                        note = 2'-O-methyl ribonucleoside
modified_base           1..3
                        mod_base = OTHER
                        note = phosphorothioate internucleotide linkage
modified_base           2
                        mod_base = OTHER
                        note = 2'-fluoro nucleoside
modified_base           3
                        mod_base = OTHER
                        note = 2'-O-methyl ribonucleoside
modified_base           4
                        mod_base = OTHER
                        note = 2'-O-methyl ribonucleoside
modified_base           5
                        mod_base = OTHER
                        note = 2'-O-methyl ribonucleoside
modified_base           6
                        mod_base = OTHER
                        note = 2'-fluoro nucleoside
modified_base           7
                        mod_base = OTHER
                        note = 2'-O-methyl ribonucleoside
modified_base           8
                        mod_base = OTHER
                        note = 2'-O-methyl ribonucleoside
modified_base           9
                        mod_base = OTHER
                        note = 2'-O-methyl ribonucleoside
modified_base           10
                        mod_base = OTHER
                        note = 2'-O-methyl ribonucleoside
modified_base           11
                        mod_base = OTHER
                        note = 2'-O-methyl ribonucleoside
modified_base           12
                        mod_base = OTHER
                        note = 2'-O-methyl ribonucleoside
modified_base           13
                        mod_base = OTHER
                        note = 2'-O-methyl ribonucleoside
modified_base           14
                        mod_base = OTHER
                        note = 2'-fluoro nucleoside
modified_base           15
                        mod_base = OTHER
                        note = 2'-O-methyl ribonucleoside
modified_base           16
                        mod_base = OTHER
                        note = 2'-fluoro nucleoside
modified_base           17
                        mod_base = OTHER
                        note = 2'-O-methyl ribonucleoside
modified_base           18
                        mod_base = OTHER
                        note = 2'-O-methyl ribonucleoside
modified_base           19
                        mod_base = OTHER
                        note = 2'-O-methyl ribonucleoside
modified_base           19..21
                        mod_base = OTHER
                        note = phosphorothioate internucleotide linkage
modified_base           20
                        mod_base = OTHER
                        note = 2'-O-methyl ribonucleoside
modified_base           21
                        mod_base = OTHER
```

-continued

```
                        note = 2'-O-methyl ribonucleoside
source                  1..21
                        mol_type = other RNA
                        organism = synthetic construct
SEQUENCE: 4
ttcgaagaca gttctagggt t                                            21

SEQ ID NO: 5            moltype = RNA  length = 19
FEATURE                 Location/Qualifiers
misc_feature            1..19
                        note = Description of Artificial Sequence: Synthetic
                         oligonucleotide
modified_base           1
                        mod_base = OTHER
                        note = 2'-fluoro nucleoside
modified_base           1..3
                        mod_base = OTHER
                        note = phosphorothioate internucleotide linkage
modified_base           2
                        mod_base = OTHER
                        note = 2'-O-methyl ribonucleoside
modified_base           3
                        mod_base = OTHER
                        note = 2'-fluoro nucleoside
modified_base           4
                        mod_base = OTHER
                        note = 2'-O-methyl ribonucleoside
modified_base           5
                        mod_base = OTHER
                        note = 2'-O-methyl ribonucleoside
modified_base           6
                        mod_base = OTHER
                        note = 2'-O-methyl ribonucleoside
modified_base           7
                        mod_base = OTHER
                        note = 2'-fluoro nucleoside
modified_base           8
                        mod_base = OTHER
                        note = 2'-O-methyl ribonucleoside
modified_base           9
                        mod_base = OTHER
                        note = 2'-O-methyl ribonucleoside
modified_base           10
                        mod_base = OTHER
                        note = 2'-fluoro nucleoside
modified_base           11
                        mod_base = OTHER
                        note = 2'-O-methyl ribonucleoside
modified_base           12
                        mod_base = OTHER
                        note = 2'-fluoro nucleoside
modified_base           13
                        mod_base = OTHER
                        note = 2'-O-methyl ribonucleoside
modified_base           14
                        mod_base = OTHER
                        note = 2'-fluoro nucleoside
modified_base           15
                        mod_base = OTHER
                        note = 2'-O-methyl ribonucleoside
modified_base           16
                        mod_base = OTHER
                        note = 2'-O-methyl ribonucleoside
modified_base           17
                        mod_base = OTHER
                        note = 2'-O-methyl ribonucleoside
modified_base           17..19
                        mod_base = OTHER
                        note = phosphorothioate internucleotide linkage
modified_base           18
                        mod_base = OTHER
                        note = 2'-O-methyl ribonucleoside
modified_base           19
                        mod_base = OTHER
                        note = 2'-O-methyl ribonucleoside
source                  1..19
                        mol_type = other RNA
                        organism = synthetic construct
SEQUENCE: 5
```

-continued

```
ccctagaact gtcttcgaa                                                19

SEQ ID NO: 6            moltype = RNA  length = 21
FEATURE                 Location/Qualifiers
misc_feature            1..21
                        note = Description of Artificial Sequence: Synthetic
                         oligonucleotide
modified_base           1..2
                        mod_base = OTHER
                        note = phosphorothioate internucleotide linkage
modified_base           3
                        mod_base = OTHER
                        note = 2'-O-methyl ribonucleoside
modified_base           3..4
                        mod_base = OTHER
                        note = phosphorothioate internucleotide linkage
modified_base           4
                        mod_base = OTHER
                        note = 2'-O-methyl ribonucleoside
modified_base           5
                        mod_base = OTHER
                        note = 2'-fluoro nucleoside
modified_base           6
                        mod_base = OTHER
                        note = 2'-fluoro nucleoside
modified_base           7
                        mod_base = OTHER
                        note = 2'-O-methyl ribonucleoside
modified_base           8
                        mod_base = OTHER
                        note = 2'-O-methyl ribonucleoside
modified_base           9
                        mod_base = OTHER
                        note = 2'-O-methyl ribonucleoside
modified_base           10
                        mod_base = OTHER
                        note = 2'-fluoro nucleoside
modified_base           11
                        mod_base = OTHER
                        note = 2'-fluoro nucleoside
modified_base           12
                        mod_base = OTHER
                        note = 2'-O-methyl ribonucleoside
modified_base           13
                        mod_base = OTHER
                        note = 2'-O-methyl ribonucleoside
modified_base           14
                        mod_base = OTHER
                        note = 2'-fluoro nucleoside
modified_base           14..15
                        mod_base = OTHER
                        note = phosphorothioate internucleotide linkage
modified_base           15
                        mod_base = OTHER
                        note = 2'-O-methyl ribonucleoside
modified_base           16
                        mod_base = OTHER
                        note = 2'-fluoro nucleoside
modified_base           17
                        mod_base = OTHER
                        note = 2'-O-methyl ribonucleoside
modified_base           18
                        mod_base = OTHER
                        note = 2'-O-methyl ribonucleoside
modified_base           19
                        mod_base = OTHER
                        note = 2'-O-methyl ribonucleoside
modified_base           19..21
                        mod_base = OTHER
                        note = phosphorothioate internucleotide linkage
modified_base           20
                        mod_base = OTHER
                        note = 2'-O-methyl ribonucleoside
modified_base           21
                        mod_base = OTHER
                        note = 2'-O-methyl ribonucleoside
source                  1..21
                        mol_type = other RNA
                        organism = synthetic construct
```

```
SEQUENCE: 6
ttcgaagaca gttctagggt t                                          21

SEQ ID NO: 7            moltype = RNA  length = 19
FEATURE                 Location/Qualifiers
misc_feature            1..19
                        note = Description of Artificial Sequence: Synthetic
                         oligonucleotide
modified_base           1..3
                        mod_base = OTHER
                        note = phosphorothioate internucleotide linkage
modified_base           2
                        mod_base = OTHER
                        note = 2'-O-methyl ribonucleoside
modified_base           3
                        mod_base = OTHER
                        note = 2'-fluoro nucleoside
modified_base           4
                        mod_base = OTHER
                        note = 2'-fluoro nucleoside
modified_base           5
                        mod_base = OTHER
                        note = 2'-O-methyl ribonucleoside
modified_base           6
                        mod_base = OTHER
                        note = 2'-O-methyl ribonucleoside
modified_base           7
                        mod_base = OTHER
                        note = 2'-fluoro nucleoside
modified_base           8
                        mod_base = OTHER
                        note = 2'-O-methyl ribonucleoside
modified_base           9
                        mod_base = OTHER
                        note = 2'-O-methyl ribonucleoside
modified_base           10
                        mod_base = OTHER
                        note = 2'-O-methyl ribonucleoside
modified_base           11
                        mod_base = OTHER
                        note = 2'-O-methyl ribonucleoside
modified_base           12
                        mod_base = OTHER
                        note = 2'-O-methyl ribonucleoside
modified_base           13
                        mod_base = OTHER
                        note = 2'-O-methyl ribonucleoside
modified_base           14
                        mod_base = OTHER
                        note = 2'-O-methyl ribonucleoside
modified_base           15
                        mod_base = OTHER
                        note = 2'-O-methyl ribonucleoside
modified_base           16
                        mod_base = OTHER
                        note = 2'-fluoro nucleoside
modified_base           17
                        mod_base = OTHER
                        note = 2'-fluoro nucleoside
modified_base           17..19
                        mod_base = OTHER
                        note = phosphorothioate internucleotide linkage
modified_base           18
                        mod_base = OTHER
                        note = 2'-O-methyl ribonucleoside
modified_base           19
                        mod_base = OTHER
                        note = 2'-O-methyl ribonucleoside
source                  1..19
                        mol_type = other RNA
                        organism = synthetic construct
SEQUENCE: 7
ccctagaact gtcttcgaa                                             19

SEQ ID NO: 8            moltype = RNA  length = 21
FEATURE                 Location/Qualifiers
misc_feature            1..21
                        note = Description of Artificial Sequence: Synthetic
                         oligonucleotide
```

-continued

```
modified_base         1..3
                      mod_base = OTHER
                      note = phosphorothioate internucleotide linkage
modified_base         2
                      mod_base = OTHER
                      note = 2'-fluoro nucleoside
modified_base         3
                      mod_base = OTHER
                      note = 2'-O-methyl ribonucleoside
modified_base         4
                      mod_base = OTHER
                      note = 2'-O-methyl ribonucleoside
modified_base         5
                      mod_base = OTHER
                      note = 2'-O-methyl ribonucleoside
modified_base         6
                      mod_base = OTHER
                      note = 2'-fluoro nucleoside
modified_base         7
                      mod_base = OTHER
                      note = 2'-O-methyl ribonucleoside
modified_base         8
                      mod_base = OTHER
                      note = 2'-O-methyl ribonucleoside
modified_base         9
                      mod_base = OTHER
                      note = 2'-O-methyl ribonucleoside
modified_base         10
                      mod_base = OTHER
                      note = 2'-O-methyl ribonucleoside
modified_base         11
                      mod_base = OTHER
                      note = 2'-O-methyl ribonucleoside
modified_base         12
                      mod_base = OTHER
                      note = 2'-O-methyl ribonucleoside
modified_base         13
                      mod_base = OTHER
                      note = 2'-O-methyl ribonucleoside
modified_base         14
                      mod_base = OTHER
                      note = 2'-fluoro nucleoside
modified_base         15
                      mod_base = OTHER
                      note = 2'-O-methyl ribonucleoside
modified_base         16
                      mod_base = OTHER
                      note = 2'-fluoro nucleoside
modified_base         17
                      mod_base = OTHER
                      note = 2'-O-methyl ribonucleoside
modified_base         18
                      mod_base = OTHER
                      note = 2'-O-methyl ribonucleoside
modified_base         19
                      mod_base = OTHER
                      note = 2'-O-methyl ribonucleoside
modified_base         19..21
                      mod_base = OTHER
                      note = phosphorothioate internucleotide linkage
modified_base         20
                      mod_base = OTHER
                      note = 2'-O-methyl ribonucleoside
modified_base         21
                      mod_base = OTHER
                      note = 2'-O-methyl ribonucleoside
source                1..21
                      mol_type = other RNA
                      organism = synthetic construct
SEQUENCE: 8
ttcgaagaca gttctagggt t                                              21

SEQ ID NO: 9          moltype = RNA  length = 19
FEATURE               Location/Qualifiers
misc_feature          1..19
                      note = Description of Artificial Sequence: Synthetic
                       oligonucleotide
modified_base         1
                      mod_base = OTHER
```

```
                        note = 2'-O-methyl ribonucleoside
modified_base           1..3
                        mod_base = OTHER
                        note = phosphorothioate internucleotide linkage
modified_base           2
                        mod_base = OTHER
                        note = 2'-fluoro nucleoside
modified_base           3
                        mod_base = OTHER
                        note = 2'-fluoro nucleoside
modified_base           4
                        mod_base = OTHER
                        note = 2'-O-methyl ribonucleoside
modified_base           5
                        mod_base = OTHER
                        note = 2'-O-methyl ribonucleoside
modified_base           6
                        mod_base = OTHER
                        note = 2'-O-methyl ribonucleoside
modified_base           7
                        mod_base = OTHER
                        note = 2'-fluoro nucleoside
modified_base           8
                        mod_base = OTHER
                        note = 2'-O-methyl ribonucleoside
modified_base           9
                        mod_base = OTHER
                        note = 2'-O-methyl ribonucleoside
modified_base           10
                        mod_base = OTHER
                        note = 2'-O-methyl ribonucleoside
modified_base           11
                        mod_base = OTHER
                        note = 2'-O-methyl ribonucleoside
modified_base           12
                        mod_base = OTHER
                        note = 2'-O-methyl ribonucleoside
modified_base           13
                        mod_base = OTHER
                        note = 2'-O-methyl ribonucleoside
modified_base           14
                        mod_base = OTHER
                        note = 2'-O-methyl ribonucleoside
modified_base           15
                        mod_base = OTHER
                        note = 2'-O-methyl ribonucleoside
modified_base           16
                        mod_base = OTHER
                        note = 2'-O-methyl ribonucleoside
modified_base           17
                        mod_base = OTHER
                        note = 2'-O-methyl ribonucleoside
modified_base           17..19
                        mod_base = OTHER
                        note = phosphorothioate internucleotide linkage
modified_base           18
                        mod_base = OTHER
                        note = 2'-fluoro nucleoside
source                  1..19
                        mol_type = other RNA
                        organism = synthetic construct
SEQUENCE: 9
ccctagaact gtcttcgaa                                              19

SEQ ID NO: 10           moltype = RNA  length = 21
FEATURE                 Location/Qualifiers
misc_feature            1..21
                        note = Description of Artificial Sequence: Synthetic
                         oligonucleotide
modified_base           1
                        mod_base = OTHER
                        note = 2'-O-methyl ribonucleoside
modified_base           1..3
                        mod_base = OTHER
                        note = phosphorothioate internucleotide linkage
modified_base           2
                        mod_base = OTHER
                        note = 2'-fluoro nucleoside
modified_base           3
```

-continued

```
                        mod_base = OTHER
                        note = 2'-O-methyl ribonucleoside
modified_base           4
                        mod_base = OTHER
                        note = 2'-O-methyl ribonucleoside
modified_base           5
                        mod_base = OTHER
                        note = 2'-O-methyl ribonucleoside
modified_base           6
                        mod_base = OTHER
                        note = 2'-fluoro nucleoside
modified_base           7
                        mod_base = OTHER
                        note = 2'-O-methyl ribonucleoside
modified_base           8
                        mod_base = OTHER
                        note = 2'-O-methyl ribonucleoside
modified_base           9
                        mod_base = OTHER
                        note = 2'-O-methyl ribonucleoside
modified_base           10
                        mod_base = OTHER
                        note = 2'-O-methyl ribonucleoside
modified_base           11
                        mod_base = OTHER
                        note = 2'-O-methyl ribonucleoside
modified_base           12
                        mod_base = OTHER
                        note = 2'-fluoro nucleoside
modified_base           13
                        mod_base = OTHER
                        note = 2'-O-methyl ribonucleoside
modified_base           14
                        mod_base = OTHER
                        note = 2'-fluoro nucleoside
modified_base           15
                        mod_base = OTHER
                        note = 2'-fluoro nucleoside
modified_base           16
                        mod_base = OTHER
                        note = 2'-fluoro nucleoside
modified_base           17
                        mod_base = OTHER
                        note = 2'-O-methyl ribonucleoside
modified_base           18
                        mod_base = OTHER
                        note = 2'-O-methyl ribonucleoside
modified_base           19
                        mod_base = OTHER
                        note = 2'-O-methyl ribonucleoside
modified_base           19..21
                        mod_base = OTHER
                        note = phosphorothioate internucleotide linkage
modified_base           20
                        mod_base = OTHER
                        note = 2'-fluoro nucleoside
modified_base           21
                        mod_base = OTHER
                        note = 2'-O-methyl ribonucleoside
source                  1..21
                        mol_type = other RNA
                        organism = synthetic construct
SEQUENCE: 10
ttcgaagaca gttctagggt t                                                21

SEQ ID NO: 11           moltype = RNA  length = 19
FEATURE                 Location/Qualifiers
misc_feature            1..19
                        note = Description of Artificial Sequence: Synthetic
                         oligonucleotide
modified_base           1..3
                        mod_base = OTHER
                        note = phosphorothioate internucleotide linkage
modified_base           3
                        mod_base = OTHER
                        note = 2'-fluoro nucleoside
modified_base           4
                        mod_base = OTHER
                        note = 2'-fluoro nucleoside
```

-continued

```
modified_base         5
                      mod_base = OTHER
                      note = 2'-O-methyl ribonucleoside
modified_base         6
                      mod_base = OTHER
                      note = 2'-O-methyl ribonucleoside
modified_base         7
                      mod_base = OTHER
                      note = 2'-O-methyl ribonucleoside
modified_base         8
                      mod_base = OTHER
                      note = 2'-O-methyl ribonucleoside
modified_base         9
                      mod_base = OTHER
                      note = 2'-O-methyl ribonucleoside
modified_base         10
                      mod_base = OTHER
                      note = 2'-O-methyl ribonucleoside
modified_base         11
                      mod_base = OTHER
                      note = 2'-O-methyl ribonucleoside
modified_base         12
                      mod_base = OTHER
                      note = 2'-O-methyl ribonucleoside
modified_base         13
                      mod_base = OTHER
                      note = 2'-fluoro nucleoside
modified_base         14
                      mod_base = OTHER
                      note = 2'-fluoro nucleoside
modified_base         15
                      mod_base = OTHER
                      note = 2'-O-methyl ribonucleoside
modified_base         16
                      mod_base = OTHER
                      note = 2'-O-methyl ribonucleoside
modified_base         17
                      mod_base = OTHER
                      note = 2'-O-methyl ribonucleoside
modified_base         17..19
                      mod_base = OTHER
                      note = phosphorothioate internucleotide linkage
modified_base         18
                      mod_base = OTHER
                      note = 2'-O-methyl ribonucleoside
modified_base         19
                      mod_base = OTHER
                      note = 2'-O-methyl ribonucleoside
source                1..19
                      mol_type = other RNA
                      organism = synthetic construct
SEQUENCE: 11
ccctagaact gtcttcgaa                                              19

SEQ ID NO: 12         moltype = RNA  length = 21
FEATURE               Location/Qualifiers
misc_feature          1..21
                      note = Description of Artificial Sequence: Synthetic
                       oligonucleotide
modified_base         1
                      mod_base = OTHER
                      note = 2'-O-methyl ribonucleoside
modified_base         1..3
                      mod_base = OTHER
                      note = phosphorothioate internucleotide linkage
modified_base         2
                      mod_base = OTHER
                      note = 2'-fluoro nucleoside
modified_base         3
                      mod_base = OTHER
                      note = 2'-O-methyl ribonucleoside
modified_base         4
                      mod_base = OTHER
                      note = 2'-O-methyl ribonucleoside
modified_base         5
                      mod_base = OTHER
                      note = 2'-O-methyl ribonucleoside
modified_base         6
                      mod_base = OTHER
```

```
                        note = 2'-fluoro nucleoside
modified_base           7
                        mod_base = OTHER
                        note = 2'-O-methyl ribonucleoside
modified_base           8
                        mod_base = OTHER
                        note = 2'-O-methyl ribonucleoside
modified_base           9
                        mod_base = OTHER
                        note = 2'-O-methyl ribonucleoside
modified_base           10
                        mod_base = OTHER
                        note = 2'-fluoro nucleoside
modified_base           11
                        mod_base = OTHER
                        note = 2'-O-methyl ribonucleoside
modified_base           12
                        mod_base = OTHER
                        note = 2'-O-methyl ribonucleoside
modified_base           13
                        mod_base = OTHER
                        note = 2'-O-methyl ribonucleoside
modified_base           14
                        mod_base = OTHER
                        note = 2'-fluoro nucleoside
modified_base           15
                        mod_base = OTHER
                        note = 2'-O-methyl ribonucleoside
modified_base           16
                        mod_base = OTHER
                        note = 2'-fluoro nucleoside
modified_base           17
                        mod_base = OTHER
                        note = 2'-O-methyl ribonucleoside
modified_base           18
                        mod_base = OTHER
                        note = 2'-O-methyl ribonucleoside
modified_base           19
                        mod_base = OTHER
                        note = 2'-O-methyl ribonucleoside
modified_base           19..21
                        mod_base = OTHER
                        note = phosphorothioate internucleotide linkage
modified_base           20
                        mod_base = OTHER
                        note = 2'-O-methyl ribonucleoside
modified_base           21
                        mod_base = OTHER
                        note = 2'-fluoro nucleoside
source                  1..21
                        mol_type = other RNA
                        organism = synthetic construct
SEQUENCE: 12
ttcgaagaca gttctagggt t                                              21

SEQ ID NO: 13           moltype = RNA  length = 19
FEATURE                 Location/Qualifiers
misc_feature            1..19
                        note = Description of Artificial Sequence: Synthetic
                         oligonucleotide
modified_base           2
                        mod_base = OTHER
                        note = 2'-fluoro nucleoside
modified_base           2..3
                        mod_base = OTHER
                        note = phosphorothioate internucleotide linkage
modified_base           3
                        mod_base = OTHER
                        note = 2'-fluoro nucleoside
modified_base           4
                        mod_base = OTHER
                        note = 2'-O-methyl ribonucleoside
modified_base           4..6
                        mod_base = OTHER
                        note = phosphorothioate internucleotide linkage
modified_base           5
                        mod_base = OTHER
                        note = 2'-O-methyl ribonucleoside
modified_base           6
```

-continued

```
                          mod_base = OTHER
                          note = 2'-O-methyl ribonucleoside
modified_base             7
                          mod_base = OTHER
                          note = 2'-fluoro nucleoside
modified_base             8
                          mod_base = OTHER
                          note = 2'-O-methyl ribonucleoside
modified_base             11
                          mod_base = OTHER
                          note = 2'-O-methyl ribonucleoside
modified_base             12
                          mod_base = OTHER
                          note = 2'-O-methyl ribonucleoside
modified_base             13
                          mod_base = OTHER
                          note = 2'-O-methyl ribonucleoside
modified_base             14
                          mod_base = OTHER
                          note = 2'-O-methyl ribonucleoside
modified_base             15
                          mod_base = OTHER
                          note = 2'-O-methyl ribonucleoside
modified_base             16
                          mod_base = OTHER
                          note = 2'-O-methyl ribonucleoside
modified_base             17..19
                          mod_base = OTHER
                          note = phosphorothioate internucleotide linkage
source                    1..19
                          mol_type = other RNA
                          organism = synthetic construct
SEQUENCE: 13
ccctagaact gtcttcgaa                                                19

SEQ ID NO: 14             moltype = RNA  length = 21
FEATURE                   Location/Qualifiers
misc_feature              1..21
                          note = Description of Artificial Sequence: Synthetic
                           oligonucleotide
modified_base             1
                          mod_base = OTHER
                          note = 2'-O-methyl ribonucleoside
modified_base             1..3
                          mod_base = OTHER
                          note = phosphorothioate internucleotide linkage
modified_base             2
                          mod_base = OTHER
                          note = 2'-fluoro nucleoside
modified_base             3
                          mod_base = OTHER
                          note = 2'-O-methyl ribonucleoside
modified_base             4
                          mod_base = OTHER
                          note = 2'-O-methyl ribonucleoside
modified_base             5
                          mod_base = OTHER
                          note = 2'-O-methyl ribonucleoside
modified_base             6
                          mod_base = OTHER
                          note = 2'-fluoro nucleoside
modified_base             7
                          mod_base = OTHER
                          note = 2'-O-methyl ribonucleoside
modified_base             8
                          mod_base = OTHER
                          note = 2'-O-methyl ribonucleoside
modified_base             9
                          mod_base = OTHER
                          note = 2'-O-methyl ribonucleoside
modified_base             10
                          mod_base = OTHER
                          note = 2'-O-methyl ribonucleoside
modified_base             10..11
                          mod_base = OTHER
                          note = phosphorothioate internucleotide linkage
modified_base             11
                          mod_base = OTHER
                          note = 2'-O-methyl ribonucleoside
```

-continued

```
modified_base        13
                     mod_base = OTHER
                     note = 2'-O-methyl ribonucleoside
modified_base        14
                     mod_base = OTHER
                     note = 2'-fluoro nucleoside
modified_base        15
                     mod_base = OTHER
                     note = 2'-fluoro nucleoside
modified_base        16
                     mod_base = OTHER
                     note = 2'-fluoro nucleoside
modified_base        17
                     mod_base = OTHER
                     note = 2'-O-methyl ribonucleoside
modified_base        18
                     mod_base = OTHER
                     note = 2'-O-methyl ribonucleoside
modified_base        19
                     mod_base = OTHER
                     note = 2'-O-methyl ribonucleoside
modified_base        19..21
                     mod_base = OTHER
                     note = phosphorothioate internucleotide linkage
modified_base        20
                     mod_base = OTHER
                     note = 2'-fluoro nucleoside
modified_base        21
                     mod_base = OTHER
                     note = 2'-O-methyl ribonucleoside
source               1..21
                     mol_type = other RNA
                     organism = synthetic construct
SEQUENCE: 14
ttcgaagaca gttctagggt t                                                21

SEQ ID NO: 15        moltype = RNA  length = 19
FEATURE              Location/Qualifiers
misc_feature         1..19
                     note = Description of Artificial Sequence: Synthetic
                      oligonucleotide
modified_base        1
                     mod_base = OTHER
                     note = 2'-O-methyl ribonucleoside
modified_base        1..3
                     mod_base = OTHER
                     note = phosphorothioate internucleotide linkage
modified_base        2
                     mod_base = OTHER
                     note = 2'-O-methyl ribonucleoside
modified_base        3
                     mod_base = OTHER
                     note = 2'-O-methyl ribonucleoside
modified_base        4
                     mod_base = OTHER
                     note = 2'-O-methyl ribonucleoside
modified_base        5
                     mod_base = OTHER
                     note = 2'-O-methyl ribonucleoside
modified_base        6
                     mod_base = OTHER
                     note = 2'-O-methyl ribonucleoside
modified_base        7
                     mod_base = OTHER
                     note = 2'-O-methyl ribonucleoside
modified_base        8
                     mod_base = OTHER
                     note = 2'-O-methyl ribonucleoside
modified_base        9
                     mod_base = OTHER
                     note = 2'-O-methyl ribonucleoside
modified_base        10
                     mod_base = OTHER
                     note = 2'-O-methyl ribonucleoside
modified_base        11
                     mod_base = OTHER
                     note = 2'-O-methyl ribonucleoside
modified_base        11..12
                     mod_base = OTHER
```

```
                         note = phosphorothioate internucleotide linkage
modified_base            13
                         mod_base = OTHER
                         note = 2'-fluoro nucleoside
modified_base            14
                         mod_base = OTHER
                         note = 2'-fluoro nucleoside
modified_base            15
                         mod_base = OTHER
                         note = 2'-O-methyl ribonucleoside
modified_base            16
                         mod_base = OTHER
                         note = 2'-O-methyl ribonucleoside
modified_base            17
                         mod_base = OTHER
                         note = 2'-O-methyl ribonucleoside
modified_base            17..19
                         mod_base = OTHER
                         note = phosphorothioate internucleotide linkage
modified_base            19
                         mod_base = OTHER
                         note = 2'-O-methyl ribonucleoside
source                   1..19
                         mol_type = other RNA
                         organism = synthetic construct
SEQUENCE: 15
ccctagaact gtcttcgaa                                                   19

SEQ ID NO: 16            moltype = RNA  length = 21
FEATURE                  Location/Qualifiers
misc_feature             1..21
                         note = Description of Artificial Sequence: Synthetic
                          oligonucleotide
modified_base            1
                         mod_base = OTHER
                         note = 2'-O-methyl ribonucleoside
modified_base            1..3
                         mod_base = OTHER
                         note = phosphorothioate internucleotide linkage
modified_base            2
                         mod_base = OTHER
                         note = 2'-O-methyl ribonucleoside
modified_base            3
                         mod_base = OTHER
                         note = 2'-O-methyl ribonucleoside
modified_base            4
                         mod_base = OTHER
                         note = 2'-O-methyl ribonucleoside
modified_base            6
                         mod_base = OTHER
                         note = 2'-fluoro nucleoside
modified_base            7
                         mod_base = OTHER
                         note = 2'-O-methyl ribonucleoside
modified_base            8
                         mod_base = OTHER
                         note = 2'-O-methyl ribonucleoside
modified_base            9
                         mod_base = OTHER
                         note = 2'-O-methyl ribonucleoside
modified_base            10
                         mod_base = OTHER
                         note = 2'-fluoro nucleoside
modified_base            11
                         mod_base = OTHER
                         note = 2'-O-methyl ribonucleoside
modified_base            13
                         mod_base = OTHER
                         note = 2'-O-methyl ribonucleoside
modified_base            14
                         mod_base = OTHER
                         note = 2'-fluoro nucleoside
modified_base            16
                         mod_base = OTHER
                         note = 2'-fluoro nucleoside
modified_base            17
                         mod_base = OTHER
                         note = 2'-O-methyl ribonucleoside
modified_base            18
```

-continued

```
                        mod_base = OTHER
                        note = 2'-O-methyl ribonucleoside
modified_base           19
                        mod_base = OTHER
                        note = 2'-O-methyl ribonucleoside
modified_base           19..20
                        mod_base = OTHER
                        note = phosphorothioate internucleotide linkage
modified_base           20
                        mod_base = OTHER
                        note = 2'-O-methyl ribonucleoside
modified_base           21
                        mod_base = OTHER
                        note = 2'-fluoro nucleoside
source                  1..21
                        mol_type = other RNA
                        organism = synthetic construct
SEQUENCE: 16
ttcgaagaca gttctagggt t                                     21

SEQ ID NO: 17           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 17
YTFTNYWMH                                                   9

SEQ ID NO: 18           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 18
EINPINGRSN YAQKFQG                                          17

SEQ ID NO: 19           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 19
GTRAMHY                                                     7

SEQ ID NO: 20           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 20
EINPINGRSN YAEKFQG                                          17

SEQ ID NO: 21           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 21
EINPIQGRSN YAEKFQG                                          17

SEQ ID NO: 22           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 22
RTSENIYNNL A                                                11
```

```
SEQ ID NO: 23          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 23
AATNLAD                                                   7

SEQ ID NO: 24          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 24
QHFWGTPLT                                                 9

SEQ ID NO: 25          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 25
AATNLAE                                                   7

SEQ ID NO: 26          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 26
QHFWGTPLTF                                                10

SEQ ID NO: 27          moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 27
RTSENIYSNL A                                              11

SEQ ID NO: 28          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 28
AGTNLAD                                                   7

SEQ ID NO: 29          moltype = AA  length = 116
FEATURE                Location/Qualifiers
REGION                 1..116
                       note = Description of Artificial Sequence: Synthetic
                        polypeptide
source                 1..116
                       mol_type = protein
                       organism = synthetic construct
SEQUENCE: 29
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSS      116

SEQ ID NO: 30          moltype = AA  length = 116
FEATURE                Location/Qualifiers
REGION                 1..116
                       note = Description of Artificial Sequence: Synthetic
                        polypeptide
source                 1..116
```

```
                         mol_type = protein
                         organism = synthetic construct
SEQUENCE: 30
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSS      116

SEQ ID NO: 31            moltype = AA  length = 116
FEATURE                  Location/Qualifiers
REGION                   1..116
                         note = Description of Artificial Sequence: Synthetic
                          polypeptide
source                   1..116
                         mol_type = protein
                         organism = synthetic construct
SEQUENCE: 31
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSS      116

SEQ ID NO: 32            moltype = AA  length = 116
FEATURE                  Location/Qualifiers
REGION                   1..116
                         note = Description of Artificial Sequence: Synthetic
                          polypeptide
source                   1..116
                         mol_type = protein
                         organism = synthetic construct
SEQUENCE: 32
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSS      116

SEQ ID NO: 33            moltype = AA  length = 116
FEATURE                  Location/Qualifiers
REGION                   1..116
                         note = Description of Artificial Sequence: Synthetic
                          polypeptide
source                   1..116
                         mol_type = protein
                         organism = synthetic construct
SEQUENCE: 33
QVQLQQPGAE LVKPGASVKL SCKASGYTFT NYWMHWVKQR PGQGLEWIGE INPINGRSNY  60
GERFKTKATL TVDKSSSTAY MQLSSLTSED SAVYYCARGT RAMHYWGQGT SVTVSS      116

SEQ ID NO: 34            moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 34
DIQMTQSPSS LSASVGDRVT ITCRTSENIY NNLAWYQQKP GKSPKLLIYA ATNLADGVPS  60
RFSGSGSGTD YTLTISSLQP EDFATYYCQH FWGTPLTFGG GTKVEIK                107

SEQ ID NO: 35            moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 35
DIQMTQSPSS LSASVGDRVT ITCRTSENIY NNLAWYQQKP GKAPKLLIYA ATNLADGVPS  60
RFSGSGSGTD YTLTISSLQP EDFATYYCQH FWGTPLTFGG GTKVEIK                107

SEQ ID NO: 36            moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 36
DIQMTQSPSS LSASVGDRVT ITCRTSENIY NNLAWYQQKP GKAPKLLIYA ATNLAEGVPS  60
RFSGSGSGTD YTLTISSLQP EDFATYYCQH FWGTPLTFGG GTKVEIK                107

SEQ ID NO: 37            moltype = AA  length = 107
```

-continued

```
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 37
DIQMTQSPSS LSASVGDRVT ITCRTSENIY SNLAWYQQKP GKAPKLLIYA GTNLADGVPS  60
RFSGSGSGTD YTLTISSLQP EDFANYYCQH FWGTPLTFGG GTKVEIK                107

SEQ ID NO: 38          moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 38
DIQMTQSPAS LSVSVGETVT ITCRTSENIY NNLAWYQQKQ GKSPQLLVYA ATNLADGVPS  60
RFSGSGSGTQ YSLKINSLQS EDFGNYYCQH FWGTPLTFGA GTKLELK                107

SEQ ID NO: 39          moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 39
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 40          moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 40
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 41          moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 41
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC GVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 42          moltype = AA  length = 445
FEATURE                Location/Qualifiers
```

-continued

```
REGION                  1..445
                        note = Description of Artificial Sequence: Synthetic
                         polypeptide
source                  1..445
                        mol_type = protein
                        organism = synthetic construct
SEQUENCE: 42
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKARPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 43           moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 43
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 44           moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 44
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVAVSHEDP EVKFNWYVDG VEVHNAKTKP REEQYGSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 45           moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 45
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 46           moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 46
```

-continued

```
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 47          moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 47
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC GVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 48          moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 48
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKARPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 49          moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 49
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 50          moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 50
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVAVSHEDP EVKFNWYVDG VEVHNAKTKP REEQYGSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
```

-continued

```
VFSCSVMHEA LHNHYTQKSL SLSPG                                  445

SEQ ID NO: 51          moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 51
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                  445

SEQ ID NO: 52          moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 52
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                  445

SEQ ID NO: 53          moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 53
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC GVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                  445

SEQ ID NO: 54          moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 54
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKARPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                  445

SEQ ID NO: 55          moltype = AA  length = 445
FEATURE                Location/Qualifiers
REGION                 1..445
                       note = Description of Artificial Sequence: Synthetic
                        polypeptide
```

```
source                  1..445
                        mol_type = protein
                        organism = synthetic construct
SEQUENCE: 55
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 56           moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 56
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVAVSHEDP EVKFNWYVDG VEVHNAKTKP REEQYGSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 57           moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 57
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 58           moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 58
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 59           moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 59
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
```

```
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC GVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 60          moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 60
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKARPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 61          moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 61
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 62          moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 62
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVAVSHEDP EVKFNWYVDG VEVHNAKTKP REEQYGSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 63          moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 63
DIQMTQSPSS LSASVGDRVT ITCRTSENIY NNLAWYQQKP GKSPKLLIYA ATNLADGVPS  60
RFSGSGSGTD YTLTISSLQP EDFATYYCQH FWGTPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 64          moltype = AA  length = 214
FEATURE                Location/Qualifiers
REGION                 1..214
                       note = Description of Artificial Sequence: Synthetic
                        polypeptide
```

```
source                  1..214
                        mol_type = protein
                        organism = synthetic construct
SEQUENCE: 64
DIQMTQSPSS LSASVGDRVT ITCRTSENIY NNLAWYQQKP GKAPKLLIYA ATNLADGVPS  60
RFSGSGSGTD YTLTISSLQP EDFATYYCQH FWGTPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 65           moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 65
DIQMTQSPSS LSASVGDRVT ITCRTSENIY NNLAWYQQKP GKAPKLLIYA ATNLAEGVPS  60
RFSGSGSGTD YTLTISSLQP EDFATYYCQH FWGTPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 66           moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 66
DIQMTQSPSS LSASVGDRVT ITCRTSENIY SNLAWYQQKP GKAPKLLIYA GTNLADGVPS  60
RFSGSGSGTD YTLTISSLQP EDFANYYCQH FWGTPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 67           moltype = AA  length = 24
FEATURE                 Location/Qualifiers
REGION                  1..24
                        note = Description of Unknown:INF7 sequence
source                  1..24
                        mol_type = protein
                        organism = unidentified
SEQUENCE: 67
CGIFGEIEEL IEEGLENLID WGNA                                        24

SEQ ID NO: 68           moltype = AA  length = 24
FEATURE                 Location/Qualifiers
REGION                  1..24
                        note = Description of Unknown:INF7 sequence
source                  1..24
                        mol_type = protein
                        organism = unidentified
SEQUENCE: 68
GLFEAIEGFI ENGWEGMIDG WYGC                                        24

SEQ ID NO: 69           moltype = AA  length = 27
FEATURE                 Location/Qualifiers
REGION                  1..27
                        note = Description of Unknown:INF7 sequence
source                  1..27
                        mol_type = protein
                        organism = unidentified
SEQUENCE: 69
GLFEAIEGFI ENGWEGMIWD YGSGSCG                                     27

SEQ ID NO: 70           moltype = AA  length = 23
FEATURE                 Location/Qualifiers
REGION                  1..23
                        note = Description of Unknown:INF7 sequence
source                  1..23
                        mol_type = protein
                        organism = unidentified
SEQUENCE: 70
GLFEAIEGFI ENGWEGMIDG WYG                                         23

SEQ ID NO: 71           moltype = AA  length = 27
FEATURE                 Location/Qualifiers
```

```
REGION                 1..27
                       note = Description of Unknown:INF7 sequence
source                 1..27
                       mol_type = protein
                       organism = unidentified
SEQUENCE: 71
GLFEAIEGFI ENGWEGMIWD YGSGSCK                                      27

SEQ ID NO: 72          moltype = AA  length = 27
FEATURE                Location/Qualifiers
REGION                 1..27
                       note = Description of Unknown:melittin sequence
source                 1..27
                       mol_type = protein
                       organism = unidentified
SEQUENCE: 72
CLIGAILKVL ATGLPTLISW IKNKRKQ                                      27

SEQ ID NO: 73          moltype = AA  length = 26
FEATURE                Location/Qualifiers
REGION                 1..26
                       note = Description of Unknown:melittin sequence
source                 1..26
                       mol_type = protein
                       organism = unidentified
SEQUENCE: 73
GIGAVLKVLT TGLPALISWI KRKRQQ                                       26

SEQ ID NO: 74          moltype = AA  length = 13
FEATURE                Location/Qualifiers
REGION                 1..13
                       note = Description of Unknown:meucin sequence
source                 1..13
                       mol_type = protein
                       organism = unidentified
SEQUENCE: 74
IFGAIAGLLK NIF                                                     13

SEQ ID NO: 75          moltype = AA  length = 18
FEATURE                Location/Qualifiers
REGION                 1..18
                       note = Description of Unknown:meucin sequence
source                 1..18
                       mol_type = protein
                       organism = unidentified
SEQUENCE: 75
FFGHLFKLAT KIIPSLFQ                                                18

SEQ ID NO: 76          moltype = AA  length = 21
FEATURE                Location/Qualifiers
source                 1..21
                       mol_type = protein
                       organism = Simian virus 40
SEQUENCE: 76
KETWWETWWT EWSQPKKKRK V                                            21

SEQ ID NO: 77          moltype = AA  length = 19
FEATURE                Location/Qualifiers
REGION                 1..19
                       note = Description of Unknown:pVEC sequence
source                 1..19
                       mol_type = protein
                       organism = unidentified
SEQUENCE: 77
LLIILRRRRI RKQAHAHSK                                               19

SEQ ID NO: 78          moltype = AA  length = 26
FEATURE                Location/Qualifiers
REGION                 1..26
                       note = Description of Artificial Sequence: Synthetic peptide
source                 1..26
                       mol_type = protein
                       organism = synthetic construct
SEQUENCE: 78
DPKGDPKGVT VTVTVTVTGK GDPKPD                                       26

SEQ ID NO: 79          moltype = AA  length = 27
FEATURE                Location/Qualifiers
REGION                 1..27
```

-continued

```
                        note = Description of Artificial Sequence: Synthetic peptide
source                  1..27
                        mol_type = protein
                        organism = synthetic construct
SEQUENCE: 79
GWTLNSAGYL LGKINLKALA ALAKKIL                                        27

SEQ ID NO: 80           moltype = AA  length = 21
FEATURE                 Location/Qualifiers
REGION                  1..21
                        note = Description of Unknown:TP10 sequence
source                  1..21
                        mol_type = protein
                        organism = unidentified
SEQUENCE: 80
AGYLLGKINL KALAALAKKI L                                              21

SEQ ID NO: 81           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 81
GALFLGFLGA AGSTMGA                                                   17

SEQ ID NO: 82           moltype = AA  length = 20
FEATURE                 Location/Qualifiers
source                  1..20
                        mol_type = protein
                        organism = Herpes simplex virus
SEQUENCE: 82
HGLASTLTRW AHYNALIRAF                                                20

SEQ ID NO: 83           moltype = AA  length = 20
FEATURE                 Location/Qualifiers
REGION                  1..20
                        note = Description of Unknown:CADY sequence
source                  1..20
                        mol_type = protein
                        organism = unidentified
SEQUENCE: 83
GLWRALWRLL RSLWRLLWRA                                                20

SEQ ID NO: 84           moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 84
WEAALAEALA EALAEHLAEA LAEALEALAA                                     30

SEQ ID NO: 85           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 85
GLFEAIEGFI ENGWEGMIDG WYGC                                           24

SEQ ID NO: 86           moltype = AA  length = 23
FEATURE                 Location/Qualifiers
REGION                  1..23
                        note = Description of Artificial Sequence: Synthetic peptide
source                  1..23
                        mol_type = protein
                        organism = synthetic construct
SEQUENCE: 86
GLFGAIAGFI ENGWEGMIDG WYG                                            23

SEQ ID NO: 87           moltype = AA  length = 36
FEATURE                 Location/Qualifiers
REGION                  1..36
```

```
                        note = Description of Artificial Sequence: Synthetic
                         polypeptide
source                  1..36
                        mol_type = protein
                        organism = synthetic construct
SEQUENCE: 87
GLFGAIAGFI ENGWEGMIDG RQIKIWFQNR RMKWKK                            36

SEQ ID NO: 88           moltype = AA  length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 88
GLFGAIAGFI ENGWEGMIDG SSKKKK                                       26

SEQ ID NO: 89           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 89
GLFEAIAGFI ENGWEGMIDG GGYC                                         24

SEQ ID NO: 90           moltype = AA  length = 23
FEATURE                 Location/Qualifiers
REGION                  1..23
                        note = Description of Artificial Sequence: Synthetic peptide
source                  1..23
                        mol_type = protein
                        organism = synthetic construct
SEQUENCE: 90
GLFHAIAHFI HGGWHGLIHG WYG                                          23

SEQ ID NO: 91           moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 91
GLFEAIEGFI ENGWEGLAEA LAEALEALAA                                   30

SEQ ID NO: 92           moltype = AA  length = 29
FEATURE                 Location/Qualifiers
REGION                  1..29
                        note = Description of Artificial Sequence: Synthetic peptide
source                  1..29
                        mol_type = protein
                        organism = synthetic construct
SEQUENCE: 92
KWKLFKKIGA VLKVLTTGYG RKKRRQRRR                                    29

SEQ ID NO: 93           moltype = AA  length = 16
FEATURE                 Location/Qualifiers
source                  1..16
                        mol_type = protein
                        organism = Drosophila sp.
SEQUENCE: 93
RQIKIWFQNR RMKWKK                                                  16

SEQ ID NO: 94           moltype = AA  length = 13
FEATURE                 Location/Qualifiers
source                  1..13
                        mol_type = protein
                        organism = Human immunodeficiency virus
SEQUENCE: 94
GRKKRRQRRR PPQ                                                     13

SEQ ID NO: 95           moltype = AA  length = 18
FEATURE                 Location/Qualifiers
source                  1..18
                        mol_type = protein
```

```
                        organism = Mus sp.
SEQUENCE: 95
LLIILRRRIR KQAHAHSK                                              18

SEQ ID NO: 96           moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 96
GWTLNSAGYL LGKINLKALA ALAKKIL                                    27

SEQ ID NO: 97           moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 97
GALFLGFLGA AGSTMGAWSQ PKKKRKV                                    27

SEQ ID NO: 98           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 98
KETWWETWWT EWSQPKKKRK V                                          21

SEQ ID NO: 99           moltype = AA  length = 12
FEATURE                 Location/Qualifiers
REGION                  1..12
                        note = Description of Artificial Sequence: Synthetic peptide
VARIANT                 7..12
                        note = Residues may be deleted
source                  1..12
                        mol_type = protein
                        organism = synthetic construct
SEQUENCE: 99
RRRRRRRRRR RR                                                    12

SEQ ID NO: 100          moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 100
KLALKLALKA LKAALKLA                                              18

SEQ ID NO: 101          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 101
RRWWRRWRR                                                        9

SEQ ID NO: 102          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 102
CGYGPKKKRK VGG                                                   13

SEQ ID NO: 103          moltype = AA  length = 8
FEATURE                 Location/Qualifiers
REGION                  1..8
```

```
                        note = Description of Artificial Sequence: Synthetic peptide
source                  1..8
                        mol_type = protein
                        organism = synthetic construct
SEQUENCE: 103
KKKKKKKK                                                                8

SEQ ID NO: 104          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 104
MVRRFLVTLR IRRACGPPRV RV                                                22

SEQ ID NO: 105          moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 105
LSTAADMQGV VTDGMASGLD KDYLKPDD                                          28

SEQ ID NO: 106          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 106
GGFG                                                                    4

SEQ ID NO: 107          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 107
ALAL                                                                    4

SEQ ID NO: 108          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 108
GFLG                                                                    4

SEQ ID NO: 109          moltype = AA  length = 17
FEATURE                 Location/Qualifiers
REGION                  1..17
                        note = Description of Artificial Sequence: Synthetic peptide
VARIANT                 6
                        note = N or Q
VARIANT                 13
                        note = Q or E
source                  1..17
                        mol_type = protein
                        organism = synthetic construct
SEQUENCE: 109
EINPIXGRSN YAXKFQG                                                      17

SEQ ID NO: 110          moltype = AA  length = 11
FEATURE                 Location/Qualifiers
REGION                  1..11
                        note = Description of Artificial Sequence: Synthetic peptide
VARIANT                 8
                        note = N or S
source                  1..11
                        mol_type = protein
```

```
                         organism = synthetic construct
SEQUENCE: 110
RTSENIYXNL A                                                  11

SEQ ID NO: 111           moltype = AA  length = 7
FEATURE                  Location/Qualifiers
REGION                   1..7
                         note = Description of Artificial Sequence: Synthetic peptide
VARIANT                  2
                         note = A or G
VARIANT                  7
                         note = D or E
source                   1..7
                         mol_type = protein
                         organism = synthetic construct
SEQUENCE: 111
AXTNLAX                                                       7

SEQ ID NO: 112           moltype = AA  length = 10
FEATURE                  Location/Qualifiers
REGION                   1..10
                         note = Description of Artificial Sequence: Synthetic peptide
VARIANT                  10
                         note = F or absent
source                   1..10
                         mol_type = protein
                         organism = synthetic construct
SEQUENCE: 112
QHFWGTPLTX                                                    10

SEQ ID NO: 113           moltype = AA  length = 7
FEATURE                  Location/Qualifiers
REGION                   1..7
                         note = Description of Artificial Sequence: Synthetic peptide
VARIANT                  7
                         note = D or E
source                   1..7
                         mol_type = protein
                         organism = synthetic construct
SEQUENCE: 113
AATNLAX                                                       7

SEQ ID NO: 114           moltype = RNA  length = 19
FEATURE                  Location/Qualifiers
misc_feature             1..19
                         note = Description of Artificial Sequence: Synthetic
                          oligonucleotide
modified_base            1
                         mod_base = OTHER
                         note = 2'-O-methyl ribonucleoside
modified_base            1..3
                         mod_base = OTHER
                         note = phosphorothioate internucleotide linkage
modified_base            2
                         mod_base = OTHER
                         note = 2'-O-methyl ribonucleoside
modified_base            3
                         mod_base = OTHER
                         note = 2'-O-methyl ribonucleoside
modified_base            4
                         mod_base = OTHER
                         note = 2'-O-methyl ribonucleoside
modified_base            5
                         mod_base = OTHER
                         note = 2'-O-methyl ribonucleoside
modified_base            6
                         mod_base = OTHER
                         note = 2'-O-methyl ribonucleoside
modified_base            7
                         mod_base = OTHER
                         note = 2'-fluoro nucleoside
modified_base            8
                         mod_base = OTHER
                         note = 2'-fluoro nucleoside
modified_base            9
                         mod_base = OTHER
                         note = 2'-fluoro nucleoside
modified_base            10
                         mod_base = OTHER
```

```
                        note = 2'-O-methyl ribonucleoside
modified_base           11
                        mod_base = OTHER
                        note = 2'-O-methyl ribonucleoside
modified_base           12
                        mod_base = OTHER
                        note = 2'-O-methyl ribonucleoside
modified_base           13
                        mod_base = OTHER
                        note = 2'-O-methyl ribonucleoside
modified_base           14
                        mod_base = OTHER
                        note = 2'-O-methyl ribonucleoside
modified_base           15
                        mod_base = OTHER
                        note = 2'-O-methyl ribonucleoside
modified_base           16
                        mod_base = OTHER
                        note = 2'-O-methyl ribonucleoside
modified_base           17
                        mod_base = OTHER
                        note = 2'-O-methyl ribonucleoside
modified_base           17..19
                        mod_base = OTHER
                        note = phosphorothioate internucleotide linkage
modified_base           18
                        mod_base = OTHER
                        note = 2'-O-methyl ribonucleoside
modified_base           19
                        mod_base = OTHER
                        note = 2'-O-methyl ribonucleoside
source                  1..19
                        mol_type = other RNA
                        organism = synthetic construct
SEQUENCE: 114
ccctagaact gtcttcgaa                                            19

SEQ ID NO: 115          moltype = RNA  length = 21
FEATURE                 Location/Qualifiers
misc_feature            1..21
                        note = Description of Artificial Sequence: Synthetic
                         oligonucleotide
modified_base           1
                        mod_base = OTHER
                        note = 2'-O-methyl ribonucleoside
modified_base           1..3
                        mod_base = OTHER
                        note = phosphorothioate internucleotide linkage
modified_base           2
                        mod_base = OTHER
                        note = 2'-fluoro nucleoside
modified_base           3
                        mod_base = OTHER
                        note = 2'-O-methyl ribonucleoside
modified_base           4
                        mod_base = OTHER
                        note = 2'-O-methyl ribonucleoside
modified_base           5
                        mod_base = OTHER
                        note = 2'-O-methyl ribonucleoside
modified_base           6
                        mod_base = OTHER
                        note = 2'-fluoro nucleoside
modified_base           7
                        mod_base = OTHER
                        note = 2'-O-methyl ribonucleoside
modified_base           8
                        mod_base = OTHER
                        note = 2'-O-methyl ribonucleoside
modified_base           9
                        mod_base = OTHER
                        note = 2'-O-methyl ribonucleoside
modified_base           10
                        mod_base = OTHER
                        note = 2'-O-methyl ribonucleoside
modified_base           11
                        mod_base = OTHER
                        note = 2'-O-methyl ribonucleoside
modified_base           12
```

-continued

```
                        mod_base = OTHER
                        note = 2'-O-methyl ribonucleoside
modified_base           13
                        mod_base = OTHER
                        note = 2'-O-methyl ribonucleoside
modified_base           14
                        mod_base = OTHER
                        note = 2'-fluoro nucleoside
modified_base           15
                        mod_base = OTHER
                        note = 2'-O-methyl ribonucleoside
modified_base           16
                        mod_base = OTHER
                        note = 2'-fluoro nucleoside
modified_base           17
                        mod_base = OTHER
                        note = 2'-O-methyl ribonucleoside
modified_base           18
                        mod_base = OTHER
                        note = 2'-O-methyl ribonucleoside
modified_base           19
                        mod_base = OTHER
                        note = 2'-O-methyl ribonucleoside
modified_base           19..21
                        mod_base = OTHER
                        note = phosphorothioate internucleotide linkage
modified_base           20
                        mod_base = OTHER
                        note = 2'-O-methyl ribonucleoside
modified_base           21
                        mod_base = OTHER
                        note = 2'-O-methyl ribonucleoside
source                  1..21
                        mol_type = other RNA
                        organism = synthetic construct
SEQUENCE: 115
ttcgaagaca gttctagggt t                                        21

SEQ ID NO: 116          moltype = AA  length = 17
FEATURE                 Location/Qualifiers
REGION                  1..17
                        note = Description of Unknown:C105Y sequence
source                  1..17
                        mol_type = protein
                        organism = unidentified
SEQUENCE: 116
CSIPPEVKFN KPFVYLI                                             17
```

COMPOSITIONS AND METHODS OF TREATING MUSCLE DYSTROPHY

CROSS-REFERENCE

This application is a continuation of U.S. patent application Ser. No. 18/326,903, filed on May 31, 2023, issued as U.S. Pat. No. 12,427,202 on Sep. 30, 2025, which is a continuation of U.S. patent application Ser. No. 17/818,319, filed on Aug. 8, 2022, issued as U.S. Pat. No. 11,707,532 on Jul. 25, 2023, which is a continuation of U.S. patent application Ser. No. 17/214,525, filed on Mar. 26, 2021, issued as U.S. Pat. No. 11,446,387 on Sep. 20, 2022, which claims the benefit of U.S. Provisional Application No. 63/001,211 filed Mar. 27, 2020, each of which is incorporated herein by reference in its entirety.

SEQUENCE LISTING

The instant application contains a Sequence Listing which has been submitted electronically in XML format and is hereby incorporated by reference in its entirety. Said XML copy, created on Sep. 6, 2025, is named 45532-744_303_Replacement_SL.xml and is 345,978 bytes in size.

BACKGROUND OF THE DISCLOSURE

Gene suppression by RNA-induced gene silencing provides several levels of control: transcription inactivation, small interfering RNA (siRNA)-induced mRNA degradation, and siRNA-induced transcriptional attenuation. In some instances, RNA interference (RNAi) provides long lasting effect over multiple cell divisions. As such, RNAi represents a viable method useful for drug target validation, gene function analysis, pathway analysis, and disease therapeutics.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

Disclosed herein, in certain embodiments, are polynucleic acid molecules and pharmaceutical compositions for modulating a gene associated with muscle dystrophy (e.g., DM1).

In some embodiments, also described herein are methods of treating muscle atrophy with a polynucleic acid molecule or a polynucleic acid molecule conjugate disclosed herein.

Disclosed herein, in certain embodiments, is a polynucleic acid molecule conjugate comprising an anti-transferrin receptor antibody or antigen binding fragment thereof conjugated to a polynucleic acid molecule that hybridizes to a target sequence of DMPK. The polynucleic acid molecule having a sense strand having a sequence at least 80% identical to SEQ ID NO: 1, and an antisense strand having a sequence at least 80% identical to SEQ ID NO: 2. The polynucleic acid molecule conjugate mediates RNA interference against the DMPK.

In some embodiments, the anti-transferrin receptor antibody or antigen binding fragment thereof comprises a variable heavy chain (VH) region and a variable light chain (VL) region, wherein the VH region comprises HCDR1 sequence comprising SEQ ID NO: 17; HCDR2 sequence EINPI$X_1$GRSNYA$X_2$KFQG, wherein $X_1$ is selected from N or Q and $X_2$ is selected from Q or E (SEQ ID NO: 109); and HCDR3 sequence comprising SEQ ID NO: 19. In some embodiments, the VH region comprises HCDR1 sequence comprising SEQ ID NO: 17, HCDR2 sequence comprising one of SEQ ID NO: 18, SEQ ID NO: 20, SEQ ID NO: 21, and HCDR3 sequence comprising SEQ ID NO: 19. In some embodiments, the VL region comprises LCDR1 sequence RTSENIY$X_3$NLA (SEQ ID NO: 110), LCDR2 sequence A$X_4$TNLA$X_5$ (SEQ ID NO: 111), and LCDR3 sequence QHFWGTPLT$X_6$ (SEQ ID NO: 112), wherein $X_3$ is selected from N or S, $X_4$ is selected from A or G, $X_5$ is selected from D or E, and $X_6$ is present or absence, and if present, is F. In some embodiments, the VL region comprises LCDR1 sequence comprising SEQ ID NO: 22, LCDR2 sequence AATNLA$X_5$ (SEQ ID NO: 113), and LCDR3 sequence QHFWGTPLT$X_6$ (SEQ ID NO: 112), wherein $X_5$ is selected from D or E and $X_6$ is present or absence, and if present, is F. In some embodiments, the VL region comprises LCDR1 sequence comprising SEQ ID NO: 22 or SEQ ID NO: 27, LCDR2 sequence comprising SEQ ID NO: 23, SEQ ID NO: 25, or SEQ ID NO: 28, and LCDR3 sequence comprising SEQ ID NO: 24 or SEQ ID NO: 26. In some embodiments, the VH region comprises HCDR1 sequence comprising SEQ ID NO: 17, HCDR2 sequence comprising SEQ ID NO: 18, and HCDR3 sequence comprising SEQ ID NO: 19; and the VL region comprises LCDR1 sequence comprising SEQ ID NO: 22, LCDR2 sequence comprising SEQ ID NO: 23, and LCDR3 sequence comprising SEQ ID NO: 24. In some embodiments, the VH region comprises HCDR1 sequence comprising SEQ ID NO: 17, HCDR2 sequence comprising SEQ ID NO: 20, and HCDR3 sequence comprising SEQ ID NO: 19; and the VL region comprises LCDR1 sequence comprising SEQ ID NO: 22, LCDR2 sequence comprising SEQ ID NO: 23, and LCDR3 sequence comprising SEQ ID NO: 24. In some embodiments, the VH region comprises HCDR1 sequence comprising SEQ ID NO: 17, HCDR2 sequence comprising SEQ ID NO: 21, and HCDR3 sequence comprising SEQ ID NO: 19; and the VL region comprises LCDR1 sequence comprising SEQ ID NO: 22, LCDR2 sequence comprising SEQ ID NO: 25, and LCDR3 sequence comprising SEQ ID NO: 26. In some embodiments, the VH region comprises HCDR1 sequence comprising SEQ ID NO: 17, HCDR2 sequence comprising SEQ ID NO: 20, and HCDR3 sequence comprising SEQ ID NO: 19; and the VL region comprises LCDR1 sequence comprising SEQ ID NO: 27, LCDR2 sequence comprising SEQ ID NO: 28, and LCDR3 sequence comprising SEQ ID NO: 26. In some embodiments, the VH region comprises at least 80%, 85%, 90%, 95%, 99%, or 100% sequence identity to a sequence selected from SEQ ID NOs: 29-33. In some embodiments, the VL region comprises at least 80%, 85%, 90%, 95%, 99%, or 100% sequence identity to a sequence selected from SEQ ID NOs: 34-38. In some embodiments, the VH region comprises at least 80%, 85%, 90%, 95%, 99%, or 100% sequence identity to SEQ ID NO: 30, and wherein the VL region comprises at least 80%, 85%, 90%, 95%, 99%, or 100% sequence identity to SEQ ID NO: 34.

In some embodiments, the anti-transferrin receptor antibody comprises a humanized antibody, or antigen binding fragment thereof or a chimeric antibody or antigen binding fragment thereof, or a multi-specific antibody or antigen binding fragment thereof. In some embodiments, the anti-transferrin receptor antibody comprises an IgG-scFv, nanobody, BiTE™, diabody, DART, TandAb, scDiabody, scDiabody-CH3, triple body, mini-antibody, minibody, TriBi minibody, scFv-CH3 KIH, Fab-scFv-Fc KIH, Fab-scFv, scFv-CH-CL-scFv, F(ab')2, F(ab')2-scFv2. scFv-KIH, Fab-scFv-Fc, tetravalent HCAb, scDiabody-Fc, diabody-Fc, tandem scFv-Fc, or intrabody. In some embodiments, the anti-transferrin receptor antibody comprises an IgG1 framework. Alternatively, in some embodiments, the anti-transferrin receptor antibody comprises an IgG2 framework. In some instances, the IgG2 framework is IgG2b framework. Alternatively, in some embodiments, the anti-transferrin receptor antibody comprises IgG4 framework.

In some embodiments, the anti-transferrin receptor antibody further comprises at least one mutation in the Fc region. In some embodiments, the at least one mutation modulates effector function, or attenuates or eliminates Fc-γ receptor binding. In some embodiments, the at least one mutation is at residue position D265, N297, K322, L328, or P329, wherein the residue position is in reference to IgG1. In some embodiments, the Fc region comprises two or more, three or more, or four or more mutations. In some embodiments, the Fc region comprises mutations at L233 and L234, wherein the residues correspond to position 233 and 234 of SEQ ID NO: 39. In some embodiments, the Fc region comprises mutations at D265 and N297. In some embodiments, the Fc region comprises mutations at D265 and N297. In some embodiments, the anti-transferrin receptor antibody comprises a heavy chain (HC) sequence selected from SEQ ID NOs: 39-62 and a light chain (LC) sequence selected from SEQ ID NOs: 63-66. In some embodiments, the anti-transferrin receptor antibody specifically binds to human transferrin receptor (TfR).

In some embodiments, the sense strand and the antisense strand each independently comprises at least one 2' modified nucleotide, at least one modified internucleotide linkage, or at least one inverted abasic moiety. In some embodiments, the sense strand comprises a 2'-O-methyl modified nucleotide at the 5'-end. Alternatively and/or additionally, the sense strand comprises at least two consecutive 2'-O-methyl modified nucleotides at the 5'-end. Alternatively and/or additionally, the sense strand comprises at least three, four, five, or six consecutive 2'-O-methyl modified nucleotides at the 5'-end. Alternatively and/or additionally, the sense strand comprises six consecutive 2'-O-methyl modified nucleotides at the 5'-end. Alternatively and/or additionally, the sense strand comprises at least one 2'-F modified nucleotides. Alternatively and/or additionally, the sense strand comprises at least two, at least three 2'-F modified nucleotides. Alternatively and/or additionally, the sense strand comprises at least two, at least three consecutive 2'-F modified nucleotides. Alternatively and/or additionally, the sense strand comprises a 2'-O-methyl modified nucleotide at the 3'-end. Alternatively and/or additionally, the sense strand comprises at least two consecutive 2'-O-methyl modified nucleotides at the 3'-end. Alternatively and/or additionally, the sense strand comprises at least three, four, five, six, seven, eight, nine, or ten consecutive 2'-O-methyl modified nucleotides at the 3'-end. Alternatively and/or additionally, the sense strand comprises ten consecutive 2'-O-methyl modified nucleotides at the 3'-end. Alternatively and/or additionally, the sense strand comprises at least two phosphorothioate internucleotide linkages. Alternatively and/or additionally, the sense strand has a sequence of SEQ ID NO: 3, 5, 7, 9, 11, 13 or 15.

In some embodiments, the antisense strand comprises a 2'-O-methyl modified nucleotide at the 5'-end. Alternatively and/or additionally, the antisense strand comprises a 2'-O-methyl modified nucleotide at the 3'-end. Alternatively and/or additionally, the antisense strand comprises at least two, at least three, at least four, at least five consecutive 2'-O-methyl modified nucleotide at the 3'-end. Alternatively and/or additionally, the antisense strand comprises five consecutive 2'-O-methyl modified nucleotide at the 3'-end. Alternatively and/or additionally, the antisense strand comprises at least one, at least two, at least three, at least four 2'-F modified nucleotides. Alternatively and/or additionally, the antisense strand comprises four 2'-F modified nucleotides, wherein any two of the four 2'-F modified nucleotides are not consecutive. Alternatively and/or additionally, the antisense strand comprises two overhang nucleotides at the 3'-end. Alternatively and/or additionally, the antisense strand comprises at least two, at least three phosphorothioate internucleotide linkages. Alternatively and/or additionally, the antisense strand has a sequence of SEQ ID NO: 4, 6, 8, 10, 12, 14, or 16.

In some embodiments, the polynucleic acid molecule conjugate comprises a linker connecting anti-transferrin receptor antibody or antigen binding fragment thereof to the polynucleic acid molecule. In some embodiments, the linker is C6 linker. In some embodiments, the C6 linker is a 6-Amino-1-hexanol linker. In some embodiments, the linker is a homobifunctional linker or heterobifunctional linker, a maleimide group, a dipeptide moiety, a benzoic acid group, or its derivative thereof. In some embodiments, the linker comprises 4-(N-maleimidomethyl)cyclohexane-1-amidate (SMCC). In some embodiments, the linker is coupled to the 5'-end of the sense strand. In some embodiments, the polynucleic acid molecule is conjugated to a cysteine residue of the anti-transferrin receptor antibody or antigen binding fragment thereof. In some embodiments, the cysteine residue is in the Fc domain of the anti-transferrin receptor antibody or antigen binding fragment thereof. In some embodiments, a ratio between the polynucleic acid molecule and the anti-transferrin receptor antibody or antigen binding fragment thereof is about 1:1, 2:1, 3:1, or 4:1.

In some embodiments, the polynucleic acid moiety mediates RNA interference against the human DMPK gene modulates muscle atrophy in a subject. In some embodiments, the RNA interference comprises reducing expression of the mRNA transcript of DMPK gene at least 50%, at least 60%, or at least 70% compared to a quantity of the mRNA transcript of DMPK gene in a cell affected by a muscle dystrophy. In some embodiments, the muscle dystrophy is myotonic dystrophy type 1 (DM1).

Disclosed herein, in certain embodiments, is a polynucleic acid molecule conjugate comprising an anti-transferrin receptor antibody or antigen binding fragment thereof conjugated to a polynucleic acid molecule that hybridizes to a target sequence of DMPK. The polynucleic acid molecule having a sense strand having a sequence of SEQ ID NO: 3, 5, 7, 9, 11, 13, or 15 and an antisense strand having a sequence of SEQ ID NO: 4, 6, 8, 10, 12, 14, or 16, and the anti-transferrin receptor antibody or antigen binding fragment thereof comprises a variable heavy chain (VH) region and a variable light chain (VL) region, wherein the VH region comprises HCDR1 sequence comprising SEQ ID NO: 17, HCDR2 sequence comprising SEQ ID NO: 20, and HCDR3 sequence comprising SEQ ID NO: 19; and the VL region comprises LCDR1 sequence comprising SEQ ID NO: 22, LCDR2 sequence comprising SEQ ID NO: 23, and LCDR3 sequence comprising SEQ ID NO: 24, and the anti-transferrin receptor antibody or antigen binding fragment thereof and the polynucleic acid molecule is conjugated via a linker comprising 4-(N-maleimidomethyl) cyclohexane-1-amidate (SMCC).

Disclosed herein, in certain embodiments, is a polynucleic acid molecule conjugate comprising an anti-transferrin receptor antibody or antigen binding fragment thereof conjugated to a polynucleic acid molecule that hybridizes to a target sequence of DMPK. The polynucleic acid molecule having a sense strand having a sequence of SEQ ID NO: 3, 5, 7, 9, 11, 13, or 15 and an antisense strand having a sequence of SEQ ID NO: 4, 6, 8, 10, 12, 14, or 16, and the anti-transferrin receptor antibody or antigen binding fragment thereof comprises a variable heavy chain (VH) region and a variable light chain (VL) region, wherein the VH region comprises at least 80%, 85%, 90%, 95%, 99%, or 100% sequence identity to SEQ ID NO: 30, and wherein the VL region comprises at least 80%, 85%, 90%, 95%, 99%, or 100% sequence identity to SEQ ID NO: 34, and the anti-transferrin receptor antibody or antigen binding fragment thereof and the polynucleic acid molecule is conjugated via a maleimide linker.

Disclosed herein, in certain embodiments, is a polynucleic acid molecule conjugate comprising an anti-transferrin receptor antibody or antigen binding fragment thereof conjugated to a polynucleic acid molecule that hybridizes to a target sequence of DMPK. The polynucleic acid molecule having a sense strand having a sequence of SEQ ID NO: 1 and an antisense strand having a sequence of SEQ ID NO: 2, the sense strand comprises at least three, four, five, or six consecutive 2'-O-methyl modified nucleotides at the 5'-end and at least two, at least three 2'-F modified nucleotides, the anti-transferrin receptor antibody or antigen binding fragment thereof comprises a variable heavy chain (VH) region and a variable light chain (VL) region, wherein the VH region comprises at least 80%, 85%, 90%, 95%, 99%, or 100% sequence identity to SEQ ID NO: 30, and wherein the VL region comprises at least 80%, 85%, 90%, 95%, 99%, or 100% sequence identity to SEQ ID NO: 34, and the anti-transferrin receptor antibody or antigen binding fragment thereof and the polynucleic acid molecule is conjugated via a maleimide linker.

Disclosed herein, in certain embodiments, is a polynucleic acid molecule conjugate comprising an anti-transferrin receptor antibody or antigen binding fragment thereof conjugated to a polynucleic acid molecule that hybridizes to a target sequence of DMPK. The polynucleic acid molecule having a sense strand having a sequence of SEQ ID NO: 1 and an antisense strand having a sequence of SEQ ID NO: 2, and the antisense strand comprises at least two, at least three, at least four, at least five consecutive 2'-O-methyl modified nucleotide at the 3'-end, and at least one, at least two, at least three, at least four 2'-F modified nucleotides, and the anti-transferrin receptor antibody or antigen binding fragment thereof comprises a variable heavy chain (VH) region and a variable light chain (VL) region, wherein the VH region comprises HCDR1 sequence comprising SEQ ID NO: 17, HCDR2 sequence comprising SEQ ID NO: 20, and HCDR3 sequence comprising SEQ ID NO: 19; and the VL region comprises LCDR1 sequence comprising SEQ ID NO: 22, LCDR2 sequence comprising SEQ ID NO: 23, and LCDR3 sequence comprising SEQ ID NO: 24, and the anti-transferrin receptor antibody or antigen binding fragment thereof and the polynucleic acid molecule is conjugated via a maleimide linker.

Disclosed herein, in certain embodiments, is a polynucleic acid molecule conjugate comprising an anti-transferrin receptor antibody or antigen binding fragment thereof conjugated to a polynucleic acid molecule that hybridizes to a target sequence of DMPK. The polynucleic acid molecule having a sense strand having a sequence of SEQ ID NO: 1 and an antisense strand having a sequence of SEQ ID NO: 2, and the antisense strand comprises 2'-O-methyl modified nucleotides at the 5'-end and at the 3'-end, and the anti-transferrin receptor antibody or antigen binding fragment thereof comprises a variable heavy chain (VH) region and a variable light chain (VL) region, wherein the VH region comprises HCDR1 sequence comprising SEQ ID NO: 17, HCDR2 sequence comprising SEQ ID NO: 18, and HCDR3 sequence comprising SEQ ID NO: 19; and the VL region comprises LCDR1 sequence comprising SEQ ID NO: 22, LCDR2 sequence comprising SEQ ID NO: 23, and LCDR3 sequence comprising SEQ ID NO: 24, and the anti-transferrin receptor antibody or antigen binding fragment thereof and the polynucleic acid molecule is conjugated via a maleimide linker.

Disclosed herein, in certain embodiments, is a polynucleic acid molecule conjugate comprising an anti-transferrin receptor antibody or antigen binding fragment thereof conjugated to a polynucleic acid molecule that hybridizes to a target sequence of DMPK. The polynucleic acid molecule having a sense strand having a sequence of SEQ ID NO: 1 and an antisense strand having a sequence of SEQ ID NO: 2, and the antisense strand comprises at least five consecutive 2'-O-methyl modified nucleotide at the 3'-end and four 2'-F modified nucleotides, wherein any two of the four 2'-F modified nucleotides are not consecutive, and the anti-transferrin receptor antibody or antigen binding fragment thereof comprises a variable heavy chain (VH) region and a variable light chain (VL) region, and the VH region comprises at least 80%, 85%, 90%, 95%, 99%, or 100% sequence identity to SEQ ID NO: 30, and wherein the VL region comprises at least 80%, 85%, 90%, 95%, 99%, or 100% sequence identity to SEQ ID NO: 34, and the anti-transferrin receptor antibody or antigen binding fragment thereof and the polynucleic acid molecule is conjugated via a 6-Amino-1-hexanol linker.

Disclosed herein, in certain embodiments, is a polynucleic acid molecule conjugate comprising an anti-transferrin receptor antibody or antigen binding fragment thereof conjugated to a polynucleic acid molecule that hybridizes to a target sequence of DMPK. The polynucleic acid molecule having a sense strand having a sequence of SEQ ID NO: 1 and an antisense strand having a sequence of SEQ ID NO: 2, and the antisense strand comprises at least five consecutive 2'-O-methyl modified nucleotide at the 3'-end and four 2'-F modified nucleotides, wherein any two of the four 2'-F modified nucleotides are not consecutive, and the anti-transferrin receptor antibody or antigen binding fragment thereof comprises a variable heavy chain (VH) region and a variable light chain (VL) region, and the VH region comprises at least 80%, 85%, 90%, 95%, 99%, or 100% sequence identity to SEQ ID NO: 30, and wherein the VL region comprises at least 80%, 85%, 90%, 95%, 99%, or 100% sequence identity to SEQ ID NO: 34, and the anti-transferrin receptor antibody or antigen binding fragment thereof and the polynucleic acid molecule is conjugated via a 6-Amino-1-hexanol linker.

Disclosed herein, in certain embodiments, is a pharmaceutical composition comprising a polynucleic acid molecule conjugate as described herein and a pharmaceutically acceptable excipient. In some embodiments, the pharmaceutical composition is formulated as a nanoparticle formulation. In some embodiments, the pharmaceutical composition is formulated for parenteral, oral, intranasal, buccal, rectal, or transdermal administration.

Disclosed herein, in certain embodiments, is a method for treating muscular dystrophy in a subject in need thereof by providing a polynucleic acid conjugate or pharmaceutical compositions as described herein, and administering the polynucleic acid conjugate to the subject in need thereof to treat the muscular dystrophy, wherein the polynucleic acid conjugate reduces a quantity of the mRNA transcript of human DMPK. In some embodiments, the polynucleic acid moiety mediates RNA interference against the human DMPK modulates muscle atrophy in a subject. In some embodiments, the muscular dystrophy is myotonic dystrophy type 1 (DM1).

Disclosed herein, in certain embodiments, is use of a polynucleic acid conjugate or pharmaceutical compositions as described herein for treating in a subject diagnosed with or suspected to have myotonic dystrophy type 1 (DM1) or for manufacturing a medicament for treating in a subject diagnosed with or suspected to have myotonic dystrophy type 1 (DM1). Disclosed herein, in certain embodiments, is a kit comprising a polynucleic acid conjugate or pharmaceutical compositions as described herein.

DETAILED DESCRIPTION OF THE DISCLOSURE

Figure 1:
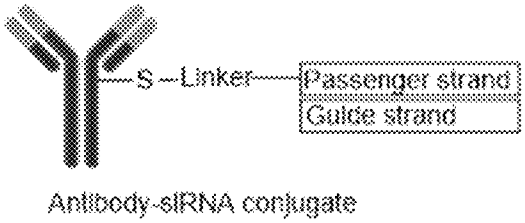
FIG. 1 illustrates a schematic of antibody-siRNA conjugate.
Figure 2:
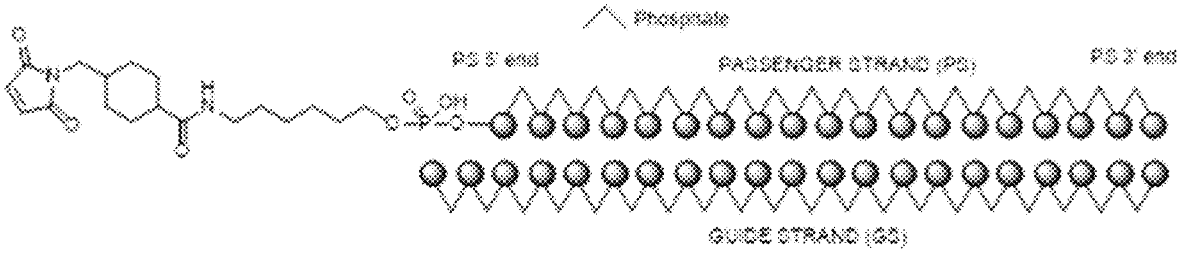
FIG. 2 illustrates a schematic structure of DMPK siRNA.

DM1 is a rare, monogenic, autosomal dominant, repeat expansion disorder that affects approximately 1 in 8,000 individuals in the US based on clinical ascertainment. However, a recent genetic based study estimated the prevalence of DM1 in the US to be 1 in 2,532 individuals. DM1 is caused by an expansion of the CTG triplet repeat found in the 3' non-coding region of the dystrophia myotonica protein kinase (DMPK) gene. The expansion ranges from <35 in healthy subjects to many thousands in DM1 patients. When the mutant DMPK gene is translated into mRNA, the self-complementary CUG repeats induce the formation of large hairpin loops and entrap the DMPK mRNA in the nucleus, imparting a toxic-gain-of function. The toxicity is not due to the translation of the mRNA into a toxic protein but rather to the presence of high concentrations of CUG repeats in the nucleus which act as a trap for a critical CUG binding protein, muscle blindlike protein 1 (MBNL1). Through its binding to the nuclear retained DMPK CUG repeats, MBNL1 becomes sequestered in the nucleus and is unable to perform its normal function of guiding mRNA processing. As a result, multiple mRNAs that encode key proteins are mis-processed. The resulting atypical proteins that are translated from these mis-spliced mRNAs, are the ultimate cause of the phenotypic changes' characteristic of the disease.

Nucleic acid (e.g., RNAi) therapy is a targeted therapy with high selectivity and specificity. However, in some instances, nucleic acid therapy is also hindered by poor intracellular uptake, limited blood stability and non-specific immune stimulation. To address these issues, various modifications of the nucleic acid composition are explored, such as for example, novel linkers for better stabilizing and/or lower toxicity, optimization of binding moiety for increased target specificity and/or target delivery, and nucleic acid polymer modifications for increased stability and/or reduced off-target effect.

In some embodiments, the arrangement or order of the different components that make-up the nucleic acid composition further effects intracellular uptake, stability, toxicity, efficacy, and/or non-specific immune stimulation. For example, if the nucleic acid component includes a binding moiety, a polymer, and a polynucleic acid molecule (or polynucleotide), the order or arrangement of the binding moiety, the polymer, and/or the polynucleic acid molecule (or polynucleotide) (e.g., binding moiety-polynucleic acid molecule-polymer, binding moiety-polymer-polynucleic acid molecule, or polymer-binding moiety-polynucleic acid molecule) further effects intracellular uptake, stability, toxicity, efficacy, and/or non-specific immune stimulation.

In some embodiments, described herein include polynucleic acid molecules and polynucleic acid molecule conjugates for the treatment of muscular dystrophy. In some instances, the polynucleic acid molecule conjugates described herein enhance intracellular uptake, stability, and/or efficacy. In some cases, the polynucleic acid molecule conjugates comprise an anti-transferrin receptor antibody or antigen binding fragment thereof conjugated to a polynucleic acid molecule that hybridizes to a target sequence of DMPK. In some cases, the polynucleic acid molecule conjugates comprise a molecule of Formula (I): A-$X_1$-B.

Additional embodiments described herein include methods of treating muscular dystrophy, comprising administering to a subject a polynucleic acid molecule or a polynucleic acid molecule conjugate described herein.

Polynucleic Acid Molecules

In certain embodiments, a polynucleic acid molecule hybridizes to a target sequence of an muscular dystrophy-related gene. Preferably, among muscle dystrophy-related genes, a polynucleic acid molecule described herein hybridizes to a target sequence of myotonic dystrophy protein kinase gene (DMPK, also referred as DM, DM1, DM1PK, DMK, MDPK, MT-PK, Dm15, dystrophia myotonica protein kinase, DM1 protein kinase gene).

In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NO: 1. In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NO: 2. In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NO: 3, 5, 7, 9, 11, 13, or 15. In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NO: 4, 6, 8, 10, 12, 14, or 16.

In some embodiments, the polynucleic acid molecule comprises a first polynucleotide and a second polynucleotide. In some instances, the first polynucleotide comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NO: 1. In some cases, the second polynucleotide comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NO: 2. In some cases, the polynucleic acid molecule comprises a first polynucleotide and a second polynucleotide. In some instances, the first polynucleotide comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NO: 3, 5, 7, 9, 11, 13, or 15. In some cases, the second polynucleotide comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NO: 4, 6, 8, 10, 12, 14, or 16.

In some embodiments, the polynucleic acid molecule comprises a sense strand (e.g., a passenger strand) and an antisense strand (e.g., a guide strand). In some instances, the sense strand (e.g., the passenger strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NO: 1. In some instances, the antisense strand (e.g., the guide strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NO: 2. In some embodiments, the polynucleic acid molecule comprises a sense strand (e.g., a passenger strand) and an antisense strand (e.g., a guide strand). In some instances, the sense strand (e.g., the passenger strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NO: 3, 5, 7, 9, 11, 13, or 15. In some instances, the antisense strand (e.g., the guide strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NO: 4, 6, 8, 10, 12, 14, or 16. Table 1 presents nucleic acid sequences and modified sequences of SEQ ID NOs: 1-16.

TABLE 1

| SEQ ID NO | sense/passenger_seq (5'-3') | SEQ ID NO | antisense/guide_seq (5'-3') |
|---|---|---|---|
| 1 | 5'-CCCUAGAACUGUCUUCGAA-3' | 2 | 5'-UUCGAAGACAGUUCUAGGGUU-3' |
| 3 | 5'-mC-(s)-mC-(s)-mC-mU-mA-mG-fA-fA-fC-mU-mG-mU-mC-mU-mU-mC-mG-(s)-mA-(s)-mA-3' | 4 | 5'-mU-(s)-fU-(s)-mC-mG-mA-fA-mG-mA-mC-mA-mG-mU-mU-fC-mU-fA-mG-mG-mG-(s)-mU-(s)-mU-3' |
| 5 | 5'-fC-(s)-mC-(s)-fC-mU-mA-mG-fA-mA-mC-fU-mG-fU-mC-fU-mU-mC-mG-(s)-mA-(s)-mA-3' | 6 | 5'-U-(s)-U-mC-(s)-mG-fA-fA-mG-mA-mC-fA-fG-mU-mU-fC-(s)-mU-fA-mG-mG-mG-(s)-mU-(s)-mU-3' |
| 7 | 5'-C-(s)-mC-(s)-fC-fU-mA-mG-fA-mA-mC-mU-mG-mU-mC-mU-mU-fC-fG-(s)-mA-(s)-mA-3' | 8 | 5'-U-(s)-fU-(s)-mC-mG-mA-fA-mG-mA-mC-mA-mG-mU-mU-fC-mU-fA-mG-mG-mG-(s)-mU-(s)-mU-3' |
| 9 | 5'-mC-(s)-fC-(s)-fC-mU-mA-mG-fA-mA-mC-mU-mG-mU-mC-mU-mU-mC-mG-(s)-fA-(s)-A-3' | 10 | 5'-mU-(s)-fU-(s)-mC-mG-mA-fA-mG-mA-mC-mA-mG-fU-mU-fC-fU-fA-mG-mG-mG-(s)-fU-(s)-mU-3' |
| 11 | 5'-C-(s)-C-(s)-fC-fU-mA-mG-mA-mA-mC-mU-mG-mU-fC-fU-mU-mC-mG-(s)-mA-(s)-mA-3' | 12 | 5'-mU-(s)-fU-(s)-mC-mG-mA-fA-mG-mA-mC-fA-mG-mU-mU-fC-mU-fA-mG-mG-mG-(s)-mU-(s)-fU-3' |
| 13 | 5'-C-fC-(s)-fC-mU-(s)-mA-(s)-mG-fA-mA-C-U-mG-mU-mC-mU-mU-mC-G-(s)-A-(s)-A-3' | 14 | 5'-mU-(s)-fU-(s)-mC-mG-mA-fA-mG-mA-mC-mA-(s)-mG-U-mU-fC-fU-fA-mG-mG-mG-(s)-fU-(s)-mU-3' |
| 15 | 5'-mC-(s)-mC-(s)-mC-mU-mA-mG-mA-mA-mC-mU-mG-(s)-U-fC-fU-mU-mC-mG-(s)-A-(s)-mA-3' | 16 | 5'-mU-(s)-mU-(s)-mC-mG-A-fA-mG-mA-mC-fA-mG-U-mU-fC-U-fA-mG-mG-mG-(s)-mU-fU-3' |

mX = 2'-O-methyl ribonucleoside fX = 2'-fluoro nucleoside

-(s)- = phosphorothioate internucleotide linkage

- = phosphodiester internucleotide linkages

In some embodiments, the polynucleic acid molecule described herein comprises RNA or DNA or PMOs. In some cases, the polynucleic acid molecule comprises RNA. In some instances, RNA comprises short interfering RNA (siRNA), short hairpin RNA (shRNA), microRNA (miRNA), single-stranded RNA (ssRNA), double-stranded RNA (dsRNA), transfer RNA (tRNA), ribosomal RNA (rRNA), or heterogeneous nuclear RNA (hnRNA). In some instances, RNA comprises shRNA. In some instances, RNA comprises miRNA. In some instances, RNA comprises dsRNA. In some instances, RNA comprises tRNA. In some instances, RNA comprises rRNA. In some instances, RNA comprises hnRNA. In some instances, the RNA comprises siRNA. In some instances, the polynucleic acid molecule comprises siRNA.

In some embodiments, the polynucleic acid molecule is from about 8 to about 50 nucleotides in length. In some embodiments, the polynucleic acid molecule is from about 10 to about 50 nucleotides in length. In some instances, the polynucleic acid molecule is from about 10 to about 30, from about 15 to about 30, from about 18 to about 25, form about 18 to about 24, from about 19 to about 23, or from about 20 to about 22 nucleotides in length.

In some embodiments, the polynucleic acid molecule is about 50 nucleotides in length. In some instances, the polynucleic acid molecule is about 45 nucleotides in length. In some instances, the polynucleic acid molecule is about 40 nucleotides in length. In some instances, the polynucleic acid molecule is about 35 nucleotides in length. In some instances, the polynucleic acid molecule is about 30 nucleotides in length. In some instances, the polynucleic acid molecule is about 25 nucleotides in length. In some instances, the polynucleic acid molecule is about 20 nucleotides in length. In some instances, the polynucleic acid molecule is about 19 nucleotides in length. In some instances, the polynucleic acid molecule is about 18 nucleotides in length. In some instances, the polynucleic acid molecule is about 17 nucleotides in length. In some instances, the polynucleic acid molecule is about 16 nucleotides in length. In some instances, the polynucleic acid molecule is about 15 nucleotides in length. In some instances, the polynucleic acid molecule is about 14 nucleotides in length. In some instances, the polynucleic acid molecule is about 13 nucleotides in length. In some instances, the polynucleic acid molecule is about 12 nucleotides in length. In some instances, the polynucleic acid molecule is about 11 nucleotides in length. In some instances, the polynucleic acid molecule is about 10 nucleotides in length. In some instances, the polynucleic acid molecule is about 8 nucleotides in length. In some instances, the polynucleic acid molecule is between about 8 and about 50 nucleotides in length. In some instances, the polynucleic acid molecule is between about 10 and about 50 nucleotides in length. In some instances, the polynucleic acid molecule is between about 10 and about 45 nucleotides in length. In some instances, the polynucleic acid molecule is between about 10 and about 40 nucleotides in length. In some instances, the polynucleic acid molecule is between about 10 and about 35 nucleotides in length. In some instances, the polynucleic acid molecule is between about 10 and about 30 nucleotides in length. In some instances, the polynucleic acid molecule is between about 10 and about 25 nucleotides in length. In some instances, the polynucleic acid molecule is between about 10 and about 20 nucleotides in length. In some instances, the polynucleic acid molecule is between about 15 and about 25 nucleotides in length. In some instances, the polynucleic acid molecule is between about 15 and about 30 nucleotides in length. In some instances, the polynucleic acid molecule is between about 12 and about 30 nucleotides in length.

In some embodiments, the polynucleic acid molecule comprises a first polynucleotide. In some instances, the polynucleic acid molecule comprises a second polynucleotide. In some instances, the polynucleic acid molecule comprises a first polynucleotide and a second polynucleotide. In some instances, the first polynucleotide is a sense strand or passenger strand. In some instances, the second polynucleotide is an antisense strand or guide strand.

In some embodiments, the polynucleic acid molecule is a first polynucleotide. In some embodiments, the first polynucleotide is from about 8 to about 50 nucleotides in length. In some embodiments, the first polynucleotide is from about 10 to about 50 nucleotides in length. In some instances, the first polynucleotide is from about 10 to about 30, from about 15 to about 30, from about 18 to about 25, form about 18 to about 24, from about 19 to about 23, or from about 20 to about 22 nucleotides in length.

In some instances, the first polynucleotide is about 50 nucleotides in length. In some instances, the first polynucleotide is about 45 nucleotides in length. In some instances, the first polynucleotide is about 40 nucleotides in length. In some instances, the first polynucleotide is about 35 nucleotides in length. In some instances, the first polynucleotide is about 30 nucleotides in length. In some instances, the first polynucleotide is about 25 nucleotides in length. In some instances, the first polynucleotide is about 20 nucleotides in length. In some instances, the first polynucleotide is about 19 nucleotides in length. In some instances, the first polynucleotide is about 18 nucleotides in length. In some instances, the first polynucleotide is about 17 nucleotides in length. In some instances, the first polynucleotide is about 16 nucleotides in length. In some instances, the first polynucleotide is about 15 nucleotides in length. In some instances, the first polynucleotide is about 14 nucleotides in length. In some instances, the first polynucleotide is about 13 nucleotides in length. In some instances, the first polynucleotide is about 12 nucleotides in length. In some instances, the first polynucleotide is about 11 nucleotides in length. In some instances, the first polynucleotide is about 10 nucleotides in length. In some instances, the first polynucleotide is about 8 nucleotides in length. In some instances, the first polynucleotide is between about 8 and about 50 nucleotides in length. In some instances, the first polynucleotide is between about 10 and about 50 nucleotides in length. In some instances, the first polynucleotide is between about 10 and about 45 nucleotides in length. In some instances, the first polynucleotide is between about 10 and about 40 nucleotides in length. In some instances, the first polynucleotide is between about 10 and about 35 nucleotides in length. In some instances, the first polynucleotide is between about 10 and about 30 nucleotides in length. In some instances, the first polynucleotide is between about 10 and about 25 nucleotides in length. In some instances, the first polynucleotide is between about 10 and about 20 nucleotides in length. In some instances, the first polynucleotide is between about 15 and about 25 nucleotides in length. In some instances, the first polynucleotide is between about 15 and about 30 nucleotides in length. In some instances, the first polynucleotide is between about 12 and about 30 nucleotides in length.

In some embodiments, the polynucleic acid molecule is a second polynucleotide. In some embodiments, the second polynucleotide is from about 8 to about 50 nucleotides in length. In some embodiments, the second polynucleotide is from about 10 to about 50 nucleotides in length. In some instances, the second polynucleotide is from about 10 to about 30, from about 15 to about 30, from about 18 to about 25, form about 18 to about 24, from about 19 to about 23, or from about 20 to about 22 nucleotides in length.

In some instances, the second polynucleotide is about 50 nucleotides in length. In some instances, the second polynucleotide is about 45 nucleotides in length. In some instances, the second polynucleotide is about 40 nucleotides in length. In some instances, the second polynucleotide is about 35 nucleotides in length. In some instances, the second polynucleotide is about 30 nucleotides in length. In some instances, the second polynucleotide is about 25 nucleotides in length. In some instances, the second polynucleotide is about 20 nucleotides in length. In some instances, the second polynucleotide is about 19 nucleotides in length. In some instances, the second polynucleotide is about 18 nucleotides in length. In some instances, the second polynucleotide is about 17 nucleotides in length. In some instances, the second polynucleotide is about 16 nucleotides in length. In some instances, the second polynucleotide is about 15 nucleotides in length. In some instances, the second polynucleotide is about 14 nucleotides in length. In some instances, the second polynucleotide is about 13 nucleotides in length. In some instances, the second polynucleotide is about 12 nucleotides in length. In some instances, the second polynucleotide is about 11 nucleotides in length. In some instances, the second polynucleotide is about 10 nucleotides in length. In some instances, the second polynucleotide is about 8 nucleotides in length. In some instances, the second polynucleotide is between about 8 and about 50 nucleotides in length. In some instances, the second polynucleotide is between about 10 and about 50 nucleotides in length. In some instances, the second polynucleotide is between about 10 and about 45 nucleotides in length. In some instances, the second polynucleotide is between about 10 and about 40 nucleotides in length. In some instances, the second polynucleotide is between about 10 and about 35 nucleotides in length. In some instances, the second polynucleotide is between about 10 and about 30 nucleotides in length. In some instances, the second polynucleotide is between about 10 and about 25 nucleotides in length. In some instances, the second polynucleotide is between about 10 and about 20 nucleotides in length. In some instances, the second polynucleotide is between about 15 and about 25 nucleotides in length. In some instances, the second polynucleotide is between about 15 and about 30 nucleotides in length. In some instances, the second polynucleotide is between about 12 and about 30 nucleotides in length.

In some embodiments, the polynucleic acid molecule comprises a first polynucleotide and a second polynucleotide. In some instances, the polynucleic acid molecule further comprises a blunt terminus, an overhang, or a combination thereof. In some instances, the blunt terminus is a 5' blunt terminus, a 3' blunt terminus, or both. In some cases, the overhang is a 5' overhang, 3' overhang, or both. In some cases, the overhang comprises 1, 2, 3, 4, 5, 6, 7, 8, 9, or 10 non-base pairing nucleotides. In some cases, the overhang comprises 1, 2, 3, 4, 5, or 6 non-base pairing nucleotides. In some cases, the overhang comprises 1, 2, 3, or 4 non-base pairing nucleotides. In some cases, the overhang comprises 1 non-base pairing nucleotide. In some cases, the overhang comprises 2 non-base pairing nucleotides. In some cases, the overhang comprises 3 non-base pairing nucleotides. In some cases, the overhang comprises 4 non-base pairing nucleotides. In some embodiments, the polynucleic acid molecule comprises a sense strand and an antisense strand, and the antisense strand includes two non-base pairing nucleotides as an overhang at the 3'-end while the sense strand has no overhang. Optionally, in such embodiments, the non-base pairing nucleotides have a sequence of TT, dTdT, or UU. In some embodiments, the polynucleic acid molecule comprises a sense strand and an antisense strand, and the sense strand has one or more nucleotides at the 5'-end that are complementary to the antisense sequence.

In some embodiments, the sequence of the polynucleic acid molecule is at least 40%, 50%, 55%, 60%, 65%, 70%, 75%, 80%, 85%, 90%, 95%, 98%, 99%, or 99.5% complementary to a target sequence described herein. In some embodiments, the sequence of the polynucleic acid molecule is at least 50% complementary to a target sequence described herein. In some embodiments, the sequence of the polynucleic acid molecule is at least 60% complementary to a target sequence described herein. In some embodiments, the sequence of the polynucleic acid molecule is at least 70% complementary to a target sequence described herein. In some embodiments, the sequence of the polynucleic acid molecule is at least 80% complementary to a target sequence described herein. In some embodiments, the sequence of the polynucleic acid molecule is at least 90% complementary to a target sequence described herein. In some embodiments, the sequence of the polynucleic acid molecule is at least 95% complementary to a target sequence described herein. In some embodiments, the sequence of the polynucleic acid molecule is at least 99% complementary to a target sequence described herein. In some instances, the sequence of the polynucleic acid molecule is 100% complementary to a target sequence described herein.

In some embodiments, the sequence of the polynucleic acid molecule has 5 or less mismatches to a target sequence described herein. In some embodiments, the sequence of the polynucleic acid molecule has 4 or less mismatches to a target sequence described herein. In some instances, the sequence of the polynucleic acid molecule has 3 or less mismatches to a target sequence described herein. In some cases, the sequence of the polynucleic acid molecule has 2 or less mismatches to a target sequence described herein. In some cases, the sequence of the polynucleic acid molecule has 1 or less mismatches to a target sequence described herein.

In some embodiments, the specificity of the polynucleic acid molecule that hybridizes to a target sequence described herein is a 95%, 98%, 99%, 99.5% or 100% sequence complementarity of the polynucleic acid molecule to a target sequence. In some instances, the hybridization is a high stringent hybridization condition.

In some embodiments, the polynucleic acid molecule has reduced off-target effect. In some instances, "off-target" or "off-target effects" refer to any instance in which a polynucleic acid polymer directed against a given target causes an unintended effect by interacting either directly or indirectly with another mRNA sequence, a DNA sequence or a cellular protein or other moiety. In some instances, an "off-target effect" occurs when there is a simultaneous degradation of other transcripts due to partial homology or complementarity between that other transcript and the sense and/or antisense strand of the polynucleic acid molecule.

In some embodiments, the polynucleic acid molecule comprises natural or synthetic or artificial nucleotide analogues or bases. In some cases, the polynucleic acid molecule comprises combinations of DNA, RNA and/or nucleotide analogues. In some instances, the synthetic or artificial nucleotide analogues or bases comprise modifications at one or more of ribose moiety, phosphate moiety, nucleoside moiety, or a combination thereof.

In some embodiments, nucleotide analogues or artificial nucleotide base comprise a nucleic acid with a modification at a 2' hydroxyl group of the ribose moiety. In some instances, the modification includes an H, OR, R, halo, SH, SR, NH2, NHR, NR2, or CN, wherein R is an alkyl moiety. Exemplary alkyl moiety includes, but is not limited to halogens, sulfurs, thiols, thioethers, thioesters, amines (primary, secondary, or tertiary), amides, ethers, esters, alcohols and oxygen. In some instances, the alkyl moiety further comprises a modification. In some instances, the modification comprises an azo group, a keto group, an aldehyde group, a carboxyl group, a nitro group, a nitroso, group, a nitrile group, a heterocycle (e.g., imidazole, hydrazino or hydroxylamino) group, an isocyanate or cyanate group, or a sulfur containing group (e.g., sulfoxide, sulfone, sulfide, and disulfide). In some instances, the alkyl moiety further comprises a hetero substitution. In some instances, the carbon of the heterocyclic group is substituted by a nitrogen, oxygen or sulfur. In some instances, the heterocyclic substitution includes but is not limited to, morpholino, imidazole, and pyrrolidino.

In some instances, the modification at the 2' hydroxyl group is a 2'-O-methyl modification or a 2'-O-methoxyethyl (2'-O-MOE) modification. In some cases, the 2'-O-methyl modification adds a methyl group to the 2' hydroxyl group of the ribose moiety whereas the 2'O-methoxyethyl modification adds a methoxyethyl group to the 2' hydroxyl group of the ribose moiety. Exemplary chemical structures of a 2'-O-methyl modification of an adenosine molecule and 2'O-methoxyethyl modification of an uridine are illustrated below.

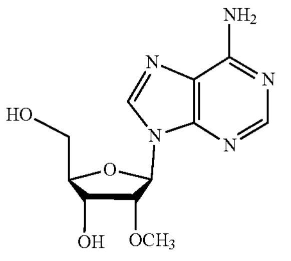

2′-O-methyl-adenosine

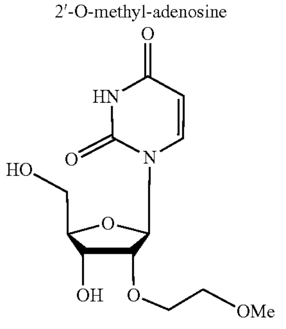

2′-O-methoxyethyl uridine

In some instances, the modification at the 2' hydroxyl group is a 2'-O-aminopropyl modification in which an extended amine group comprising a propyl linker binds the amine group to the 2' oxygen. In some instances, this modification neutralizes the phosphate derived overall negative charge of the oligonucleotide molecule by introducing one positive charge from the amine group per sugar and thereby improves cellular uptake properties due to its zwitterionic properties. An exemplary chemical structure of a 2'-O-aminopropyl nucleoside phosphoramidite is illustrated below.

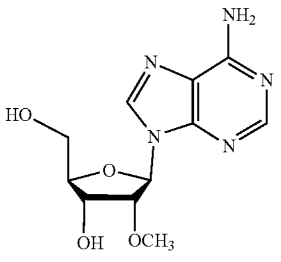

2′-O-methyl-adenosine

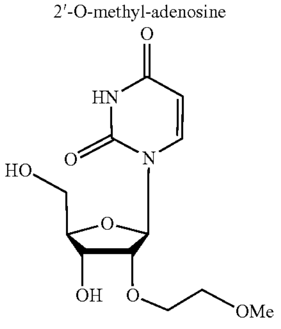

2′-O-methoxyethyl uridine

In some instances, the modification at the 2' hydroxyl group is a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of LNA are illustrated below. The representation shown to the left highlights the chemical connectivities of an LNA monomer. The representation shown to the right highlights the locked 3'-endo ($^3E$) conformation of the furanose ring of an LNA monomer.

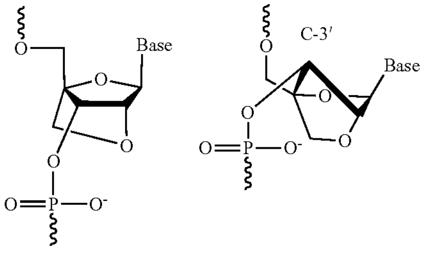

LNA (Locked Nucleic Acids)

In some instances, the modification at the 2' hydroxyl group comprises ethylene nucleic acids (ENA) such as for example 2'-4'-ethylene-bridged nucleic acid, which locks the sugar conformation into a C3'-endo sugar puckering conformation. ENA are part of the bridged nucleic acids class of modified nucleic acids that also comprises LNA. Exemplary chemical structures of the ENA and bridged nucleic acids are illustrated below.

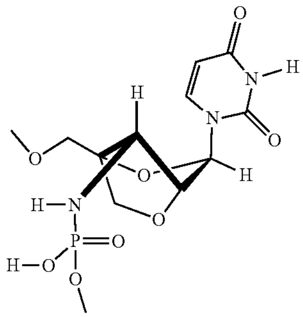

3′-amino-2′,4′-BNA

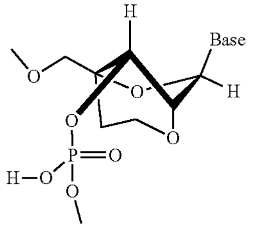

2′,4′-ENA

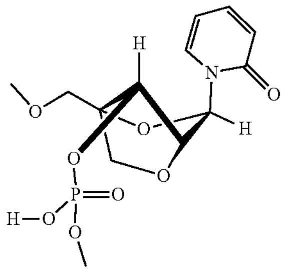

2′,4′-BNA-2-pyridone

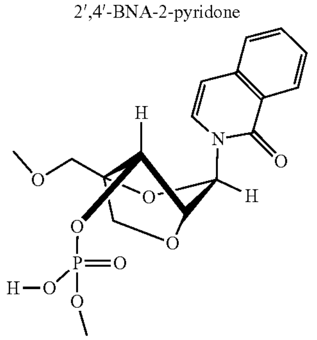

2′,4′-BNA-1-isoquinolone

In some embodiments, additional modifications at the 2' hydroxyl group include 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O-N-methylacetamido (2'-O-NMA).

In some embodiments, nucleotide analogues comprise modified bases such as, but not limited to, 5-propynyluridine, 5-propynylcytidine, 6-methyladenine, 6-methylguanine, N, N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O-and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2, 4, 6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties, in some cases are or be based on, mannoses, arabinoses, glucopyranoses, galactopyranoses, 4'-thioribose, and other sugars, heterocycles, or carbocycles. The term nucleotide also includes what are known in the art as universal bases. By way of example, universal bases include but are not limited to 3-nitropyrrole, 5-nitroindole, or nebularine.

In some embodiments, nucleotide analogues further comprise morpholinos, peptide nucleic acids (PNAs), methylphosphonate nucleotides, thiolphosphonate nucleotides, 2'-fluoro N3-P5'-phosphoramidites, 1', 5'-anhydrohexitol nucleic acids (HNAs), or a combination thereof. Morpholino or phosphorodiamidate morpholino oligo (PMO) comprises synthetic molecules whose structure mimics natural nucleic acid structure by deviates from the normal sugar and phosphate structures. In some instances, the five member ribose ring is substituted with a six member morpholino ring containing four carbons, one nitrogen and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucleotides.

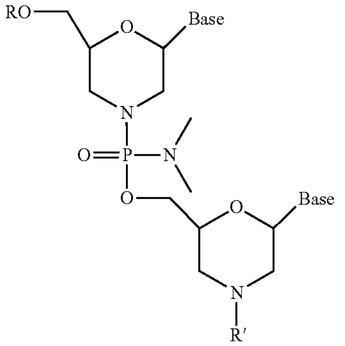

Morpholino

In some embodiments, peptide nucleic acid (PNA) does not contain sugar ring or phosphate linkage and the bases are attached and appropriately spaced by oligoglycine-like molecules, therefore, eliminating a backbone charge.

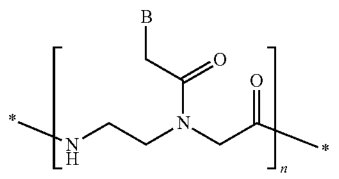

PNA

In some embodiments, one or more modifications optionally occur at the internucleotide linkage. In some instances, modified internucleotide linkage include, but is not limited to, phosphorothioates, phosphorodithioates, methylphosphonates, 5'-alkylenephosphonates, 5'-methylphosphonate, 3'-alkylene phosphonates, borontrifluoridates, borano phosphate esters and selenophosphates of 3'-5'linkage or 2'-5'linkage, phosphotriesters, thionoalkylphosphotriesters, hydrogen phosphonate linkages, alkyl phosphonates, alkylphosphonothioates, arylphosphonothioates, phosphoroselenoates, phosphorodiselenoates, phosphinates, phosphoramidates, 3'-alkylphosphoramidates, aminoalkylphosphoramidates, thionophosphoramidates, phosphoropiperazidates, phosphoroanilothioates, phosphoroanilidates, ketones, sulfones, sulfonamides, carbonates, carbamates, methylenehydrazos, methylenedimethylhydrazos, formacetals, thioformacetals, oximes, methyleneiminos, methylenemethyliminos, thioamidates, linkages with riboacetyl groups, aminoethyl glycine, silyl or siloxane linkages, alkyl or cycloalkyl linkages with or without heteroatoms of, for example, 1 to 10 carbons that are saturated or unsaturated and/or substituted and/or contain heteroatoms, linkages with morpholino structures, amides, polyamides wherein the bases are attached to the aza nitrogens of the backbone directly or indirectly, and combinations thereof. Phosphorothioate antisense oligonucleotides (PS ASO) are antisense oligonucleotides comprising a phosphorothioate linkage. An exemplary PS ASO is illustrated below.

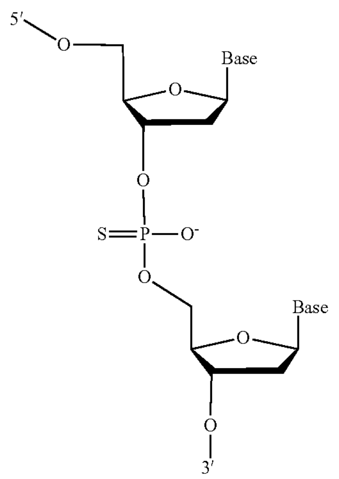

In some instances, the modification is a methyl or thiol modification such as methylphosphonate or thiolphosphonate modification. Exemplary thiolphosphonate nucleotide (left) and methylphosphonate nucleotide (right) are illustrated below.

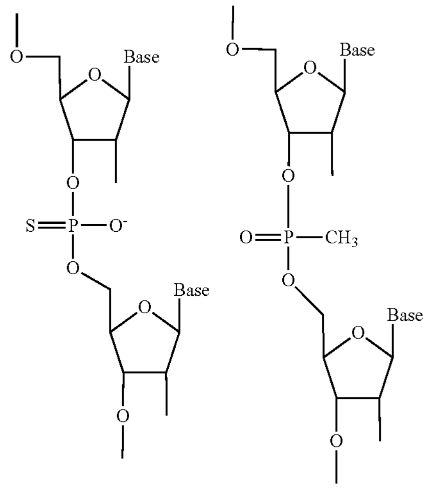

In some instances, a modified nucleotide includes, but is not limited to, 2'-fluoro N3-P5'-phosphoramidites illustrated as:

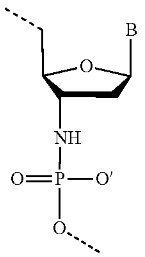

N3'-P5'
Phosphoroamidate

In some instances, a modified nucleotide includes, but is not limited to, hexitol nucleic acid (or 1', 5'-anhydrohexitol nucleic acids (HNA)) illustrated as:

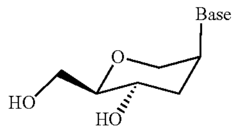

HNA

In some embodiments, one or more modifications further optionally include modifications of the ribose moiety, phosphate backbone and the nucleoside, or modifications of the nucleotide analogues at the 3' or the 5' terminus. For example, the 3' terminus optionally include a 3' cationic group, or by inverting the nucleoside at the 3'-terminus with a 3'-3' linkage. In another alternative, the 3'-terminus is optionally conjugated with an aminoalkyl group, e.g., a 3' C5-aminoalkyl dT. In an additional alternative, the 3'-terminus is optionally conjugated with an abasic site, e.g., with an apurinic or apyrimidinic site. In some instances, the 5'-terminus is conjugated with an aminoalkyl group, e.g., a 5'-O-alkylamino substituent. In some cases, the 5'-terminus is conjugated with an abasic site, e.g., with an apurinic or apyrimidinic site.

In some embodiments, the polynucleic acid molecule comprises one or more of the artificial nucleotide analogues described herein. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues described herein. In some embodiments, the artificial nucleotide analogues include 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O-N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues selected from 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O-N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methyl modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methoxyethyl (2'-O-MOE) modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of thiolphosphonate nucleotides.

In some instances, the polynucleic acid molecule comprises at least one of: from about 5% to about 100% modification, from about 10% to about 100% modification, from about 20% to about 100% modification, from about 30% to about 100% modification, from about 40% to about 100% modification, from about 50% to about 100% modification, from about 60% to about 100% modification, from about 70% to about 100% modification, from about 80% to about 100% modification, and from about 90% to about 100% modification.

In some cases, the polynucleic acid molecule comprises at least one of: from about 10% to about 90% modification, from about 20% to about 90% modification, from about 30% to about 90% modification, from about 40% to about 90% modification, from about 50% to about 90% modification, from about 60% to about 90% modification, from about 70% to about 90% modification, and from about 80% to about 100% modification.

In some cases, the polynucleic acid molecule comprises at least one of: from about 10% to about 80% modification, from about 20% to about 80% modification, from about 30% to about 80% modification, from about 40% to about 80% modification, from about 50% to about 80% modification, from about 60% to about 80% modification, and from about 70% to about 80% modification.

In some instances, the polynucleic acid molecule comprises at least one of: from about 10% to about 70% modification, from about 20% to about 70% modification, from about 30% to about 70% modification, from about 40% to about 70% modification, from about 50% to about 70% modification, and from about 60% to about 70% modification.

In some instances, the polynucleic acid molecule comprises at least one of: from about 10% to about 60% modification, from about 20% to about 60% modification, from about 30% to about 60% modification, from about 40% to about 60% modification, and from about 50% to about 60% modification.

In some cases, the polynucleic acid molecule comprises at least one of: from about 10% to about 50% modification, from about 20% to about 50% modification, from about 30% to about 50% modification, and from about 40% to about 50% modification.

In some cases, the polynucleic acid molecule comprises at least one of: from about 10% to about 40% modification, from about 20% to about 40% modification, and from about 30% to about 40% modification.

In some cases, the polynucleic acid molecule comprises at least one of: from about 10% to about 30% modification, and from about 20% to about 30% modification.

In some cases, the polynucleic acid molecule comprises from about 10% to about 20% modification.

In some cases, the polynucleic acid molecule comprises from about 15% to about 90%, from about 20% to about 80%, from about 30% to about 70%, or from about 40% to about 60% modifications.

In additional cases, the polynucleic acid molecule comprises at least about 15%, 20%, 30%, 40%, 50%, 60%, 70%, 80%, 90%, 95%, or 99% modification.

In some embodiments, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modifications.

In some instances, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modified nucleotides.

In some instances, from about 5 to about 100% of the polynucleic acid molecule comprise the artificial nucleotide analogues described herein. In some instances, about 5%, 10%, 15%, 20%, 25%, 30%, 35%, 40%, 45%, 50%, 55%, 60%, 65%, 70%, 75%, 80%, 85%, 90%, 95% or 100% of the polynucleic acid molecule comprise the artificial nucleotide analogues described herein. In some instances, about 5% of the polynucleic acid molecule comprises the artificial nucleotide analogues described herein. In some instances, about 10% of the polynucleic acid molecule comprises the artificial nucleotide analogues described herein. In some instances, about 15% of the polynucleic acid molecule comprises the artificial nucleotide analogues described herein. In some instances, about 20% of the polynucleic acid molecule comprises the artificial nucleotide analogues described herein. In some instances, about 25% of the polynucleic acid molecule comprises the artificial nucleotide analogues described herein. In some instances, about 30% of the polynucleic acid molecule comprises the artificial nucleotide analogues described herein. In some instances, about 35% of the polynucleic acid molecule comprises the artificial nucleotide analogues described herein. In some instances, about 40% of the polynucleic acid molecule comprises the artificial nucleotide analogues described herein. In some instances, about 45% of the polynucleic acid molecule comprises the artificial nucleotide analogues described herein. In some instances, about 50% of the polynucleic acid molecule comprises the artificial nucleotide analogues described herein. In some instances, about 55% of the polynucleic acid molecule comprises the artificial nucleotide analogues described herein. In some instances, about 60% of the polynucleic acid molecule comprises the artificial nucleotide analogues described herein. In some instances, about 65% of the polynucleic acid molecule comprises the artificial nucleotide analogues described herein. In some instances, about 70% of the polynucleic acid molecule comprises the artificial nucleotide analogues described herein. In some instances, about 75% of the polynucleic acid molecule comprises the artificial nucleotide analogues described herein. In some instances, about 80% of the polynucleic acid molecule comprises the artificial nucleotide analogues described herein. In some instances, about 85% of the polynucleic acid molecule comprises the artificial nucleotide analogues described herein. In some instances, about 90% of the polynucleic acid molecule comprises the artificial nucleotide analogues described herein. In some instances, about 95% of the polynucleic acid molecule comprises the artificial nucleotide analogues described herein. In some instances, about 96% of the polynucleic acid molecule comprises the artificial nucleotide analogues described herein. In some instances, about 97% of the polynucleic acid molecule comprises the artificial nucleotide analogues described herein. In some instances, about 98% of the polynucleic acid molecule comprises the artificial nucleotide analogues described herein. In some instances, about 99% of the polynucleic acid molecule comprises the artificial nucleotide analogues described herein. In some instances, about 100% of the polynucleic acid molecule comprises the artificial nucleotide analogues described herein. In some embodiments, the artificial nucleotide analogues include 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof.

In some embodiments, the polynucleic acid molecule comprises from about 1 to about 25 modifications in which the modification comprises an artificial nucleotide analogue described herein. In some embodiments, the polynucleic acid molecule comprises about 1 modification in which the modification comprises an artificial nucleotide analogue described herein. In some embodiments, the polynucleic acid molecule comprises about 2 modifications in which the modifications comprise an artificial nucleotide analogue described herein. In some embodiments, the polynucleic acid molecule comprises about 3 modifications in which the modifications comprise an artificial nucleotide analogue described herein. In some embodiments, the polynucleic acid molecule comprises about 4 modifications in which the modifications comprise an artificial nucleotide analogue described herein. In some embodiments, the polynucleic acid molecule comprises about 5 modifications in which the modifications comprise an artificial nucleotide analogue described herein. In some embodiments, the polynucleic acid molecule comprises about 6 modifications in which the modifications comprise an artificial nucleotide analogue described herein. In some embodiments, the polynucleic acid molecule comprises about 7 modifications in which the modifications comprise an artificial nucleotide analogue described herein. In some embodiments, the polynucleic acid molecule comprises about 8 modifications in which the modifications comprise an artificial nucleotide analogue described herein. In some embodiments, the polynucleic acid molecule comprises about 9 modifications in which the modifications comprise an artificial nucleotide analogue described herein. In some embodiments, the polynucleic acid molecule comprises about 10 modifications in which the modifications comprise an artificial nucleotide analogue described herein. In some embodiments, the polynucleic acid molecule comprises about 11 modifications in which the modifications comprise an artificial nucleotide analogue described herein. In some embodiments, the polynucleic acid molecule comprises about 12 modifications in which the modifications comprise an artificial nucleotide analogue described herein. In some embodiments, the polynucleic acid molecule comprises about 13 modifications in which the modifications comprise an artificial nucleotide analogue described herein. In some embodiments, the polynucleic acid molecule comprises about 14 modifications in which the modifications comprise an artificial nucleotide analogue described herein. In some embodiments, the polynucleic acid molecule comprises about 15 modifications in which the modifications comprise an artificial nucleotide analogue described herein. In some embodiments, the polynucleic acid molecule comprises about 16 modifications in which the modifications comprise an artificial nucleotide analogue described herein. In some embodiments, the polynucleic acid molecule comprises about 17 modifications in which the modifications comprise an artificial nucleotide analogue described herein. In some embodiments, the polynucleic acid molecule comprises about 18 modifications in which the modifications comprise an artificial nucleotide analogue described herein. In some embodiments, the polynucleic acid molecule comprises about 19 modifications in which the modifications comprise an artificial nucleotide analogue described herein. In some embodiments, the polynucleic acid molecule comprises about 20 modifications in which the modifications comprise an artificial nucleotide analogue described herein. In some embodiments, the polynucleic acid molecule comprises about 21 modifications in which the modifications comprise an artificial nucleotide analogue described herein. In some embodiments, the polynucleic acid molecule comprises about 19 modifications in which the modifications comprise an artificial nucleotide analogue described herein. In some embodiments, the polynucleic acid molecule comprises about 22 modifications in which the modifications comprise an artificial nucleotide analogue described herein.

In some embodiments, a polynucleic acid molecule is assembled from two separate polynucleotides, and one polynucleotide comprises the sense strand and the second polynucleotide comprises the antisense strand of the polynucleic acid molecule. In some embodiments, a polynucleic acid molecule comprises a sense strand and antisense strand, and pyrimidine nucleotides in the sense strand comprises 2'-O-methylpyrimidine nucleotides and purine nucleotides in the sense strand comprise 2'-deoxy purine nucleotides. In some embodiments, a polynucleic acid molecule comprises a sense strand and antisense strand, and pyrimidine nucleotides present in the sense strand comprise 2'-deoxy-2'-fluoro pyrimidine nucleotides and purine nucleotides present in the sense strand comprise 2'-deoxy purine nucleotides.

In some embodiments, a polynucleic acid molecule comprises a sense strand and antisense strand, and the pyrimidine nucleotides when present in said antisense strand are 2'-deoxy-2'-fluoro pyrimidine nucleotides and the purine nucleotides when present in said antisense strand are 2'-O-methyl purine nucleotides.

In some embodiments, a polynucleic acid molecule comprises a sense strand and antisense strand, and the pyrimidine nucleotides when present in said antisense strand are 2'-deoxy-2'-fluoro pyrimidine nucleotides and the purine nucleotides when present in said antisense strand comprise 2'-deoxy-purine nucleotides.

In some embodiments, a polynucleic acid molecule comprises a sense strand and antisense strand, and the sense strand comprises a 2'-O-methyl modified nucleotide at the 5'-end. Alternatively and/or additionally, a polynucleic acid molecule comprises a sense strand and antisense strand, and the sense strand comprises at least two consecutive 2'-O-methyl modified nucleotides at the 5'-end. Alternatively and/or additionally, a polynucleic acid molecule comprises a sense strand and antisense strand, and the sense strand comprises at least three, four, five, or six consecutive 2'-O-methyl modified nucleotides at the 5'-end. Alternatively and/or additionally, a polynucleic acid molecule comprises a sense strand and antisense strand, and the sense strand comprises six consecutive 2'-O-methyl modified nucleotides at the 5'-end.

Alternatively and/or additionally, a polynucleic acid molecule comprises a sense strand and antisense strand, and the sense strand comprises at least one 2'-F modified nucleotides. Alternatively and/or additionally, a polynucleic acid molecule comprises a sense strand and antisense strand, and the sense strand comprises at least two, at least three 2'-F modified nucleotides. Alternatively and/or additionally, a polynucleic acid molecule comprises a sense strand and antisense strand, and the sense strand comprises at least two, at least three consecutive 2'-F modified nucleotides.

In some embodiments, a polynucleic acid molecule comprises a sense strand and antisense strand, and the sense strand comprises a 2'-O-methyl modified nucleotide at the 3'-end. Alternatively and/or additionally, a polynucleic acid molecule comprises a sense strand and antisense strand, and the sense strand comprises at least two consecutive 2'-O-methyl modified nucleotides at the 3'-end. Alternatively and/or additionally, a polynucleic acid molecule comprises a sense strand and antisense strand, and the sense strand comprises at least three, four, five, six, seven, eight, nine, or ten consecutive 2'-O-methyl modified nucleotides at the 3'-end. Alternatively and/or additionally, a polynucleic acid molecule comprises a sense strand and antisense strand, and the sense strand comprises ten consecutive 2'-O-methyl modified nucleotides at the 3'-end.

Alternatively and/or additionally, a polynucleic acid molecule comprises a sense strand and antisense strand, and the antisense strand comprises a 2'-O-methyl modified nucleotide at the 5'-end. Alternatively and/or additionally, a polynucleic acid molecule comprises a sense strand and antisense strand, and the antisense strand comprises a 2'-O-methyl modified nucleotide at the 3'-end. Alternatively and/or additionally, a polynucleic acid molecule comprises a sense strand and antisense strand, and the antisense strand comprises at least two, at least three, at least four, at least five consecutive 2'-O-methyl modified nucleotide at the 3'-end. Alternatively and/or additionally, a polynucleic acid molecule comprises a sense strand and antisense strand, and the antisense strand comprises five consecutive 2'-O-methyl modified nucleotide at the 3'-end. Alternatively and/or additionally, a polynucleic acid molecule comprises a sense strand and antisense strand, and the antisense strand comprises at least one, at least two, at least three, at least four 2'-F modified nucleotides. Alternatively and/or additionally, a polynucleic acid molecule comprises a sense strand and antisense strand, and the antisense strand comprises four 2'-F modified nucleotides, and any two of the four 2'-F modified nucleotides are not consecutive. In some embodiments, a polynucleic acid molecule comprises a sense strand and antisense strand, and the antisense strand comprises two overhang nucleotides at the 3'-end.

In some embodiments, a polynucleic acid molecule comprises a sense strand and antisense strand. In some embodiments, a polynucleic acid molecule comprises a sense strand and antisense strand, wherein the sense strand includes a terminal cap moiety at the 5'-end, the 3'-end, or both of the 5' and 3' ends of the sense strand. In other embodiments, the terminal cap moiety is an inverted deoxy abasic moiety.

In some embodiments, a polynucleic acid molecule comprises a sense strand and an antisense strand, wherein the antisense strand comprises a phosphate backbone modification at the 3' end of the antisense strand. In some instances, the phosphate backbone modification is a phosphorothioate. In some embodiments, a polynucleic acid molecule comprises a sense strand and antisense strand, and the sense strand comprises at least two phosphorothioate internucleotide linkages. Alternatively and/or additionally, the antisense strand comprises at least two, at least three phosphorothioate internucleotide linkages.

In some embodiments, a polynucleic acid molecule comprises a sense strand and an antisense strand, wherein the antisense strand comprises a glyceryl modification at the 3' end of the antisense strand.

In some embodiments, a polynucleic acid molecule comprises a sense strand and an antisense strand, in which the sense strand comprises a sequence of SEQ ID NO: 1 and an antisense strand comprises a sequence of SEQ ID NO: 2, and the sense strand comprises at least three, four, five, or six consecutive 2'-O-methyl modified nucleotides at the 5'-end and at least two, or at least three 2'-F modified nucleotides.

In some embodiments, a polynucleic acid molecule comprises a sense strand and an antisense strand, in which the sense strand comprises a sequence of SEQ ID NO: 1 and an antisense strand comprises a sequence of SEQ ID NO: 2, and the antisense strand comprises at least two, at least three, at least four, at least five consecutive 2'-O-methyl modified nucleotide at the 3'-end, and at least one, at least two, at least three, at least four 2'-F modified nucleotides.

In some embodiments, a polynucleic acid molecule comprises a sense strand and an antisense strand, in which the sense strand comprises a sequence of SEQ ID NO: 1 and an antisense strand comprises a sequence of SEQ ID NO: 2, and the antisense strand comprises 2'-O-methyl modified nucleotides at the 5'-end and at the 3'-end.

In some embodiments, a polynucleic acid molecule comprises a sense strand and an antisense strand, in which the sense strand comprises a sequence of SEQ ID NO: 1 and an antisense strand comprises a sequence of SEQ ID NO: 2, and the antisense strand comprises at least five consecutive 2'-O-methyl modified nucleotide at the 3'-end and four 2'-F modified nucleotides, wherein any two of the four 2'-F modified nucleotides are not consecutive.

In some embodiments, a polynucleic acid molecule comprises a sense strand and an antisense strand, in which the sense strand comprises a sequence of SEQ ID NO: 1 and an antisense strand comprises a sequence of SEQ ID NO: 2, and the sense strand and/or antisense strand comprises at least 60%, at least 65%, at least 70%, at least 75%, at least 80%, at least 85%, at least 90%, at least 95%, or 100% of modified nucleotides of corresponding sequences of SEQ ID NO: 3 and/or SEQ ID NO: 4, respectively.

In some cases, one or more of the artificial nucleotide analogues described herein are resistant toward nucleases such as for example ribonuclease such as RNase H, deoxyribonuclease such as DNase, or exonuclease such as 5'-3' exonuclease and 3'-5' exonuclease when compared to natural polynucleic acid molecules. In some instances, artificial nucleotide analogues comprising 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or combinations thereof are resistant toward nucleases such as for example ribonuclease such as RNase H, deoxyribonuclease such as DNase, or exonuclease such as 5'-3' exonuclease and 3'-5' exonuclease. In some instances, 2'-O-methyl modified polynucleic acid molecule is nuclease resistance (e.g., RNase H, DNase, 5'-3' exonuclease or 3'-5' exonuclease resistance). In some instances, 2'O-methoxyethyl (2'-O-MOE) modified polynucleic acid molecule is nuclease resistance (e.g., RNase H, DNase, 5'-3' exonuclease or 3'-5' exonuclease resistance). In some instances, 2'-O-aminopropyl modified polynucleic acid molecule is nuclease resistance (e.g., RNase H, DNase, 5'-3' exonuclease or 3'-5' exonuclease resistance). In some instances, 2'-deoxy modified polynucleic acid molecule is nuclease resistance (e.g., RNase H, DNase, 5'-3' exonuclease or 3'-5' exonuclease resistance). In some instances, 2'-deoxy-2'-fluoro modified polynucleic acid molecule is nuclease resistance (e.g., RNase H, DNase, 5'-3' exonuclease or 3'-5' exonuclease resistance). In some instances, 2'-O-aminopropyl (2'-O-AP) modified polynucleic acid molecule is nuclease resistance (e.g., RNase H, DNase, 5'-3' exonuclease or 3'-5' exonuclease resistance). In some instances, 2'-O-dimethylaminoethyl (2'-O-DMAOE) modified polynucleic acid molecule is nuclease resistance (e.g., RNase H, DNase, 5'-3' exonuclease or 3'-5' exonuclease resistance). In some instances, 2'-O-dimethylaminopropyl (2'-O-DMAP) modified polynucleic acid molecule is nuclease resistance (e.g., RNase H, DNase, 5'-3' exonuclease or 3'-5' exonuclease resistance). In some instances, 2'-O-dimethylaminoethyloxyethyl (2'-O-DMAEOE) modified polynucleic acid molecule is nuclease resistance (e.g., RNase H, DNase, 5'-3' exonuclease or 3'-5' exonuclease resistance). In some instances, 2'-O—N-methylacetamido (2'-O-NMA) modified polynucleic acid molecule is nuclease resistance (e.g., RNase H, DNase, 5'-3' exonuclease or 3'-5' exonuclease resistance). In some instances, LNA modified polynucleic acid molecule is nuclease resistance (e.g., RNase H, DNase, 5'-3' exonuclease or 3'-5' exonuclease resistance). In some instances, ENA modified polynucleic acid molecule is nuclease resistance (e.g., RNase H, DNase, 5'-3' exonuclease or 3'-5' exonuclease resistance). In some instances, HNA modified polynucleic acid molecule is nuclease resistance (e.g., RNase H, DNase, 5'-3' exonuclease or 3'-5' exonuclease resistance). In some instances, morpholinos is nuclease resistance (e.g., RNase H, DNase, 5'-3' exonuclease or 3'-5' exonuclease resistance). In some instances, PNA modified polynucleic acid molecule is resistant to nucleases (e.g., RNase H, DNase, 5'-3' exonuclease or 3'-5' exonuclease resistance). In some instances, methylphosphonate nucleotides modified polynucleic acid molecule is nuclease resistance (e.g., RNase H, DNase, 5'-3' exonuclease or 3'-5' exonuclease resistance). In some instances, thiolphosphonate nucleotides modified polynucleic acid molecule is nuclease resistance (e.g., RNase H, DNase, 5'-3' exonuclease or 3'-5' exonuclease resistance). In some instances, polynucleic acid molecule comprising 2'-fluoro N3-P5'-phosphoramidites is nuclease resistance (e.g., RNase H, DNase, 5'-3' exonuclease or 3'-5' exonuclease resistance). In some instances, the 5' conjugates described herein inhibit 5'-3' exonucleolytic cleavage. In some instances, the 3' conjugates described herein inhibit 3'-5' exonucleolytic cleavage.

In some embodiments, one or more of the artificial nucleotide analogues described herein have increased binding affinity toward their mRNA target relative to an equivalent natural polynucleic acid molecule. The one or more of the artificial nucleotide analogues comprising 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, or 2'-fluoro N3-P5'-phosphoramidites have increased binding affinity toward their mRNA target relative to an equivalent natural polynucleic acid molecule. In some instances, 2'-O-methyl modified polynucleic acid molecule has increased binding affinity toward their mRNA target relative to an equivalent natural polynucleic acid molecule. In some instances, 2'-O-methoxyethyl (2'-O-MOE) modified polynucleic acid molecule has increased binding affinity toward their mRNA target relative to an equivalent natural polynucleic acid molecule. In some instances, 2'-O-aminopropyl modified polynucleic acid molecule has increased binding affinity toward their mRNA target relative to an equivalent natural polynucleic acid molecule. In some instances, 2'-deoxy modified polynucleic acid molecule has increased binding affinity toward their mRNA target relative to an equivalent natural polynucleic acid molecule. In some instances, 2'-deoxy-2'-fluoro modified polynucleic acid molecule has increased binding affinity toward their mRNA target relative to an equivalent natural polynucleic acid molecule. In some instances, 2'-O-aminopropyl (2'-O-AP) modified polynucleic acid molecule has increased binding affinity toward their mRNA target relative to an equivalent natural polynucleic acid molecule. In some instances, 2'-O-dimethylaminoethyl (2'-O-DMAOE) modified polynucleic acid molecule has increased binding affinity toward their mRNA target relative to an equivalent natural polynucleic acid molecule. In some instances, 2'-O-dimethylaminopropyl (2'-O-DMAP) modified polynucleic acid molecule has increased binding affinity toward their mRNA target relative to an equivalent natural polynucleic acid molecule. In some instances, 2'-O-dimethylaminoethyloxyethyl (2'-O-DMAEOE) modified polynucleic acid molecule has increased binding affinity toward their mRNA target relative to an equivalent natural polynucleic acid molecule. In some instances, 2'-O—N-methylacetamido (2'-O-NMA) modified polynucleic acid molecule has increased binding affinity toward their mRNA target relative to an equivalent natural polynucleic acid molecule. In some instances, LNA modified polynucleic acid molecule has increased binding affinity toward their mRNA target relative to an equivalent natural polynucleic acid molecule. In some instances, ENA modified polynucleic acid molecule has increased binding affinity toward their mRNA target relative to an equivalent natural polynucleic acid molecule. In some instances, PNA modified polynucleic acid molecule has increased binding affinity toward their mRNA target relative to an equivalent natural polynucleic acid molecule. In some instances, HNA modified polynucleic acid molecule has increased binding affinity toward their mRNA target relative to an equivalent natural polynucleic acid molecule. In some instances, morpholino modified polynucleic acid molecule has increased binding affinity toward their mRNA target relative to an equivalent natural polynucleic acid molecule. In some instances, methylphosphonate nucleotides modified polynucleic acid molecule has increased binding affinity toward their mRNA target relative to an equivalent natural polynucleic acid molecule. In some instances, thiolphosphonate nucleotides modified polynucleic acid molecule has increased binding affinity toward their mRNA target relative to an equivalent natural polynucleic acid molecule. In some instances, polynucleic acid molecule comprising 2'-fluoro N3-P5'-phosphoramidites has increased binding affinity toward their mRNA target relative to an equivalent natural polynucleic acid molecule. In some cases, the increased affinity is illustrated with a lower Kd, a higher melt temperature (Tm), or a combination thereof.

In some embodiments, a polynucleic acid molecule described herein is a chirally pure (or stereo pure) polynucleic acid molecule, or a polynucleic acid molecule comprising a single enantiomer. In some instances, the polynucleic acid molecule comprises L-nucleotide. In some instances, the polynucleic acid molecule comprises D-nucleotides. In some instance, a polynucleic acid molecule composition comprises less than 30%, 25%, 20%, 15%, 10%, 5%, 4%, 3%, 2%, 1%, or less of its mirror enantiomer. In some cases, a polynucleic acid molecule composition comprises less than 30%, 25%, 20%, 15%, 10%, 5%, 4%, 3%, 2%, 1%, or less of a racemic mixture. In some instances, the polynucleic acid molecule is a polynucleic acid molecule described in: U.S. Patent Publication Nos: 2014/194610 and 2015/211006; and PCT Publication No.: WO2015107425.

In some embodiments, a polynucleic acid molecule described herein is further modified to include an aptamer conjugating moiety. In some instances, the aptamer conjugating moiety is a DNA aptamer conjugating moiety. In some instances, the aptamer conjugating moiety is Alphamer (Centauri Therapeutics), which comprises an aptamer portion that recognizes a specific cell-surface target and a portion that presents specific epitopes for attaching to circulating antibodies. In some instance, a polynucleic acid molecule described herein is further modified to include an aptamer conjugating moiety as described in: U.S. Patent Nos: 8,604, 184, 8,591,910, and 7,850,975.

In additional embodiments, a polynucleic acid molecule described herein is modified to increase its stability. In some embodiment, the polynucleic acid molecule is RNA (e.g., siRNA). In some instances, the polynucleic acid molecule is modified by one or more of the modifications described above to increase its stability. In some cases, the polynucleic acid molecule is modified at the 2' hydroxyl position, such as by 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modification or by a locked or bridged ribose conformation (e.g., LNA or ENA). In some cases, the polynucleic acid molecule is modified by 2'-O-methyl and/or 2'-O-methoxyethyl ribose. In some cases, the polynucleic acid molecule also includes morpholinos, PNAs, HNA, methylphosphonate nucleotides, thiolphosphonate nucleotides, and/or 2'-fluoro N3-P5'-phosphoramidites to increase its stability. In some instances, the polynucleic acid molecule is a chirally pure (or stereo pure) polynucleic acid molecule. In some instances, the chirally pure (or stereo pure) polynucleic acid molecule is modified to increase its stability. Suitable modifications to the RNA to increase stability for delivery will be apparent to the skilled person.

In some instances, the polynucleic acid molecule is a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. In some instances, the polynucleic acid molecule is assembled from two separate polynucleotides, where one strand is the sense strand and the other is the antisense strand, wherein the antisense and sense strands are self-complementary (e.g., each strand comprises nucleotide sequence that is complementary to nucleotide sequence in the other strand; such as where the antisense strand and sense strand form a duplex or double stranded structure, for example wherein the double stranded region is about 19, 20, 21, 22, 23, or more base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the polynucleic acid molecule is assembled from a single oligonucleotide, where the self-complementary sense and antisense regions of the polynucleic acid molecule are linked by means of a nucleic acid based or non-nucleic acid-based linker(s).

In some cases, the polynucleic acid molecule is a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. In other cases, the polynucleic acid molecule is a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide is processed either in vivo or in vitro to generate an active polynucleic acid molecule capable of mediating RNAi. In additional cases, the polynucleic acid molecule also comprises a single-stranded polynucleotide having nucleotide sequence complementary to nucleotide sequence in a target nucleic acid molecule or a portion thereof (for example, where such polynucleic acid molecule does not require the presence within the polynucleic acid molecule of nucleotide sequence corresponding to the target nucleic acid sequence or a portion thereof), wherein the single stranded polynucleotide further comprises a terminal phosphate group, such as a 5'-phosphate (see for example Martinez et al., 2002, *Cell.,* 110, 563-574 and Schwarz et al., 2002, Molecular Cell, 10, 537-568), or 5',3'-diphosphate.

In some instances, an asymmetric hairpin is a linear polynucleic acid molecule comprising an antisense region, a loop portion that comprises nucleotides or non-nucleotides, and a sense region that comprises fewer nucleotides than the antisense region to the extent that the sense region has enough complimentary nucleotides to base pair with the antisense region and form a duplex with loop. For example, an asymmetric hairpin polynucleic acid molecule comprises an antisense region having length sufficient to mediate RNAi in a cell or in vitro system (e.g. about 19 to about 22 nucleotides) and a loop region comprising about 4 to about 8 nucleotides, and a sense region having about 3 to about 18 nucleotides that are complementary to the antisense region. In some cases, the asymmetric hairpin polynucleic acid molecule also comprises a 5'-terminal phosphate group that is chemically modified. In additional cases, the loop portion of the asymmetric hairpin polynucleic acid molecule comprises nucleotides, non-nucleotides, linker molecules, or conjugate molecules.

In some embodiments, an asymmetric duplex is a polynucleic acid molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex polynucleic acid molecule comprises an antisense region having length sufficient to mediate RNAi in a cell or in vitro system (e.g., about 19 to about 22 nucleotides) and a sense region having about 3 to about 18 nucleotides that are complementary to the antisense region.

In some cases, a universal base refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example Loakes, 2001, Nucleic Acids Research, 29, 2437-2447).

Polynucleic Acid Molecule Synthesis

In some embodiments, a polynucleic acid molecule described herein is constructed using chemical synthesis and/or enzymatic ligation reactions using procedures known in the art. For example, a polynucleic acid molecule is chemically synthesized using naturally occurring nucleotides or variously modified nucleotides designed to increase the biological stability of the molecules or to increase the physical stability of the duplex formed between the polynucleic acid molecule and target nucleic acids. Exemplary methods include those described in: U.S. Pat. Nos. 5,142,047; 5,185,444; 5,889,136; 6,008,400; and 6,111,086; PCT Publication No. WO2009099942; or European Publication No. 1579015. Additional exemplary methods include those described in: Griffey et al., "2'-O-aminopropyl ribonucleotides: a zwitterionic modification that enhances the exonuclease resistance and biological activity of antisense oligonucleotides," *J. Med. Chem.* 39 (26): 5100-5109 (1997)); Obika, et al. "Synthesis of 2'-0,4'-C-methyleneuridine and -cytidine. Novel bicyclic nucleosides having a fixed C3,-endo sugar puckering". *Tetrahedron Letters* 38 (50): 8735 (1997); Koizumi, M. "ENA oligonucleotides as therapeutics". *Current opinion in molecular therapeutics* 8 (2): 144-149 (2006); and Abramova et al., "Novel oligonucleotide analogues based on morpholino nucleoside subunits-antisense technologies: new chemical possibilities," Indian Journal of Chemistry 48B: 1721-1726 (2009). Alternatively, the polynucleic acid molecule is produced biologically using an expression vector into which a polynucleic acid molecule has been subcloned in an antisense orientation (i.e., RNA transcribed from the inserted polynucleic acid molecule will be of an antisense orientation to a target polynucleic acid molecule of interest).

In some embodiments, a polynucleic acid molecule is synthesized via a tandem synthesis methodology, wherein both strands are synthesized as a single contiguous oligonucleotide fragment or strand separated by a cleavable linker which is subsequently cleaved to provide separate fragments or strands that hybridize and permit purification of the duplex.

In some instances, a polynucleic acid molecule is also assembled from two distinct nucleic acid strands or fragments wherein one fragment includes the sense region and the second fragment includes the antisense region of the molecule.

Additional modification methods for incorporating, for example, sugar, base and phosphate modifications include: Eckstein et al., International Publication PCT No. WO 92/07065;

Perrault et al. Nature, 1990, 344, 565-568; Pieken et al. *Science,* 1991, 253, 314-317; Usman and Cedergren, *Trends in Biochem. Sci.,* 1992, 17, 334-339; Usman et al. International Publication PCT No. WO 93/15187; Sproat, U.S. Pat. No. 5,334,711 and Beigelman et al., 1995, *J. Biol. Chem.,* 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.,* 39, 1131; Earnshaw and Gait, 1998, *Biopolymers (Nucleic Acid Sciences)*, 48, 39-55; Verma and Eckstein, 1998, *Annu. Rev. Biochem.,* 67, 99-134; and Burlina et al., 1997, *Bioorg. Med. Chem.,* 5, 1999-2010. Such publications describe general methods and strategies to determine the location of incorporation of sugar, base and/or phosphate modifications and the like into nucleic acid molecules without modulating catalysis.

In some instances, while chemical modification of the polynucleic acid molecule internucleotide linkages with phosphorothioate, phosphorodithioate, and/or 5'-methylphosphonate linkages improves stability, excessive modifications sometimes cause toxicity or decreased activity. Therefore, when designing nucleic acid molecules, the amount of these internucleotide linkages in some cases is minimized. In such cases, the reduction in the concentration of these linkages lowers toxicity, increases efficacy and higher specificity of these molecules.

Polynucleic Acid Molecule Conjugates

In some embodiments, a polynucleic acid molecule (B) is further conjugated to a polypeptide (A) for delivery to a site of interest. In some instances, at least one polypeptide A is conjugated to at least one B. In some instances, the at least one polypeptide A is conjugated to the at least one B to form an A-B conjugate. In some embodiments, at least one A is conjugated to the 5' terminus of B, the 3' terminus of B, an internal site on B, or in any combinations thereof. In some instances, the at least one polypeptide A is conjugated to at least two B. In some instances, the at least one polypeptide A is conjugated to at least 2, 3, 4, 5, 6, 7, 8, or more B.

In some embodiments, at least one polypeptide A is conjugated at one terminus of at least one B while at least one C is conjugated at the opposite terminus of the at least one B to form an A-B-C conjugate. In some instances, at least one polypeptide A is conjugated at one terminus of the at least one B while at least one of C is conjugated at an internal or terminal site on the at least one B. In some instances, at least one polypeptide A is conjugated directly to the at least one C. In some instances, the at least one B is conjugated indirectly to the at least one polypeptide A via the at least one C to form an A-C-B conjugate.

In some instances, at least one B and/or at least one C, and optionally at least one D are conjugated to at least one polypeptide A. In some instances, the at least one B is conjugated at a terminus (e.g., a 5' terminus or a 3' terminus) to the at least one polypeptide A or are conjugated via an internal site to the at least one polypeptide A. In some cases, the at least one C is conjugated either directly to the at least one polypeptide A or indirectly via the at least one B. If indirectly via the at least one B, the at least one C is conjugated either at the same terminus as the at least one polypeptide A on B, at opposing terminus from the at least one polypeptide A, or independently at an internal site. In some instances, at least one additional polypeptide A is further conjugated to the at least one polypeptide A, to B, or to C. In additional instances, the at least one D is optionally conjugated either directly or indirectly to the at least one polypeptide A, to the at least one B, or to the at least one C. If directly to the at least one polypeptide A, the at least one D is also optionally conjugated to the at least one B to form an A-D-B conjugate or is optionally conjugated to the at least one B and the at least one C to form an A-D-B-C conjugate. In some instances, the at least one D is directly conjugated to the at least one polypeptide A and indirectly to the at least one B and the at least one C to form a D-A-B-C conjugate. If indirectly to the at least one polypeptide A, the at least one D is also optionally conjugated to the at least one B to form an A-B-D conjugate or is optionally conjugated to the at least one B and the at least one C to form an A-B-D-C conjugate. In some instances, at least one additional D is further conjugated to the at least one polypeptide A, to B, or to C.

Binding Moiety

In some embodiments, the binding moiety A is a polypeptide, a peptide, or non-peptide ligand. In some instances, the polypeptide is an antibody or its fragment thereof. In some cases, the fragment is a binding fragment. In some instances, the antibody or antigen binding fragment thereof comprises a humanized antibody or antigen binding fragment thereof, murine antibody or antigen binding fragment thereof, chimeric antibody or antigen binding fragment thereof, monoclonal antibody or antigen binding fragment thereof, monovalent Fab', divalent $Fab_2$, $F(ab)'_3$ fragments, single-chain variable fragment (scFv), bis-scFv, $(scFv)_2$, diabody, minibody, nanobody, triabody, tetrabody, disulfide stabilized Fv protein (dsFv), single-domain antibody (sdAb), Ig NAR, camelid antibody or antigen binding fragment thereof, bispecific antibody or biding fragment thereof, or a chemically modified derivative thereof.

In some embodiments, the binding moiety A is a bispecific antibody or antigen binding fragment thereof. In some instances, the bispecific antibody is a trifunctional antibody or a bispecific mini-antibody. In some cases, the bispecific antibody is a trifunctional antibody. In some instances, the trifunctional antibody is a full length monoclonal antibody comprising binding sites for two different antigens.

In some cases, the bispecific antibody is a bispecific mini-antibody. In some instances, the bispecific mini-antibody comprises divalent $Fab_2$, $F(ab)'_3$ fragments, bis-scFv, $(scFv)_2$, diabody, minibody, triabody, tetrabody or a bi-specific T-cell engager (BiTE). In some embodiments, the bi-specific T-cell engager is a fusion protein that contains two single-chain variable fragments (scFvs) in which the two scFvs target epitopes of two different antigens.

In some embodiments, the binding moiety A is a bispecific mini-antibody. In some instances, A is a bispecific $Fab_2$. In some instances, A is a bispecific $F(ab)'_3$ fragment. In some cases, A is a bispecific bis-scFv. In some cases, A is a bispecific $(scFv)_2$. In some embodiments, A is a bispecific diabody. In some embodiments, A is a bispecific minibody. In some embodiments, A is a bispecific triabody. In other embodiments, A is a bispecific tetrabody. In other embodiments, A is a bi-specific T-cell engager (BiTE).

In some embodiments, the binding moiety A is a trispecific antibody. In some instances, the trispecific antibody comprises $F(ab)'_3$ fragments or a triabody. In some instances, A is a trispecific $F(ab)'_3$ fragment. In some cases, A is a triabody. In some embodiments, A is a trispecific antibody as described in Dimas, et al., "Development of a trispecific antibody designed to simultaneously and efficiently target three different antigens on tumor cells," *Mol. Pharmaceutics,* 12 (9): 3490-3501 (2015).

In some embodiments, the binding moiety A is an antibody or antigen binding fragment thereof that recognizes a cell surface protein. In some instances, the binding moiety A is an antibody or antigen binding fragment thereof that recognizes a cell surface protein on a muscle cell. In some cases, the binding moiety A is an antibody or antigen binding fragment thereof that recognizes a cell surface protein on a skeletal muscle cell.

In some embodiments, exemplary antibodies include, but are not limited to, an anti-myosin antibody, an anti-transferrin receptor antibody, and an antibody that recognizes Muscle-Specific kinase (MuSK). In some instances, the antibody is an anti-transferrin receptor (anti-CD71) antibody.

In some embodiments, where the antibody is an anti-transferrin receptor (anti-CD71) antibody, the anti-transferrin receptor antibody specifically binds to a transferrin receptor (TfR), preferably, specifically binds to transferrin receptor 1 (TfR1), or more preferably, specifically binds to human transferrin receptor 1 (TfR1) (or human CD71).

In some instances, the anti-transferrin receptor antibody comprises a variable heavy chain (VH) region and a variable light chain (VL) region, wherein the VH region comprises HCDR1 sequence comprising SEQ ID NO: 17; HCDR2 sequence $EINPIX_1GRSNYAX_2KFQG$ (SEQ ID NO: 109), wherein $X_1$ is selected from N or Q and $X_2$ is selected from Q or E; and HCDR3 sequence comprising SEQ ID NO: 19.

In some embodiments, the VH region of the anti-transferring antibody comprises HCDR1, HCDR2, and HCDR3 sequences selected from Table 2.

TABLE 2

| Name | HCDR1 | SEQ ID NO: | HCDR2 | SEQ ID NO: | HCDR3 | SEQ ID NO: |
|---|---|---|---|---|---|---|
| 13E4_VH1 | YTFTNYWMH | 17 | EINPINGRSNYAQKFQG | 18 | GTRAMHY | 19 |
| 13E4_VH2* | YTFTNYWMH | 17 | EINPINGRSNYAEKFQG | 20 | GTRAMHY | 19 |
| 13E4_VH3 | YTFTNYWMH | 17 | EINPIQGRSNYAEKFQG | 21 | GTRAMHY | 19 |

*13E4_VH2 shares the same HCDR1, HCDR2, and HCDR3 sequences with anti-transferrin receptor antibody 13E4_VH4

In some embodiments, the VH region comprises HCDR1 sequence comprising SEQ ID NO: 17; HCDR2 sequence comprising SEQ ID NO: 18, 20, or 21; and HCDR3 sequence comprising SEQ ID NO: 19. In some instances, the VH region comprises HCDR1 sequence comprising SEQ ID NO: 17, HCDR2 sequence comprising SEQ ID NO: 18, and HCDR3 sequence comprising SEQ ID NO: 19. In some instances, the VH region comprises HCDR1 sequence comprising SEQ ID NO: 17, HCDR2 sequence comprising SEQ ID NO: 20, and HCDR3 sequence comprising SEQ ID NO: 19. In some instances, the VH region comprises HCDR1 sequence comprising SEQ ID NO: 17, HCDR2 sequence comprising SEQ ID NO: 21, and HCDR3 sequence comprising SEQ ID NO: 19.

In some embodiments, the VL region of the anti-transferrin receptor antibody comprises LCDR1 sequence RTSENIYX$_3$NLA (SEQ ID NO: 110), LCDR2 sequence AX$_4$TNLAX$_5$ (SEQ ID NO: 111), and LCDR3 sequence QHFWGTPLTX$_6$ (SEQ ID NO: 112), wherein X$_3$ is selected from N or S, X$_4$ is selected from A or G, X$_5$ is selected from D or E, and X$_6$ is present or absence, and if present, is F.

In some embodiments, the VL region of the anti-transferrin receptor antibody comprises LCDR1, LCDR2, and LCDR3 sequences selected from Table 3.

TABLE 3

| Name | LCDR1 | SEQ ID NO: | LCDR2 | SEQ ID NO: | LCDR3 | SEQ ID NO: |
|---|---|---|---|---|---|---|
| 13E4_VL1* | RTSENIYNNLA | 22 | AATNLAD | 23 | QHFWGTPLT | 24 |
| 13E4_VL3 | RTSENIYNNLA | 22 | AATNLAE | 25 | QHFWGTPLTF | 26 |
| 13E4_VL4 | RTSENIYSNLA | 27 | AGTNLAD | 28 | QHFWGTPLTF | 26 |

*13E4_VL1 shares the same LCDR1, LCDR2, and LCDR3 sequences with anti-transferrin receptor antibody 13E4_VL2

In some instances, the VL region comprises LCDR1 sequence RTSENIYX$_3$NLA (SEQ ID NO: 110), LCDR2 sequence comprising SEQ ID NO: 23, 25, or 28, and LCDR3 sequence comprising SEQ ID NO: 24 or 26, wherein X$_3$ is selected from N or S.

In some instances, the VL region comprises LCDR1 sequence comprising SEQ ID NO: 22 or 27, LCDR2 sequence AX$_4$TNLAX$_5$ (SEQ ID NO: 111), and LCDR3 sequence comprising SEQ ID NO: 24 or 26, wherein X$_4$ is selected from A or G, and X$_5$ is selected from D or E.

In some instances, the VL region comprises LCDR1 sequence comprising SEQ ID NO: 22 or 27, LCDR2 sequence SEQ ID NO: 23, 25, or 28, and LCDR3 sequence QHFWGTPLTX$_6$ (SEQ ID NO: 112), wherein X$_6$ is present or absence, and if present, is F.

In some instances, the VL region comprises LCDR1 sequence comprising SEQ ID NO: 22, LCDR2 sequence AATNLAX$_5$ (SEQ ID NO: 113), and LCDR3 sequence QHFWGTPLTX$_6$ (SEQ ID NO: 112), wherein X$_5$ is selected from D or E and X$_6$ is present or absence, and if present, is F.

In some instances, the VL region comprises LCDR1 sequence comprising SEQ ID NO: 22, LCDR2 sequence comprising SEQ ID NO: 23, and LCDR3 sequence comprising SEQ ID NO: 24.

In some instances, the VL region comprises LCDR1 sequence comprising SEQ ID NO: 22, LCDR2 sequence comprising SEQ ID NO: 25, and LCDR3 sequence comprising SEQ ID NO: 26.

In some instances, the VL region comprises LCDR1 sequence comprising SEQ ID NO: 27, LCDR2 sequence comprising SEQ ID NO: 28, and LCDR3 sequence comprising SEQ ID NO: 26.

In some embodiments, the anti-transferrin receptor antibody comprises a VH region and a VL region, wherein the VH region comprises HCDR1 sequence comprising SEQ ID NO: 17; HCDR2 sequence EINPIX$_1$GRSNYAX$_2$KFQG (SEQ ID NO: 109), wherein X$_1$ is selected from N or Q and X$_2$ is selected from Q or E; and HCDR3 sequence comprising SEQ ID NO: 19; and the VL region comprises LCDR1 sequence RTSENIYX$_3$NLA (SEQ ID NO: 110), LCDR2 sequence AX$_4$TNLAX$_5$ (SEQ ID NO: 111), and LCDR3 sequence QHFWGTPLTX$_6$ (SEQ ID NO: 112), wherein X$_3$ is selected from N or S, X$_4$ is selected from A or G, X$_5$ is selected from D or E, and X$_6$ is present or absence, and if present, is F.

In some instances, the anti-transferrin receptor antibody comprises a VH region and a VL region, wherein the VH region comprises HCDR1 sequence comprising SEQ ID NO: 17; HCDR2 sequence EINPIX$_1$GRSNYAX$_2$KFQG (SEQ ID NO: 109), wherein X$_1$ is selected from N or Q and X$_2$ is selected from Q or E; and HCDR3 sequence comprising SEQ ID NO: 19; and the VL region comprises LCDR1 sequence RTSENIYX$_3$NLA (SEQ ID NO: 110), LCDR2 sequence comprising SEQ ID NO: 23, 25, or 28, and LCDR3 sequence comprising SEQ ID NO: 24 or 26, wherein X$_3$ is selected from N or S.

In some instances, the anti-transferrin receptor antibody comprises a VH region and a VL region, wherein the VH region comprises HCDR1 sequence comprising SEQ ID NO: 17; HCDR2 sequence EINPIX$_1$GRSNYAX$_2$KFQG (SEQ ID NO: 109), wherein X$_1$ is selected from N or Q and X$_2$ is selected from Q or E; and HCDR3 sequence comprising SEQ ID NO: 19; and the VL region comprises LCDR1 sequence comprising SEQ ID NO: 22 or 27, LCDR2 sequence AX$_4$TNLAX$_5$ (SEQ ID NO: 111), and LCDR3 sequence comprising SEQ ID NO: 24 or 26, wherein X$_4$ is selected from A or G, and X$_5$ is selected from D or E.

In some instances, the anti-transferrin receptor antibody comprises a VH region and a VL region, wherein the VH region comprises HCDR1 sequence comprising SEQ ID NO: 17; HCDR2 sequence EINPIX$_1$GRSNYAX$_2$KFQG (SEQ ID NO: 109), wherein X$_1$ is selected from N or Q and X$_2$ is selected from Q or E; and HCDR3 sequence comprising SEQ ID NO: 19; and the VL region comprises LCDR1 sequence comprising SEQ ID NO: 22 or 27, LCDR2 sequence SEQ ID NO: 23, 25, or 28, and LCDR3 sequence QHFWGTPLTX$_6$ (SEQ ID NO: 112), wherein X$_6$ is present or absence, and if present, is F.

In some instances, the anti-transferrin receptor antibody comprises a VH region and a VL region, wherein the VH region comprises HCDR1 sequence comprising SEQ ID NO: 17; HCDR2 sequence EINPIX$_1$GRSNYAX$_2$KFQG (SEQ ID NO: 109), wherein $X_1$ is selected from N or Q and $X_2$ is selected from Q or E; and HCDR3 sequence comprising SEQ ID NO: 19; and the VL region comprises LCDR1 sequence comprising SEQ ID NO: 22, LCDR2 sequence AATNLAX$_5$ (SEQ ID NO: 113), and LCDR3 sequence QHFWGTPLTX$_6$ (SEQ ID NO: 112), wherein $X_5$ is selected from D or E and $X_6$ is present or absence, and if present, is F.

In some instances, the anti-transferrin receptor antibody comprises a VH region and a VL region, wherein the VH region comprises HCDR1 sequence comprising SEQ ID NO: 17; HCDR2 sequence EINPIX$_1$GRSNYAX$_2$KFQG (SEQ ID NO: 109), wherein $X_1$ is selected from N or Q and $X_2$ is selected from Q or E; and HCDR3 sequence comprising SEQ ID NO: 19; and the VL region comprises LCDR1 sequence comprising SEQ ID NO: 22, LCDR2 sequence comprising SEQ ID NO: 23, and LCDR3 sequence comprising SEQ ID NO: 24.

In some instances, the anti-transferrin receptor antibody comprises a VH region and a VL region, wherein the VH region comprises HCDR1 sequence comprising SEQ ID NO: 17; HCDR2 sequence EINPIX$_1$GRSNYAX$_2$KFQG (SEQ ID NO: 109), wherein $X_1$ is selected from N or Q and $X_2$ is selected from Q or E; and HCDR3 sequence comprising SEQ ID NO: 19; and the VL region comprises LCDR1 sequence comprising SEQ ID NO: 22, LCDR2 sequence comprising SEQ ID NO: 25, and LCDR3 sequence comprising SEQ ID NO: 26.

In some instances, the anti-transferrin receptor antibody comprises a VH region and a VL region, wherein the VH region comprises HCDR1 sequence comprising SEQ ID NO: 17; HCDR2 sequence EINPIX$_1$GRSNYAX$_2$KFQG (SEQ ID NO: 109), wherein $X_1$ is selected from N or Q and $X_2$ is selected from Q or E; and HCDR3 sequence comprising SEQ ID NO: 19; and the VL region comprises LCDR1 sequence comprising SEQ ID NO: 27, LCDR2 sequence comprising SEQ ID NO: 28, and LCDR3 sequence comprising SEQ ID NO: 26.

In some instances, the anti-transferrin receptor antibody comprises a VH region and a VL region, in which the VH region comprises HCDR1 sequence comprising SEQ ID NO: 17, HCDR2 sequence comprising SEQ ID NO: 18, and HCDR3 sequence comprising SEQ ID NO: 19; and the VL region comprises LCDR1 sequence RTSENIYX$_3$NLA (SEQ ID NO: 110), LCDR2 sequence comprising SEQ ID NO: 23, 25, or 28, and LCDR3 sequence comprising SEQ ID NO: 24 or 26, wherein $X_3$ is selected from N or S.

In some instances, the anti-transferrin receptor antibody comprises a VH region and a VL region, in which the VH region comprises HCDR1 sequence comprising SEQ ID NO: 17, HCDR2 sequence comprising SEQ ID NO: 18, and HCDR3 sequence comprising SEQ ID NO: 19; and the VL region comprises LCDR1 sequence comprising SEQ ID NO: 22 or 27, LCDR2 sequence AX$_4$TNLAX$_5$ (SEQ ID NO: 111), and LCDR3 sequence comprising SEQ ID NO: 24 or 26, wherein $X_4$ is selected from A or G, and $X_5$ is selected from D or E.

In some instances, the anti-transferrin receptor antibody comprises a VH region and a VL region, in which the VH region comprises HCDR1 sequence comprising SEQ ID NO: 17, HCDR2 sequence comprising SEQ ID NO: 18, and HCDR3 sequence comprising SEQ ID NO: 19; and the VL region comprises LCDR1 sequence comprising SEQ ID NO: 22 or 27, LCDR2 sequence SEQ ID NO: 23, 25, or 28, and LCDR3 sequence QHFWGTPLTX$_6$ (SEQ ID NO: 112), wherein $X_6$ is present or absence, and if present, is F.

In some instances, the anti-transferrin receptor antibody comprises a VH region and a VL region, in which the VH region comprises HCDR1 sequence comprising SEQ ID NO: 17, HCDR2 sequence comprising SEQ ID NO: 18, and HCDR3 sequence comprising SEQ ID NO: 19; and the VL region comprises LCDR1 sequence comprising SEQ ID NO: 22, LCDR2 sequence AATNLAX$_5$ (SEQ ID NO: 113), and LCDR3 sequence QHFWGTPLTX$_6$ (SEQ ID NO: 112), wherein $X_5$ is selected from D or E and $X_6$ is present or absence, and if present, is F.

In some instances, the anti-transferrin receptor antibody comprises a VH region and a VL region, in which the VH region comprises HCDR1 sequence comprising SEQ ID NO: 17, HCDR2 sequence comprising SEQ ID NO: 18, and HCDR3 sequence comprising SEQ ID NO: 19; and the VL region comprises LCDR1 sequence comprising SEQ ID NO: 22, LCDR2 sequence comprising SEQ ID NO: 23, and LCDR3 sequence comprising SEQ ID NO: 24.

In some instances, the anti-transferrin receptor antibody comprises a VH region and a VL region, in which the VH region comprises HCDR1 sequence comprising SEQ ID NO: 17, HCDR2 sequence comprising SEQ ID NO: 18, and HCDR3 sequence comprising SEQ ID NO: 19; and the VL region comprises LCDR1 sequence comprising SEQ ID NO: 22, LCDR2 sequence comprising SEQ ID NO: 21, and LCDR3 sequence comprising SEQ ID NO: 26.

In some instances, the anti-transferrin receptor antibody comprises a VH region and a VL region, in which the VH region comprises HCDR1 sequence comprising SEQ ID NO: 17, HCDR2 sequence comprising SEQ ID NO: 18, and HCDR3 sequence comprising SEQ ID NO: 19; and the VL region comprises LCDR1 sequence comprising SEQ ID NO: 27, LCDR2 sequence comprising SEQ ID NO: 28, and LCDR3 sequence comprising SEQ ID NO: 26.

In some instances, the anti-transferrin receptor antibody comprises a VH region and a VL region, in which the VH region comprises HCDR1 sequence comprising SEQ ID NO: 17, HCDR2 sequence comprising SEQ ID NO: 20, and HCDR3 sequence comprising SEQ ID NO: 19; and the VL region comprises LCDR1 sequence RTSENIYX$_3$NLA (SEQ ID NO: 110), LCDR2 sequence comprising SEQ ID NO: 23, 25, or 28, and LCDR3 sequence comprising SEQ ID NO: 24 or 26, wherein $X_3$ is selected from N or S.

In some instances, the anti-transferrin receptor antibody comprises a VH region and a VL region, in which the VH region comprises HCDR1 sequence comprising SEQ ID NO: 17, HCDR2 sequence comprising SEQ ID NO: 20, and HCDR3 sequence comprising SEQ ID NO: 19; and the VL region comprises LCDR1 sequence comprising SEQ ID NO: 22 or 27, LCDR2 sequence AX$_4$TNLAX$_5$ (SEQ ID NO: 111), and LCDR3 sequence comprising SEQ ID NO: 24 or 26, wherein $X_4$ is selected from A or G, and $X_5$ is selected from D or E.

In some instances, the anti-transferrin receptor antibody comprises a VH region and a VL region, in which the VH region comprises HCDR1 sequence comprising SEQ ID NO: 17, HCDR2 sequence comprising SEQ ID NO: 20, and HCDR3 sequence comprising SEQ ID NO: 19; and the VL region comprises LCDR1 sequence comprising SEQ ID NO: 22 or 27, LCDR2 sequence SEQ ID NO: 23, 25 or 28, and LCDR3 sequence QHFWGTPLTX$_6$ (SEQ ID NO: 112), wherein $X_6$ is present or absence, and if present, is F.

In some instances, the anti-transferrin receptor antibody comprises a VH region and a VL region, in which the VH region comprises HCDR1 sequence comprising SEQ ID NO: 17, HCDR2 sequence comprising SEQ ID NO: 20, and HCDR3 sequence comprising SEQ ID NO: 19; and the VL region comprises LCDR1 sequence comprising SEQ ID NO: 22, LCDR2 sequence AATNLA$X_5$ (SEQ ID NO: 113), and LCDR3 sequence QHFWGTPLT$X_6$ (SEQ ID NO: 112), wherein $X_5$ is selected from D or E and $X_6$ is present or absence, and if present, is F.

In some instances, the anti-transferrin receptor antibody comprises a VH region and a VL region, in which the VH region comprises HCDR1 sequence comprising SEQ ID NO: 17, HCDR2 sequence comprising SEQ ID NO: 20, and HCDR3 sequence comprising SEQ ID NO: 19; and the VL region comprises LCDR1 sequence comprising SEQ ID NO: 22, LCDR2 sequence comprising SEQ ID NO: 23, and LCDR3 sequence comprising SEQ ID NO: 24.

In some instances, the anti-transferrin receptor antibody comprises a VH region and a VL region, in which the VH region comprises HCDR1 sequence comprising SEQ ID NO: 17, HCDR2 sequence comprising SEQ ID NO: 20, and HCDR3 sequence comprising SEQ ID NO: 19; and the VL region comprises LCDR1 sequence comprising SEQ ID NO: 22, LCDR2 sequence comprising SEQ ID NO: 25, and LCDR3 sequence comprising SEQ ID NO:26.

In some instances, the anti-transferrin receptor antibody comprises a VH region and a VL region, in which the VH region comprises HCDR1 sequence comprising SEQ ID NO: 17, HCDR2 sequence comprising SEQ ID NO: 20, and HCDR3 sequence comprising SEQ ID NO: 19; and the VL region comprises LCDR1 sequence comprising SEQ ID NO: 27, LCDR2 sequence comprising SEQ ID NO: 28, and LCDR3 sequence comprising SEQ ID NO: 26.

In some instances, the anti-transferrin receptor antibody comprises a VH region and a VL region, in which the VH region comprises HCDR1 sequence comprising SEQ ID NO: 17, HCDR2 sequence comprising SEQ ID NO: 21, and HCDR3 sequence comprising SEQ ID NO: 19; and the VL region comprises LCDR1 sequence RTSENIY$X_3$NLA (SEQ ID NO: 110), LCDR2 sequence comprising SEQ ID NO: 23, 25, or 28, and LCDR3 sequence comprising SEQ ID NO: 24 or 26, wherein $X_3$ is selected from N or S.

In some instances, the anti-transferrin receptor antibody comprises a VH region and a VL region, in which the VH region comprises HCDR1 sequence comprising SEQ ID NO: 17, HCDR2 sequence comprising SEQ ID NO: 21, and HCDR3 sequence comprising SEQ ID NO: 19; and the VL region comprises LCDR1 sequence comprising SEQ ID NO: 22 or 27, LCDR2 sequence A$X_4$TNLA$X_5$ (SEQ ID NO: 111), and LCDR3 sequence comprising SEQ ID NO: 24 or 26, wherein $X_4$ is selected from A or G, and $X_5$ is selected from D or E.

In some instances, the anti-transferrin receptor antibody comprises a VH region and a VL region, in which the VH region comprises HCDR1 sequence comprising SEQ ID NO: 17, HCDR2 sequence comprising SEQ ID NO: 21, and HCDR3 sequence comprising SEQ ID NO: 19; and the VL region comprises LCDR1 sequence comprising SEQ ID NO: 22 or 27, LCDR2 sequence SEQ ID NO: 23, 25, or 28, and LCDR3 sequence QHFWGTPLT$X_6$ (SEQ ID NO: 112), wherein $X_6$ is present or absence, and if present, is F.

In some instances, the anti-transferrin receptor antibody comprises a VH region and a VL region, in which the VH region comprises HCDR1 sequence comprising SEQ ID NO: 17, HCDR2 sequence comprising SEQ ID NO: 21, and HCDR3 sequence comprising SEQ ID NO: 19, and the VL region comprises LCDR1 sequence comprising SEQ ID NO: 22, LCDR2 sequence AATNLA$X_5$ (SEQ ID NO: 113), and LCDR3 sequence QHFWGTPLT$X_6$ (SEQ ID NO: 112), wherein $X_5$ is selected from D or E and $X_6$ is present or absence, and if present, is F.

In some instances, the anti-transferrin receptor antibody comprises a VH region and a VL region, in which the VH region comprises HCDR1 sequence comprising SEQ ID NO: 17, HCDR2 sequence comprising SEQ ID NO: 21, and HCDR3 sequence comprising SEQ ID NO: 19; and the VL region comprises LCDR1 sequence comprising SEQ ID NO: 22, LCDR2 sequence comprising SEQ ID NO: 23, and LCDR3 sequence comprising SEQ ID NO: 24.

In some instances, the anti-transferrin receptor antibody comprises a VH region and a VL region, in which the VH region comprises HCDR1 sequence comprising SEQ ID NO: 17, HCDR2 sequence comprising SEQ ID NO: 21, and HCDR3 sequence comprising SEQ ID NO: 19; and the VL region comprises LCDR1 sequence comprising SEQ ID NO: 22, LCDR2 sequence comprising SEQ ID NO: 25, and LCDR3 sequence comprising SEQ ID NO: 26.

In some instances, the anti-transferrin receptor antibody comprises a VH region and a VL region, in which the VH region comprises HCDR1 sequence comprising SEQ ID NO: 17, HCDR2 sequence comprising SEQ ID NO: 21, and HCDR3 sequence comprising SEQ ID NO: 19; and the VL region comprises LCDR1 sequence comprising SEQ ID NO: 27, LCDR2 sequence comprising SEQ ID NO: 28, and LCDR3 sequence comprising SEQ ID NO: 26.

In some embodiments, the anti-transferrin receptor antibody comprises a VH region and a VL region in which the sequence of the VH region comprises about 80%, 85%, 90%, 95%, 96% 97%, 98%, 99%, or 100% sequence identity to SEQ ID NOs: 29-33 and the sequence of the VL region comprises about 80%, 85%, 90%, 95%, 96% 97%, 98%, 99%, or 100% sequence identity to SEQ ID NOs: 34-38.

In some embodiments, the VH region comprises a sequence selected from SEQ ID NOs: 29-33 (Table 4) and the VL region comprises a sequence selected from SEQ ID NOs: 34-38 (Table 5). The underlined regions in Table 4 and Table 5 denote the respective CDR1, CDR2, or CDR3 sequence.

TABLE 4

| NAME | VH SEQUENCE | SEQ ID NO: |
|---|---|---|
| 13E4_VH1 | QVQLVQSGAEVKKPGASVKVSCKASGYTFTNYWMHWVRQAPGQGLEW<br>MGEINPINGRSNYAQKFQGRVTLTVDTSISTAYMELSRLRSDDTAVYYCA<br>RGTRAMHYWGQGTLVTVSS | 29 |
| 13E4_VH2 | QVQLVQSGAEVKKPGASVKVSCKASGYTFTNYWMHWVRQAPGQGLEW<br>IGEINPINGRSNYAEKFQGRVTLTVDTSSSTAYMELSRLRSDDTAVYYCAR<br>GTRAMHYWGQGTLVTVSS | 30 |
| 13E4_VH3 | QVQLVQSGAEVKKPGASVKVSCKASGYTFTNYWMHWVRQAPGQGLEW<br>MGEINPIQGRSNYAEKFQGRVTLTVDTSSSTAYMELSSLRSEDTATYYCA<br>RGTRAMHYWGQGTLVTVSS | 31 |

TABLE 4-continued

| NAME | VH SEQUENCE | SEQ ID NO: |
|---|---|---|
| 13E4_VH4 | QVQLVQSGAEVKKPGASVKVSCKASGYTFTNYWMHWVRQAPGQGLEW MGEINPINGRSNYAEKFQGRVTLTVDTSSSTAYMELSSLRSEDTATYYCA RGTRAMHYWGQGTLVTVSS | 32 |
| 13E4_VH | QVQLQQPGAELVKPGASVKLSCKASGYTFTNYWMHWVKQRPGQGLEWI GEINPINGRSNYGERFKTKATLTVDKSSSTAYMQLSSLTSEDSAVYYCAR GTRAMHYWGQGTSVTVSS | 33 |

TABLE 5

| NAME | VL SEQUENCE | SEQ ID NO: |
|---|---|---|
| 13E4_VL1 | DIQMTQSPSSLSASVGDRVTITCRTSENIYNNLAWYQQKPGKSPKLLIYAA TNLADGVPSRFSGSGSGTDYTLTISSLQPEDFATYYCQHFWGTPLTFGGGT KVEIK | 34 |
| 13E4_VL2 | DIQMTQSPSSLSASVGDRVTITCRTSENIYNNLAWYQQKPGKAPKLLIYA ATNLADGVPSRFSGSGSGTDYTLTISSLQPEDFATYYCQHFWGTPLTFGG GTKVEIK | 35 |
| 13E4_VL3 | DIQMTQSPSSLSASVGDRVTITCRTSENIYNNLAWYQQKPGKAPKLLIYA ATNLAEGVPSRFSGSGSGTDYTLTISSLQPEDFATYYCQHFWGTPLTFGGG TKVEIK | 36 |
| 13E4_VL4 | DIQMTQSPSSLSASVGDRVTITCRTSENIYSNLAWYQQKPGKAPKLLIYAG TNLADGVPSRFSGSGSGTDYTLTISSLQPEDFANYYCQHFWGTPLTFGGG TKVEIK | 37 |
| 13E4_VL | DIQMTQSPASLSVSVGETVTITCRTSENIYNNLAWYQQKQGKSPQLLVYA ATNLADGVPSRFSGSGSGTQYSLKINSLQSEDFGNYYCQHFWGTPLTFGA GTKLELK | 38 |

In some embodiments, the anti-transferrin receptor antibody comprises a VH region and a VL region as illustrated in Table 6.

TABLE 6

| | 13E4_VH1 (SEQ ID NO: 29) | 13E4_VH2 (SEQ ID NO: 30) | 13E4_VH3 (SEQ ID NO: 31) | 13E4_VH4 (SEQ ID NO: 32) |
|---|---|---|---|---|
| 13E4_VL1 (SEQ ID NO: 34) | SEQ ID NO: 29 + SEQ ID NO: 34 | SEQ ID NO: 30 + SEQ ID NO: 34 | SEQ ID NO: 31 + SEQ ID NO: 34 | SEQ ID NO: 32 + SEQ ID NO: 34 |
| 13E4_VL2 (SEQ ID NO: 35) | SEQ ID NO: 29 + SEQ ID NO: 35 | SEQ ID NO: 30 + SEQ ID NO: 35 | SEQ ID NO: 31 + SEQ ID NO: 35 | SEQ ID NO: 32 + SEQ ID NO: 35 |
| 13E4_VL3 (SEQ ID NO: 36) | SEQ ID NO: 29 + SEQ ID NO: 36 | SEQ ID NO: 30 + SEQ ID NO: 36 | SEQ ID NO: 31 + SEQ ID NO: 36 | SEQ ID NO: 32 + SEQ ID NO: 36 |
| 13E4_VL4 (SEQ ID NO: 37) | SEQ ID NO: 29 + SEQ ID NO: 37 | SEQ ID NO: 30 + SEQ ID NO: 37 | SEQ ID NO: 31 + SEQ ID NO: 37 | SEQ ID NO: 32 + SEQ ID NO: 37 |

In some embodiments, an anti-transferrin receptor antibody described herein comprises an IgG framework, an IgA framework, an IgE framework, or an IgM framework. In some instances, the anti-transferrin receptor antibody comprises an IgG framework (e.g., IgG1, IgG2, IgG3, or IgG4). In some cases, the anti-transferrin receptor antibody comprises an IgG1 framework. In some cases, the anti-transferrin receptor antibody comprises an IgG2 (e.g., an IgG2a or IgG2b) framework. In some cases, the anti-transferrin receptor antibody comprises an IgG2a framework. In some cases, the anti-transferrin receptor antibody comprises an IgG2b framework. In some cases, the anti-transferrin receptor antibody comprises an IgG3 framework. In some cases, the anti-transferrin receptor antibody comprises an IgG4 framework.

In some cases, an anti-transferrin receptor antibody comprises one or more mutations in a framework region, e.g., in the CH1 domain, CH2 domain, CH3 domain, hinge region, or a combination thereof. In some instances, the one or more mutations are to stabilize the antibody and/or to increase half-life. In some instances, the one or more mutations are to modulate Fc receptor interactions, to reduce or eliminate Fc effector functions such as FcγR, antibody-dependent cell-mediated cytotoxicity (ADCC), or complement-dependent cytotoxicity (CDC). In additional instances, the one or more mutations are to modulate glycosylation.

In some embodiments, the one or more mutations are located in the Fc region. In some instances, the Fc region comprises a mutation at residue position L234, L235, or a combination thereof. In some instances, the mutations comprise L234 and L235. In some instances, the mutations comprise L234A and L235A. In some cases, the residue positions are in reference to IgG1.

In some instances, the Fc region comprises a mutation at residue position L234, L235, D265, N21, K46, L52, or P53, or a combination thereof. In some instances, the mutations comprise L234 and L235 in combination with a mutation at residue position K46, L52, or P53. In some cases, the Fc region comprises mutations at L234, L235, and K46. In some cases, the Fc region comprises mutations at L234, L235, and L52. In some cases, the Fc region comprises mutations at L234, L235, and P53. In some cases, the Fc region comprises mutations at D265 and N21. In some cases, the residue position is in reference to IgG1.

In some instances, the Fc region comprises L234A, L235A, D265A, N21G, K46G, L52R, or P53G, or a combination thereof. In some instances, the Fc region comprises L234A and L235A in combination with K46G, L52R, or P53G. In some cases, the Fc region comprises L234A, L235A, and K46G. In some cases, the Fc region comprises L234A, L235A, and L52R. In some cases, the Fc region comprises L234A, L235A, and P53G. In some cases, the Fc region comprises D265A and N21G. In some cases, the residue position is in reference to IgG1.

In some instances, the Fc region comprises a mutation at residue position L235, L236, D265, N21, K46, L52, or P53, or a combination of the mutations. In some instances, the Fc region comprises mutations at L235 and L236. In some instances, the Fc region comprises mutations at L235 and L236 in combination with a mutation at residue position K46, L52, or P53. In some cases, the Fc region comprises mutations at L235, L236, and K46. In some cases, the Fc region comprises mutations at L235, L236, and L52. In some cases, the Fc region comprises mutations at L235, L236, and P53. In some cases, the Fc region comprises mutations at D265 and N21. In some cases, the residue position is in reference to IgG2b.

In some embodiments, the Fc region comprises L235A, L236A, D265A, N21G, K46G, L52R, or P53G, or a combination thereof. In some instances, the Fc region comprises L235A and L236A. In some instances, the Fc region comprises L235A and L236A in combination with K46G, L52R, or P53G. In some cases, the Fc region comprises L235A, L236A, and K46G. In some cases, the Fc region comprises L235A, L236A, and L52R. In some cases, the Fc region comprises L235A, L236A, and P53G. In some cases, the Fc region comprises D265A and N21G. In some cases, the residue position is in reference to IgG2b.

In some embodiments, the Fc region comprises a mutation at residue position L233, L234, D264, N20, K45, L51, or P52, wherein the residues correspond to positions 233, 234, 264, 20, 45, 51, and 52 of SEQ ID NO: 39. In some instances, the Fc region comprises mutations at L233 and L234. In some instances, the Fc region comprises mutations at L233 and L234 in combination with a mutation at residue position K45, L51, or P52. In some cases, the Fc region comprises mutations at L233, L234, and K45. In some cases, the Fc region comprises mutations at L233, L234, and L51. In some cases, the Fc region comprises mutations at L233, L234, and K45. In some cases, the Fc region comprises mutations at L233, L234, and P52. In some instances, the Fc region comprises mutations at D264 and N20. In some cases, equivalent positions to residue L233, L234, D264, N20, K45, L51, or P52 in an IgG1, IgG2, IgG3, or IgG4 framework are contemplated. In some cases, mutations to a residue that corresponds to residue L233, L234, D264, N20, K45, L51, or P52 of SEQ ID NO: 39 in an IgG1, IgG2, or IgG4 framework are also contemplated.

In some embodiments, the Fc region comprises L233A, L234A, D264A, N20G, K45G, L51R, or P52G, wherein the residues correspond to positions 233, 234, 264, 20, 45, 51, and 52 of SEQ ID NO: 39. In some instances, the Fc region comprises L233A and L234A. In some instances, the Fc region comprises L233A and L234A in combination with K45G, L51R, or P52G. In some cases, the Fc region comprises L233A, L234A, and K45G. In some cases, the Fc region comprises L233A, L234A, and L51R. In some cases, the Fc region comprises L233A, L234A, and K45G. In some cases, the Fc region comprises L233A, L234A, and P52G. In some instances, the Fc region comprises D264A and N20G.

In some embodiments, the human IgG constant region is modified to alter antibody-dependent cellular cytotoxicity (ADCC) and/or complement-dependent cytotoxicity (CDC), e.g., with an amino acid modification described in Natsume et al., 2008 *Cancer Res,* 68 (10): 3863-72; Idusogie et al., 2001 *J Immunol,* 166 (4): 2571-5; Moore et al., 2010 *mAbs,* 2 (2): 181-189; Lazar et al., 2006 *PNAS,* 103 (11): 4005-4010, Shields et al., 2001 *JBC,* 276 (9): 6591-6604; Stavenhagen et al., 2007 *Cancer Res,* 67 (18): 8882-8890; Stavenhagen et al., 2008 *Advan. Enzyme Regul.,* 48:152-164; Alegre et al, 1992 *J Immunol,* 148:3461-3468; Reviewed in Kaneko and Niwa, 2011 Biodrugs, 25 (1): 1-11.

In some embodiments, an anti-transferrin receptor antibody described herein is a full-length antibody, comprising a heavy chain (HC) and a light chain (LC). In some cases, the heavy chain (HC) comprises a sequence selected from Table 7. In some cases, the light chain (LC) comprises a sequence selected from Table 8. The underlined region denotes the respective CDRs.

TABLE 7

| NAME | HC SEQUENCE | SEQ ID NO: |
|---|---|---|
| 13E4_VH1 | QVQLVQSGAEVKKPGASVKVSCKASGYTFTNYWMHWVRQAPGQGLE<br>WMGEINPINGRSNYAQKFQGRVTLTVDTSISTAYMELSRLRSDDTAVY<br>YCARGTRAMHYWGQGTLVTVSSASTKGPSVFPLAPSSKSTSGGTAALG<br>CLVKDYFPEPVTVSWNSGALTSGVHTFPAVLQSSGLYSLSSVVTVPSSS<br>LGTQTYICNVNHKPSNTKVDKRVEPKSCDKTHTCPPCPAPELLGGPSVF<br>LFPPKPKDTLMISRTPEVTCVVVDVSHEDPEVKFNWYVDGVEVHNAKT<br>KPREEQYNSTYRVVSVLTVLHQDWLNGKEYKCKVSNKALPAPIEKTIS<br>KAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPG | 39 |
| 13E4_VH1_a | QVQLVQSGAEVKKPGASVKVSCKASGYTFTNYWMHWVRQAPGQGLE<br>WMGEINPINGRSNYAQKFQGRVTLTVDTSISTAYMELSRLRSDDTAVY<br>YCARGTRAMHYWGQGTLVTVSSASTKGPSVFPLAPSSKSTSGGTAALG | 40 |

TABLE 7-continued

| NAME | HC SEQUENCE | SEQ ID NO: |
|---|---|---|
| | CLVKDYFPEPVTVSWNSGALTSGVHTFPAVLQSSGLYSLSSVVTVPSSS<br>LGTQTYICNVNHKPSNTKVDKRVEPKSCDKTHTCPPCPAPE**AA**GGPSVF<br>LFPPKPKDTLMISRTPEVTCVVVDVSHEDPEVKFNWYVDGVEVHNAKT<br>KPREEQYNSTYRVVSVLTVLHQDWLNGKEYKCKVSNKALPAPIEKTIS<br>KAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPG | |
| 13E4_VH1_b | QVQLVQSGAEVKKPGASVKVSCKASGYTFTNYWMHWVRQAPGQGLE<br>WMGEINPINGRSNYAQKFQGRVTLTVDTSISTAYMELSRLRSDDTAVY<br>YCARGTRAMHYWGQGTLVTVSSASTKGPSVFPLAPSSKSTSGGTAALG<br>CLVKDYFPEPVTVSWNSGALTSGVHTFPAVLQSSGLYSLSSVVTVPSSS<br>LGTQTYICNVNHKPSNTKVDKRVEPKSCDKTHTCPPCPAPE**AA**GGPSVF<br>LFPPKPKDTLMISRTPEVTCVVVDVSHEDPEVKFNWYVDGVEVHNAKT<br>KPREEQYNSTYRVVSVLTVLHQDWLNGKEYKC-VSNKALPAPIEKTIS<br>KAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPG | 41 |
| 13E4_VH1_c | QVQLVQSGAEVKKPGASVKVSCKASGYTFTNYWMHWVRQAPGQGLE<br>WMGEINPINGRSNYAQKFQGRVTLTVDTSISTAYMELSRLRSDDTAVY<br>YCARGTRAMHYWGQGTLVTVSSASTKGPSVFPLAPSSKSTSGGTAALG<br>CLVKDYFPEPVTVSWNSGALTSGVHTFPAVLQSSGLYSLSSVVTVPSSS<br>LGTQTYICNVNHKPSNTKVDKRVEPKSCDKTHTCPPCPAPE**AA**GGPSVF<br>LFPPKPKDTLMISRTPEVTCVVVDVSHEDPEVKFNWYVDGVEVHNAKT<br>KPREEQYNSTYRVVSVLTVLHQDWLNGKEYKCKVSNKA**R**PAPIEKTIS<br>KAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPG | 42 |
| 13E4_VH1_d | QVQLVQSGAEVKKPGASVKVSCKASGYTFTNYWMHWVRQAPGQGLE<br>WMGEINPINGRSNYAQKFQGRVTLTVDTSISTAYMELSRLRSDDTAVY<br>YCARGTRAMHYWGQGTLVTVSSASTKGPSVFPLAPSSKSTSGGTAALG<br>CLVKDYFPEPVTVSWNSGALTSGVHTFPAVLQSSGLYSLSSVVTVPSSS<br>LGTQTYICNVNHKPSNTKVDKRVEPKSCDKTHTCPPCPAPE**AA**GGPSVF<br>LFPPKPKDTLMISRTPEVTCVVVDVSHEDPEVKFNWYVDGVEVHNAKT<br>KPREEQYNSTYRVVSVLTVLHQDWLNGKEYKCKVSNKAL**G**APIEKTIS<br>KAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPG | 43 |
| 13E4_VH1_e | QVQLVQSGAEVKKPGASVKVSCKASGYTFTNYWMHWVRQAPGQGLE<br>WMGEINPINGRSNYAQKFQGRVTLTVDTSISTAYMELSRLRSDDTAVY<br>YCARGTRAMHYWGQGTLVTVSSASTKGPSVFPLAPSSKSTSGGTAALG<br>CLVKDYFPEPVTVSWNSGALTSGVHTFPAVLQSSGLYSLSSVVTVPSSS<br>LGTQTYICNVNHKPSNTKVDKRVEPKSCDKTHTCPPCPAPELLGGPSVF<br>LFPPKPKDTLMISRTPEVTCVVV**A**VSHEDPEVKFNWYVDGVEVHNAKT<br>KPREEQY**G**STYRVVSVLTVLHQDWLNGKEYKCKVSNKALPAPIEKTIS<br>KAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPG | 44 |
| 13E4_VH2 | QVQLVQSGAEVKKPGASVKVSCKASGYTFTNYWMHWVRQAPGQGLE<br>WIGEINPINGRSNYAEKFQGRVTLTVDTSSSTAYMELSRLRSDDTAVYY<br>CARGTRAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPELLGGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 45 |
| 13E4_VH2_a | QVQLVQSGAEVKKPGASVKVSCKASGYTFTNYWMHWVRQAPGQGLE<br>WIGEINPINGRSNYAEKFQGRVTLTVDTSSSTAYMELSRLRSDDTAVYY<br>CARGTRAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPE**AA**GGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 46 |
| 13E4_VH2_b | QVQLVQSGAEVKKPGASVKVSCKASGYTFTNYWMHWVRQAPGQGLE<br>WIGEINPINGRSNYAEKFQGRVTLTVDTSSSTAYMELSRLRSDDTAVYY<br>CARGTRAMHYWGQGTLVTVSSASTKGPSVFPLAPSSKSTSGGTAALGC | 47 |

TABLE 7-continued

| NAME | HC SEQUENCE | SEQ ID NO: |
|---|---|---|
| | LVKDYFPEPVTVSWNSGALTSGVHTFPAVLQSSGLYSLSSVVTVPSSSL<br>GTQTYICNVNHKPSNTKVDKRVEPKSCDKTHTCPPCPAPE**AA**GGPSVFL<br>FPPKPKDTLMISRTPEVTCVVVDVSHEDPEVKFNWYVDGVEVHNAKTK<br>PREEQYNSTYRVVSVLTVLHQDWLNGKEYKC**G**VSNKALPAPIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | |
| 13E4_VH2_c | QVQLVQSGAEVKKPGASVKVSCKASGYTFTNYWMHWVRQAPGQGLE<br>WIGEINPINGRSNYAEKFQGRVTLTVDTSSSTAYMELSRLRSDDTAVYY<br>CARGTRAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPE**AA**GGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKA**R**PAPIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 48 |
| 13E4_VH2_d | QVQLVQSGAEVKKPGASVKVSCKASGYTFTNYWMHWVRQAPGQGLE<br>WIGEINPINGRSNYAEKFQGRVTLTVDTSSSTAYMELSRLRSDDTAVYY<br>CARGTRAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPE**AA**GGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKAL**G**APIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 49 |
| 13E4_VH2_e | QVQLVQSGAEVKKPGASVKVSCKASGYTFTNYWMHWVRQAPGQGLE<br>WIGEINPINGRSNYAEKFQGRVTLTVDTSSSTAYMELSRLRSDDTAVYY<br>CARGTRAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPELLGGPSVFL<br>FPPKPKDTLMISRTPEVTCVVV**A**VSHEDPEVKFNWYVDGVEVHNAKTK<br>PREEQY**G**STYRVVSVLTVLHQDWLNGKEYKCKVSNKALPAPIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 50 |
| 13E4_VH3 | QVQLVQSGAEVKKPGASVKVSCKASGYTFTNYWMHWVRQAPGQGLE<br>WMGEINPIQGRSNYAEKFQGRVTLTVDTSSSTAYMELSSLRSEDTATYY<br>CARGTRAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPELLGGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 51 |
| 13E4_VH3_a | QVQLVQSGAEVKKPGASVKVSCKASGYTFTNYWMHWVRQAPGQGLE<br>WMGEINPIQGRSNYAEKFQGRVTLTVDTSSSTAYMELSSLRSEDTATYY<br>CARGTRAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPE**AA**GGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 52 |
| 13E4_VH3_b | QVQLVQSGAEVKKPGASVKVSCKASGYTFTNYWMHWVRQAPGQGLE<br>WMGEINPIQGRSNYAEKFQGRVTLTVDTSSSTAYMELSSLRSEDTATYY<br>CARGTRAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPE**AA**GGPSVFL<br>FPPKPKDTLMISRTPEVTCVVVDVSHEDPEVKFNWYVDGVEVHNAKTK<br>PREEQYNSTYRVVSVLTVLHQDWLNGKEYKC**G**VSNKALPAPIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 53 |
| 13E4_VH3_c | QVQLVQSGAEVKKPGASVKVSCKASGYTFTNYWMHWVRQAPGQGLE<br>WMGEINPIQGRSNYAEKFQGRVTLTVDTSSSTAYMELSSLRSEDTATYY<br>CARGTRAMHYWGQGTLVTVSSASTKGPSVFPLAPSSKSTSGGTAALGC | 54 |

TABLE 7-continued

| NAME | HC SEQUENCE | SEQ ID NO: |
|---|---|---|
| | LVKDYFPEPVTVSWNSGALTSGVHTFPAVLQSSGLYSLSSVVTVPSSSL<br>GTQTYICNVNHKPSNTKVDKRVEPKSCDKTHTCPPCPAPE**AA**GGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKA**R**PAPIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | |
| 13E4_VH3_d | QVQLVQSGAEVKKPGASVKVSCKASGYTFTNYWMHWVRQAPGQGLE<br>WMGEINPIQGRSNYAEKFQGRVTLTVDTSSSTAYMELSSLRSEDTATYY<br>CARGTRAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPE**AA**GGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKAL**G**APIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 55 |
| 13E4_VH3_e | QVQLVQSGAEVKKPGASVKVSCKASGYTFTNYWMHWVRQAPGQGLE<br>WMGEINPIQGRSNYAEKFQGRVTLTVDTSSSTAYMELSSLRSEDTATYY<br>CARGTRAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPELLGGPSVFL<br>FPPKPKDTLMISRTPEVTCVVV**A**VSHEDPEVKFNWYVDGVEVHNAKTK<br>PREEQY**G**STYRVVSVLTVLHQDWLNGKEYKCKVSNKALPAPIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 56 |
| 13E4_VH4 | QVQLVQSGAEVKKPGASVKVSCKASGYTFTNYWMHWVRQAPGQGLE<br>WMGEINPINGRSNYAEKFQGRVTLTVDTSSSTAYMELSSLRSEDTATYY<br>CARGTRAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPELLGGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 57 |
| 13E4_VH4_a | QVQLVQSGAEVKKPGASVKVSCKASGYTFTNYWMHWVRQAPGQGLE<br>WMGEINPINGRSNYAEKFQGRVTLTVDTSSSTAYMELSSLRSEDTATYY<br>CARGTRAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPE**AA**GGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 58 |
| 13E4_VH4_b | QVQLVQSGAEVKKPGASVKVSCKASGYTFTNYWMHWVRQAPGQGLE<br>WMGEINPINGRSNYAEKFQGRVTLTVDTSSSTAYMELSSLRSEDTATYY<br>CARGTRAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPE**AA**GGPSVFL<br>FPPKPKDTLMISRTPEVTCVVVDVSHEDPEVKFNWYVDGVEVHNAKTK<br>PREEQYNSTYRVVSVLTVLHQDWLNGKEYKC**G**VSNKALPAPIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 59 |
| 13E4_VH4_c | QVQLVQSGAEVKKPGASVKVSCKASGYTFTNYWMHWVRQAPGQGLE<br>WMGEINPINGRSNYAEKFQGRVTLTVDTSSSTAYMELSSLRSEDTATYY<br>CARGTRAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPE**AA**GGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKA**R**PAPIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 60 |
| 13E4_VH4_d | QVQLVQSGAEVKKPGASVKVSCKASGYTFTNYWMHWVRQAPGQGLE<br>WMGEINPINGRSNYAEKFQGRVTLTVDTSSSTAYMELSSLRSEDTATYY<br>CARGTRAMHYWGQGTLVTVSSASTKGPSVFPLAPSSKSTSGGTAALGC | 61 |

TABLE 7-continued

| NAME | HC SEQUENCE | SEQ ID NO: |
|---|---|---|
| | LVKDYFPEPVTVSWNSGALTSGVHTFPAVLQSSGLYSLSSVVTVPSSSL<br>GTQTYICNVNHKPSNTKVDKRVEPKSCDKTHTCPPCPAPE**AA**GGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKAL**G**APIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | |
| 13E4_VH4_e | QVQLVQSGAEVKKPGASVKVSCKASGYTFTNYWMHWVRQAPGQGLE<br>WMGEINPINGRSNYAEKFQGRVTLTVDTSSSTAYMELSSLRSEDTATYY<br>CARGTRAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPELLGGPSVFL<br>FPPKPKDTLMISRTPEVTCVVVAVSHEDPEVKFNWYVDGVEVHNAKTK<br>PREEQYGSTYRVVSVLTVLHQDWLNGKEYKCKVSNKALPAPIEKTISK<br>AKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 62 |

TABLE 8

| NAME | LC SEQUENCE | SEQ ID NO: |
|---|---|---|
| 13E4_VL1 | DIQMTQSPSSLSASVGDRVTITCRTSENIYNNLAWYQQKPGKSPKLLIYA<br>ATNLADGVPSRFSGSGSGTDYTLTISSLQPEDFATYYCQHFWGTPLTFG<br>GGTKVEIKRTVAAPSVFIFPPSDEQLKSGTASVVCLLNNFYPREAKVQW<br>KVDNALQSGNSQESVTEQDSKDSTYSLSSTLTLSKADYEKHKVYACEV<br>THQGLSSPVTKSFNRGEC | 63 |
| 13E4_VL2 | DIQMTQSPSSLSASVGDRVTITCRTSENIYNNLAWYQQKPGKAPKLLIY<br>AATNLADGVPSRFSGSGSGTDYTLTISSLQPEDFATYYCQHFWGTPLTF<br>GGGTKVEIKRTVAAPSVFIFPPSDEQLKSGTASVVCLLNNFYPREAKVQ<br>WKVDNALQSGNSQESVTEQDSKDSTYSLSSTLTLSKADYEKHKVYACE<br>VTHQGLSSPVTKSFNRGEC | 64 |
| 13E4_VL3 | DIQMTQSPSSLSASVGDRVTITCRTSENIYNNLAWYQQKPGKAPKLLIY<br>AATNLAEGVPSRFSGSGSGTDYTLTISSLQPEDFATYYCQHFWGTPLTF<br>GGGTKVEIKRTVAAPSVFIFPPSDEQLKSGTASVVCLLNNFYPREAKVQ<br>WKVDNALQSGNSQESVTEQDSKDSTYSLSSTLTLSKADYEKHKVYACE<br>VTHQGLSSPVTKSFNRGEC | 65 |
| 13E4_VL4 | DIQMTQSPSSLSASVGDRVTITCRTSENIYSNLAWYQQKPGKAPKLLIYA<br>GTNLADGVPSRFSGSGSGTDYTLTISSLQPEDFANYYCQHFWGTPLTFG<br>GGTKVEIKRTVAAPSVFIFPPSDEQLKSGTASVVCLLNNFYPREAKVQW<br>KVDNALQSGNSQESVTEQDSKDSTYSLSSTLTLSKADYEKHKVYACEV<br>THQGLSSPVTKSFNRGEC | 66 |

In some embodiments, an anti-transferrin receptor antibody described herein has an improved serum half-life compared to a reference anti-transferrin receptor antibody. In some instances, the improved serum half-life is at least 30 minutes, 1 hour, 1.5 hour, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, 14 days, 30 days, or longer than reference anti-transferrin receptor antibody.

In some embodiments, the binding moiety A is conjugated to a polynucleic acid molecule (B) non-specifically. In some instances, the binding moiety A is conjugated to a polynucleic acid molecule (B) via a lysine residue or a cysteine residue, in a non-site specific manner. In some instances, the binding moiety A is conjugated to a polynucleic acid molecule (B) via a lysine residue (e.g., lysine residue present in the binding moiety A) in a non-site specific manner. In some cases, the binding moiety A is conjugated to a polynucleic acid molecule (B) via a cysteine residue (e.g., cysteine residue present in the binding moiety A) in a non-site specific manner.

In some embodiments, the binding moiety A is conjugated to a polynucleic acid molecule (B) in a site-specific manner. In some instances, the binding moiety A is conjugated to a polynucleic acid molecule (B) through a lysine residue, a cysteine residue, at the 5'-terminus, at the 3'-terminus, an unnatural amino acid, or an enzyme-modified or enzyme-catalyzed residue, via a site-specific manner. In some instances, the binding moiety A is conjugated to a polynucleic acid molecule (B) through a lysine residue (e.g., lysine residue present in the binding moiety A) via a site-specific manner. In some instances, the binding moiety A is conjugated to a polynucleic acid molecule (B) through a cysteine residue (e.g., cysteine residue present in the binding moiety A) via a site-specific manner. In some instances, the binding moiety A is conjugated to a polynucleic acid molecule (B) at the 5'-terminus via a site-specific manner. In some instances, the binding moiety A is conjugated to a polynucleic acid molecule (B) at the 3'-terminus via a site-specific manner. In some instances, the binding moiety A is conjugated to a polynucleic acid molecule (B) through an unnatural amino acid via a site-specific manner. In some instances, the binding moiety A is conjugated to a polynucleic acid molecule (B) through an enzyme-modified or enzyme-catalyzed residue via a site-specific manner.

In some embodiments, one or more polynucleic acid molecule (B) is conjugated to a binding moiety A. In some instances, about 1, 2, 3, 4, 5, 6, 7, 8, 9, 10, 11, 12, 13, 14, 15, 16, or more polynucleic acid molecules are conjugated to one binding moiety A. In some instances, about 1 polynucleic acid molecule is conjugated to one binding moiety A. In some instances, about 2 polynucleic acid molecules are conjugated to one binding moiety A. In some instances, about 3 polynucleic acid molecules are conjugated to one binding moiety A. In some instances, about 4 polynucleic acid molecules are conjugated to one binding moiety A. In some instances, about 5 polynucleic acid molecules are conjugated to one binding moiety A. In some instances, about 6 polynucleic acid molecules are conjugated to one binding moiety A. In some instances, about 7 polynucleic acid molecules are conjugated to one binding moiety A. In some instances, about 8 polynucleic acid molecules are conjugated to one binding moiety A. In some instances, about 9 polynucleic acid molecules are conjugated to one binding moiety A. In some instances, about 10 polynucleic acid molecules are conjugated to one binding moiety A. In some instances, about 11 polynucleic acid molecules are conjugated to one binding moiety A. In some instances, about 12 polynucleic acid molecules are conjugated to one binding moiety A. In some instances, about 13 polynucleic acid molecules are conjugated to one binding moiety A. In some instances, about 14 polynucleic acid molecules are conjugated to one binding moiety A. In some instances, about 15 polynucleic acid molecules are conjugated to one binding moiety A. In some instances, about 16 polynucleic acid molecules are conjugated to one binding moiety A. In some cases, the one or more polynucleic acid molecules are the same. In other cases, the one or more polynucleic acid molecules are different.

In some embodiments, the number of polynucleic acid molecule (B) conjugated to a binding moiety A forms a ratio. In some instances, the ratio is referred to as a DAR (drug-to-antibody) ratio, in which the drug as referred to herein is the polynucleic acid molecule (B). In some instances, the DAR ratio of the polynucleic acid molecule (B) to binding moiety A is about 1, 2, 3, 4, 5, 6, 7, 8, 9, 10, 11, 12, 13, 14, 15, 16, or greater. In some instances, the DAR ratio of the polynucleic acid molecule (B) to binding moiety A is about 1 or greater. In some instances, the DAR ratio of the polynucleic acid molecule (B) to binding moiety A is about 2 or greater. In some instances, the DAR ratio of the polynucleic acid molecule (B) to binding moiety A is about 3 or greater. In some instances, the DAR ratio of the polynucleic acid molecule (B) to binding moiety A is about 4 or greater. In some instances, the DAR ratio of the polynucleic acid molecule (B) to binding moiety A is about 5 or greater. In some instances, the DAR ratio of the polynucleic acid molecule (B) to binding moiety A is about 6 or greater. In some instances, the DAR ratio of the polynucleic acid molecule (B) to binding moiety A is about 7 or greater. In some instances, the DAR ratio of the polynucleic acid molecule (B) to binding moiety A is about 8 or greater. In some instances, the DAR ratio of the polynucleic acid molecule (B) to binding moiety A is about 9 or greater. In some instances, the DAR ratio of the polynucleic acid molecule (B) to binding moiety A is about 10 or greater. In some instances, the DAR ratio of the polynucleic acid molecule (B) to binding moiety A is about 11 or greater. In some instances, the DAR ratio of the polynucleic acid molecule (B) to binding moiety A is about 12 or greater.

In some instances, the DAR ratio of the polynucleic acid molecule (B) to binding moiety A is about 1, 2, 3, 4, 5, 6, 7, 8, 9, 10, 11, 12, 13, 14, 15, or 16. In some instances, the DAR ratio of the polynucleic acid molecule (B) to binding moiety A is about 1. In some instances, the DAR ratio of the polynucleic acid molecule (B) to binding moiety A is about 2. In some instances, the DAR ratio of the polynucleic acid molecule (B) to binding moiety A is about 3. In some instances, the DAR ratio of the polynucleic acid molecule (B) to binding moiety A is about 4. In some instances, the DAR ratio of the polynucleic acid molecule (B) to binding moiety A is about 5. In some instances, the DAR ratio of the polynucleic acid molecule (B) to binding moiety A is about 6. In some instances, the DAR ratio of the polynucleic acid molecule (B) to binding moiety A is about 7. In some instances, the DAR ratio of the polynucleic acid molecule (B) to binding moiety A is about 8. In some instances, the DAR ratio of the polynucleic acid molecule (B) to binding moiety A is about 9. In some instances, the DAR ratio of the polynucleic acid molecule (B) to binding moiety A is about 10. In some instances, the DAR ratio of the polynucleic acid molecule (B) to binding moiety A is about 11. In some instances, the DAR ratio of the polynucleic acid molecule (B) to binding moiety A is about 12. In some instances, the DAR ratio of the polynucleic acid molecule (B) to binding moiety A is about 13. In some instances, the DAR ratio of the polynucleic acid molecule (B) to binding moiety A is about 14. In some instances, the DAR ratio of the polynucleic acid molecule (B) to binding moiety A is about 15. In some instances, the DAR ratio of the polynucleic acid molecule (B) to binding moiety A is about 16.

In some instances, the DAR ratio of the polynucleic acid molecule (B) to binding moiety A is 1, 2, 3, 4, 5, 6, 7, 8, 9, 10, 11, 12, 13, 14, 15, or 16. In some instances, the DAR ratio of the polynucleic acid molecule (B) to binding moiety A is 1. In some instances, the DAR ratio of the polynucleic acid molecule (B) to binding moiety A is 2. In some instances, the DAR ratio of the polynucleic acid molecule (B) to binding moiety A is 4. In some instances, the DAR ratio of the polynucleic acid molecule (B) to binding moiety A is 6. In some instances, the DAR ratio of the polynucleic acid molecule (B) to binding moiety A is 8. In some instances, the DAR ratio of the polynucleic acid molecule (B) to binding moiety A is 12.

In some instances, a conjugate comprising polynucleic acid molecule (B) and binding moiety A has improved activity as compared to a conjugate comprising polynucleic acid molecule (B) without a binding moiety A. In some instances, improved activity results in enhanced biologically relevant functions, e.g., improved stability, affinity, binding, functional activity, and efficacy in treatment or prevention of a disease state. In some instances, the disease state is a result of one or more mutated exons of a gene. In some instances, the conjugate comprising polynucleic acid molecule (B) and binding moiety A results in increased exon skipping of the one or more mutated exons as compared to the conjugate comprising polynucleic acid molecule (B) without a binding moiety A. In some instances, exon skipping is increased by at least or about 5%, 10%, 20%, 25%, 30%, 40%, 50%, 60%, 70%, 80%, 90%, 95%, or more than 95% in the conjugate comprising polynucleic acid molecule (B) and binding moiety A as compared to the conjugate comprising polynucleic acid molecule (B) without a binding moiety A.

In some embodiments, an antibody or its binding fragment is further modified using conventional techniques known in the art, for example, by using amino acid deletion, insertion, substitution, addition, and/or by recombination and/or any other modification (e.g., posttranslational and chemical modifications, such as glycosylation and phosphorylation) known in the art either alone or in combination. In some instances, the modification further comprises a modification for modulating interaction with Fc receptors. In some instances, the one or more modifications include those described in, for example, International Publication No. WO97/34631, which discloses amino acid residues involved in the interaction between the Fc domain and the FcRn receptor. Methods for introducing such modifications in the nucleic acid sequence underlying the amino acid sequence of an antibody or its binding fragment is well known to the person skilled in the art.

In some instances, an antibody binding fragment further encompasses its derivatives and includes polypeptide sequences containing at least one CDR.

In some instances, the term "single-chain" as used herein means that the first and second domains of a bi-specific single chain construct are covalently linked, preferably in the form of a co-linear amino acid sequence encodable by a single nucleic acid molecule.

In some instances, a bispecific single chain antibody construct relates to a construct comprising two antibody derived binding domains. In such embodiments, bi-specific single chain antibody construct is tandem bi-scFv or diabody. In some instances, a scFv contains a VH and VL domain connected by a linker peptide. In some instances, linkers are of a length and sequence sufficient to ensure that each of the first and second domains can, independently from one another, retain their differential binding specificities.

In some embodiments, binding to or interacting with as used herein defines a binding/interaction of at least two antigen-interaction-sites with each other. In some instances, antigen-interaction-site defines a motif of a polypeptide that shows the capacity of specific interaction with a specific antigen or a specific group of antigens. In some cases, the binding/interaction is also understood to define a specific recognition. In such cases, specific recognition refers to that the antibody or its binding fragment is capable of specifically interacting with and/or binding to at least two amino acids of each of a target molecule. For example, specific recognition relates to the specificity of the antibody molecule, or to its ability to discriminate between the specific regions of a target molecule. In additional instances, the specific interaction of the antigen-interaction-site with its specific antigen results in an initiation of a signal, e.g. due to the induction of a change of the conformation of the antigen, an oligomerization of the antigen, etc. In further embodiments, the binding is exemplified by the specificity of a "key-lock-principle". Thus in some instances, specific motifs in the amino acid sequence of the antigen-interaction-site and the antigen bind to each other as a result of their primary, secondary or tertiary structure as well as the result of secondary modifications of said structure. In such cases, the specific interaction of the antigen-interaction-site with its specific antigen results as well in a simple binding of the site to the antigen.

In some instances, specific interaction further refers to a reduced cross-reactivity of the antibody or its binding fragment or a reduced off-target effect. For example, the antibody or its binding fragment that bind to the polypeptide/protein of interest but do not or do not essentially bind to any of the other polypeptides are considered as specific for the polypeptide/protein of interest. Examples for the specific interaction of an antigen-interaction-site with a specific antigen comprise the specificity of a ligand for its receptor, for example, the interaction of an antigenic determinant (epitope) with the antigenic binding site of an antibody.

Thus, in some instances, a polynucleic acid molecule conjugate comprises polynucleic acid molecule having a sense strand having a sequence at least 80%, at least 85%, at least 90%, at least 95%, at least 99%, or 100% identical to SEQ ID NO: 1, and an antisense strand having a sequence at least 80% identical to SEQ ID NO: 2, and an anti-transferrin receptor antibody or antigen binding fragment thereof conjugated to the polynucleic acid such that the polynucleic acid molecule conjugate mediates RNA interference against the DMPK.

In certain embodiments, a polynucleic acid molecule conjugate comprises an anti-transferrin receptor antibody or antigen binding fragment thereof conjugated to a polynucleic acid molecule that hybridizes to a target sequence of DMPK, and the polynucleic acid molecule having a sense strand having a sequence at least 80%, at least 85%, at least 90%, at least 95%, at least 99%, or 100% identical to SEQ ID NO: 3, 5, 7, 9, 11, 13, or 15 and an antisense strand having a sequence of SEQ ID NO: 4, 6, 8, 10, 12, 14, or 16, and anti-transferrin receptor antibody or antigen binding fragment thereof comprises a variable heavy chain (VH) region and a variable light chain (VL) region, wherein the VH region comprises HCDR1 sequence comprising SEQ ID NO: 17, HCDR2 sequence comprising SEQ ID NO:20, and HCDR3 sequence comprising SEQ ID NO: 19; and the VL region comprises LCDR1 sequence comprising SEQ ID NO: 22, LCDR2 sequence comprising SEQ ID NO: 23, and LCDR3 sequence comprising SEQ ID NO: 24, and the anti-transferrin receptor antibody or antigen binding fragment thereof and the polynucleic acid molecule is conjugated via a linker comprising 4-(N-maleimidomethyl)cyclohexane-1-amidate (SMCC).

In certain embodiments, a polynucleic acid molecule conjugate comprises an anti-transferrin receptor antibody or antigen binding fragment thereof conjugated to a polynucleic acid molecule that hybridizes to a target sequence of DMPK, and the polynucleic acid molecule having a sense strand having a sequence at least 80%, at least 85%, at least 90%, at least 95%, at least 99%, or 100% identical to SEQ ID NO: 3, 5, 7, 9, 11, 13, or 15 and an antisense strand having a sequence of SEQ ID NO: 4, 6, 8, 10, 12, 14, or 16, and the anti-transferrin receptor antibody or antigen binding fragment thereof comprises a variable heavy chain (VH) region and a variable light chain (VL) region, wherein the VH region comprises at least 80%, 85%, 90%, 95%, 99%, or 100% sequence identity to SEQ ID NO: 30, and wherein the VL region comprises at least 80%, 85%, 90%, 95%, 99%, or 100% sequence identity to SEQ ID NO: 34, and the anti-transferrin receptor antibody or antigen binding fragment thereof and the polynucleic acid molecule is conjugated via a maleimide linker.

In certain embodiments, a polynucleic acid molecule conjugate comprises an anti-transferrin receptor antibody or antigen binding fragment thereof conjugated to a polynucleic acid molecule that hybridizes to a target sequence of DMPK, and the polynucleic acid molecule having a sense strand having a sequence at least 80%, at least 85%, at least 90%, at least 95%, at least 99%, or 100% identical to SEQ ID NO: 1, and an antisense strand having a sequence of SEQ ID NO: 2, and the sense strand comprises at least three, four, five, or six consecutive 2'-O-methyl modified nucleotides at the 5'-end and at least two, at least three 2'-F modified nucleotides, and the anti-transferrin receptor antibody or antigen binding fragment thereof comprises a variable heavy chain (VH) region and a variable light chain (VL) region, wherein the VH region comprises at least 80%, 85%, 90%, 95%, 99%, or 100% sequence identity to SEQ ID NO: 30, and wherein the VL region comprises at least 80%, 85%, 90%, 95%, 99%, or 100% sequence identity to SEQ ID NO: 34, and the anti-transferrin receptor antibody or antigen binding fragment thereof and the polynucleic acid molecule is conjugated via a maleimide linker.

In certain embodiments, a polynucleic acid molecule conjugate comprises an anti-transferrin receptor antibody or antigen binding fragment thereof conjugated to a polynucleic acid molecule that hybridizes to a target sequence of DMPK, and the polynucleic acid molecule having a sense strand having a sequence at least 80%, at least 85%, at least 90%, at least 95%, at least 99%, or 100% identical to SEQ ID NO: 1, and an antisense strand having a sequence of SEQ ID NO: 2, and the antisense strand comprises at least two, at least three, at least four, at least five consecutive 2'-O-methyl modified nucleotide at the 3'-end, and at least one, at least two, at least three, at least four 2'-F modified nucleotides, and the anti-transferrin receptor antibody or antigen binding fragment thereof comprises a variable heavy chain (VH) region and a variable light chain (VL) region, wherein the VH region comprises HCDR1 sequence comprising SEQ ID NO: 17, HCDR2 sequence comprising SEQ ID NO: 20, and HCDR3 sequence comprising SEQ ID NO: 19; and the VL region comprises LCDR1 sequence comprising SEQ ID NO: 22, LCDR2 sequence comprising SEQ ID NO: 23, and LCDR3 sequence comprising SEQ ID NO: 24, and the anti-transferrin receptor antibody or antigen binding fragment thereof and the polynucleic acid molecule is conjugated via a maleimide linker.

In certain embodiments, a polynucleic acid molecule conjugate comprises an anti-transferrin receptor antibody or antigen binding fragment thereof conjugated to a polynucleic acid molecule that hybridizes to a target sequence of DMPK, and the polynucleic acid molecule having a sense strand having a sequence at least 80%, at least 85%, at least 90%, at least 95%, at least 99%, or 100% identical to SEQ ID NO: 1, and an antisense strand having a sequence of SEQ ID NO: 2, and the antisense strand comprises 2'-O-methyl modified nucleotides at the 5'-end and at the 3'-end, and the anti-transferrin receptor antibody or antigen binding fragment thereof comprises a variable heavy chain (VH) region and a variable light chain (VL) region, and the VH region comprises HCDR1 sequence comprising SEQ ID NO: 17, HCDR2 sequence comprising SEQ ID NO: 18, and HCDR3 sequence comprising SEQ ID NO: 19; and the VL region comprises LCDR1 sequence comprising SEQ ID NO: 22, LCDR2 sequence comprising SEQ ID NO: 3, and LCDR3 sequence comprising SEQ ID NO: 24, and the anti-transferrin receptor antibody or antigen binding fragment thereof and the polynucleic acid molecule is conjugated via a maleimide linker.

In certain embodiments, a polynucleic acid molecule conjugate comprises an anti-transferrin receptor antibody or antigen binding fragment thereof conjugated to a polynucleic acid molecule that hybridizes to a target sequence of DMPK, and the polynucleic acid molecule having a sense strand having a sequence at least 80%, at least 85%, at least 90%, at least 95%, at least 99%, or 100% identical to SEQ ID NO: 1, and an antisense strand having a sequence of SEQ ID NO: 2, and the antisense strand comprises at least five consecutive 2'-O-methyl modified nucleotide at the 3'-end and four 2'-F modified nucleotides, wherein any two of the four 2'-F modified nucleotides are not consecutive, and the anti-transferrin receptor antibody or antigen binding fragment thereof comprises a variable heavy chain (VH) region and a variable light chain (VL) region, and the VH region comprises at least 80%, 85%, 90%, 95%, 99%, or 100% sequence identity to SEQ ID NO: 3, and wherein the VL region comprises at least 80%, 85%, 90%, 95%, 99%, or 100% sequence identity to SEQ ID NO: 34, and the anti-transferrin receptor antibody or antigen binding fragment thereof and the polynucleic acid molecule is conjugated via a 6-Amino-1-hexanol linker.

Additional Binding Moieties

In some embodiments, the binding moiety is a plasma protein. In some instances, the plasma protein comprises albumin. In some instances, the binding moiety A is albumin. In some instances, albumin is conjugated by one or more of a conjugation chemistry described herein to a polynucleic acid molecule. In some instances, albumin is conjugated by native ligation chemistry to a polynucleic acid molecule. In some instances, albumin is conjugated by lysine conjugation to a polynucleic acid molecule.

In some instances, the binding moiety is a steroid. Exemplary steroids include cholesterol, phospholipids, di-and triacylglycerols, fatty acids, hydrocarbons that are saturated, unsaturated, comprise substitutions, or combinations thereof. In some instances, the steroid is cholesterol. In some instances, the binding moiety is cholesterol. In some instances, cholesterol is conjugated by one or more of a conjugation chemistry described herein to a polynucleic acid molecule. In some instances, cholesterol is conjugated by native ligation chemistry to a polynucleic acid molecule. In some instances, cholesterol is conjugated by lysine conjugation to a polynucleic acid molecule.

In some instances, the binding moiety is a polymer, including but not limited to polynucleic acid molecule aptamers that bind to specific surface markers on cells. In this instance the binding moiety is a polynucleic acid that does not hybridize to a target gene or mRNA, but instead is capable of selectively binding to a cell surface marker similarly to an antibody binding to its specific epitope of a cell surface marker.

In some cases, the binding moiety is a peptide. In some cases, the peptide comprises between about 1 and about 3 kDa. In some cases, the peptide comprises between about 1.2 and about 2.8 kDa, about 1.5 and about 2.5 kDa, or about 1.5 and about 2 kDa. In some instances, the peptide is a bicyclic peptide. In some cases, the bicyclic peptide is a constrained bicyclic peptide. In some instances, the binding moiety is a bicyclic peptide (e.g., bicycles from Bicycle Therapeutics).

In additional cases, the binding moiety is a small molecule. In some instances, the small molecule is an antibody-recruiting small molecule. In some cases, the antibody-recruiting small molecule comprises a target-binding terminus and an antibody-binding terminus, in which the target-binding terminus is capable of recognizing and interacting with a cell surface receptor. For example, in some instances, the target-binding terminus comprising a glutamate urea compound enables interaction with PSMA, thereby, enhances an antibody interaction with a cell that expresses PSMA. In some instances, a binding moiety is a small molecule described in Zhang et al., "A remote arene-binding site on prostate specific membrane antigen revealed by antibody-recruiting small molecules," J Am Chem Soc. 132 (36): 12711-12716 (2010); or McEnaney, et al., "Antibody-recruiting molecules: an emerging paradigm for engaging immune function in treating human disease," ACS Chem Biol. 7 (7): 1139-1151 (2012).

Production of Antibodies or Antigen Binding Fragments Thereof

In some embodiments, polypeptides described herein (e.g., antibodies and binding fragments, anti-transferrin receptor antibody or antigen binding fragments thereof) are produced using any method known in the art to be useful for the synthesis of polypeptides (e.g., antibodies), in particular, by chemical synthesis or by recombinant expression, and are preferably produced by recombinant expression techniques.

In some instances, an antibody or antigen binding fragment thereof is expressed recombinantly, and the nucleic acid encoding the antibody or its binding fragment is assembled from chemically synthesized oligonucleotides (e.g., as described in Kutmeier et al., 1994, *BioTechniques* 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or antigen binding fragment is optionally generated by immunizing an animal, such as a rabbit, to generate polyclonal antibodies or, more preferably, by generating monoclonal antibodies, e.g., as described by Kohler and Milstein (1975, Nature 256:495-497) or, as described by Kozbor et al. (1983, *Immunology Today* 4:72) or Cole et al. (1985 in *Monoclonal Antibodies and Cancer Therapy*, Alan R. Liss, Inc., pp. 77-96). Alternatively, a clone encoding at least the Fab portion of the antibody is optionally obtained by screening Fab expression libraries (e.g., as described in Huse et al., 1989, *Science* 246:1275-1281) for clones of Fab fragments that bind the specific antigen or by screening antibody libraries (See, e.g., Clackson et al., 1991, *Nature* 352:624; Hane et al., 1997 *Proc. Natl. Acad. Sci. USA* 94:4937).

In some embodiments, techniques developed for the production of "chimeric antibodies" (Morrison et al., 1984, *Proc. Natl. Acad. Sci.* 81:851-855; Neuberger et al., 1984, *Nature* 312:604-608; Takeda et al., 1985, *Nature* 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region, e.g., humanized antibodies.

In some embodiments, techniques described for the production of single chain antibodies (U.S. Pat. No. 4,694,778; Bird, 1988, *Science* 242:423-42; Huston et al., 1988, *Proc. Natl. Acad. Sci. USA* 85:5879-5883; and Ward et al., 1989, *Nature* 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* are also optionally used (Skerra et al., 1988, *Science* 242:1038-1041).

In some embodiments, an expression vector comprising the nucleotide sequence of an antibody or the nucleotide sequence of an antibody is transferred to a host cell by conventional techniques (e.g., electroporation, liposomal transfection, and/or calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody or its binding fragment described herein. Such host-expression systems represent vehicles by which the coding sequences of the antibody is produced and subsequently purified, but also represent cells that are, when transformed or transfected with the appropriate nucleotide coding sequences, express an antibody or its binding fragment in situ. These include, but are not limited to, microorganisms such as bacteria (e.g., *E. coli* and *B. subtilis*) transformed with recombinant bacteriophage DNA, plasmid DNA or cosmid DNA expression vectors containing an antibody or its binding fragment coding sequences; yeast (e.g., *Saccharomyces Pichia*) transformed with recombinant yeast expression vectors containing an antibody or its binding fragment coding sequences; insect cell systems infected with recombinant virus expression vectors (e.g., baculovirus) containing an antibody or its binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its binding fragments.

In some instances, a number of selection systems are used, including but not limited to the herpes simplex virus thymidine kinase (Wigler et al., 1977, *Cell*11:223), hypoxanthine-guanine phosphoribosyltransferase (Szybalska & Szybalski, 192, *Proc. Natl. Acad. Sci. USA* 48:202), and adenine phosphoribosyltransferase (Lowy et al., 1980, *Cell*22:817) genes are employed in tk-, hgprt- or aprt-cells, respectively. Also, antimetabolite resistance are used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (*Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May 1993, *TIB TECH* 11 (5): 155-215) and hygro, which confers resistance to hygromycin (Santerre et al., 1984, *Gene* 30:147). Methods commonly known in the art of recombinant DNA technology which can be used are described in Ausubel et al. (eds., 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J. Mol. Biol.* 150:1).

In some instances, the expression levels of an antibody are increased by vector amplification (for a review, see Bebbington and Hentschel, *The use of vectors based on gene amplification for the expression of cloned genes in mammalian cells in DNA cloning*, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell Biol.* 3:257).

In some instances, any method known in the art for purification or analysis of an antibody or antibody conjugates is used, for example, by chromatography (e.g., ion exchange, affinity, particularly by affinity for the specific antigen after Protein A, and sizing column chromatography), centrifugation, differential solubility, or by any other standard technique for the purification of proteins. Exemplary chromatography methods included, but are not limited to, strong anion exchange chromatography, hydrophobic interaction chromatography, size exclusion chromatography, and fast protein liquid chromatography.

Conjugation Chemistry

In some embodiments, a polynucleic acid molecule B is conjugated to a binding moiety. In some embodiments, a polynucleic acid molecule B is conjugated to a binding moiety in a formula A-X-B (X is a linker conjugating A and B). In some instances, the binding moiety comprises amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of binding moiety also include steroids, such as cholesterol, phospholipids, di-and triacylglycerols, fatty acids, hydrocarbons (e.g., saturated, unsaturated, or contains substitutions), enzyme substrates, biotin, digoxigenin, and polysaccharides. In some instances, the binding moiety is an antibody or antigen binding fragment thereof. In some instances, the polynucleic acid molecule is further conjugated to a polymer, and optionally an endosomolytic moiety.

In some embodiments, the polynucleic acid molecule is conjugated to the binding moiety by a chemical ligation process. In some instances, the polynucleic acid molecule is conjugated to the binding moiety by a native ligation. In some instances, the conjugation is as described in: Dawson, et al. "Synthesis of proteins by native chemical ligation," *Science* 1994, 266, 776-779; Dawson, et al. "Modulation of Reactivity in Native Chemical Ligation through the Use of Thiol Additives," *J. Am. Chem. Soc.* 1997, 119, 4325-4329; Hackeng, et al. "Protein synthesis by native chemical ligation: Expanded scope by using straightforward methodology.," *Proc. Natl. Acad. Sci. USA* 1999, 96, 10068-10073; or Wu, et al. "Building complex glycopeptides: Development of a cysteine-free native chemical ligation protocol," *Angew. Chem. Int. Ed.* 2006, 45, 4116-4125. In some instances, the conjugation is as described in U.S. Pat. No. 8,936,910. In some embodiments, the polynucleic acid molecule is conjugated to the binding moiety either site-specifically or non-specifically via native ligation chemistry.

In some instances, the polynucleic acid molecule is conjugated to the binding moiety by a site-directed method utilizing a "traceless" coupling technology (Philochem). In some instances, the "traceless" coupling technology utilizes an N-terminal 1,2-aminothiol group on the binding moiety which is then conjugate with a polynucleic acid molecule containing an aldehyde group. (see Casi et al., "Site-specific traceless coupling of potent cytotoxic drugs to recombinant antibodies for pharmacodelivery," *JACS* 134 (13): 5887-5892 (2012))

In some instances, the polynucleic acid molecule is conjugated to the binding moiety by a site-directed method utilizing an unnatural amino acid incorporated into the binding moiety. In some instances, the unnatural amino acid comprises p-acetylphenylalanine (pAcPhe). In some instances, the keto group of pAcPhe is selectively coupled to an alkoxy-amine derivatived conjugating moiety to form an oxime bond. (see Axup et al., "Synthesis of site-specific antibody-drug conjugates using unnatural amino acids," *PNAS* 109 (40): 16101-16106 (2012)).

In some instances, the polynucleic acid molecule is conjugated to the binding moiety by a site-directed method utilizing an enzyme-catalyzed process. In some instances, the site-directed method utilizes SMARTag™ technology (Catalent, Inc.). In some instances, the SMARTag™ technology comprises generation of a formylglycine (FGly) residue from cysteine by formylglycine-generating enzyme (FGE) through an oxidation process under the presence of an aldehyde tag and the subsequent conjugation of FGly to an alkylhydraine-functionalized polynucleic acid molecule via hydrazino-Pictet-Spengler (HIPS) ligation. (see Wu et al., "Site-specific chemical modification of recombinant proteins produced in mammalian cells by using the genetically encoded aldehyde tag," PNAS 106 (9): 3000-3005 (2009); Agarwal, et al., "A Pictet-Spengler ligation for protein chemical modification," PNAS 110 (1): 46-51 (2013))

In some instances, the enzyme-catalyzed process comprises microbial transglutaminase (mTG). In some cases, the polynucleic acid molecule is conjugated to the binding moiety utilizing a microbial transglutaminase-catalyzed process. In some instances, mTG catalyzes the formation of a covalent bond between the amide side chain of a glutamine within the recognition sequence and a primary amine of a functionalized polynucleic acid molecule. In some instances, mTG is produced from *Streptomyces mobarensis*. (see Strop et al., "Location matters: site of conjugation modulates stability and pharmacokinetics of antibody drug conjugates," *Chemistry and Biology* 20 (2) 161-167 (2013))

In some instances, the polynucleic acid molecule is conjugated to the binding moiety by a method as described in PCT Publication No. WO2014/140317, which utilizes a sequence-specific transpeptidase.

In some instances, the polynucleic acid molecule is conjugated to the binding moiety by a method as described in U.S. Patent Publication Nos. 2015/0105539 and 2015/0105540.

Polymer Conjugating Moiety

In some embodiments, a polymer moiety C is further conjugated to a polynucleic acid molecule described herein, a binding moiety described herein, or in combinations thereof. In some instances, a polymer moiety C is conjugated a polynucleic acid molecule in a formula A-$X_1$-B-$X_2$-C ($X_1$. $X_2$ as two linkers conjugating A and B, B and C, respectively). In some cases, a polymer moiety C is conjugated to a binding moiety. In other cases, a polymer moiety C is conjugated to a polynucleic acid molecule-binding moiety molecule. In additional cases, a polymer moiety C is conjugated, as illustrated supra.

In some instances, the polymer moiety C is a natural or synthetic polymer, consisting of long chains of branched or unbranched monomers, and/or cross-linked network of monomers in two or three dimensions. In some instances, the polymer moiety C includes a polysaccharide, lignin, rubber, or polyalkylen oxide (e.g., polyethylene glycol). In some instances, the at least one polymer moiety C includes, but is not limited to, alpha-, omega-dihydroxylpolyethyleneglycol, biodegradable lactone-based polymer, e.g. polyacrylic acid, polylactide acid (PLA), poly(glycolic acid) (PGA), polypropylene, polystyrene, polyolefin, polyamide, polycyanoacrylate, polyimide, polyethylene terephthalate (also known as poly (ethylene terephthalate), PET, PETG, or PETE), polytetramethylene glycol (PTG), or polyurethane as well as mixtures thereof. As used herein, a mixture refers to the use of different polymers within the same compound as well as in reference to block copolymers. In some cases, block copolymers are polymers wherein at least one section of a polymer is build up from monomers of another polymer. In some instances, the polymer moiety C comprises polyalkylene oxide. In some instances, the polymer moiety C comprises PEG. In some instances, the polymer moiety C comprises polyethylene imide (PEI) or hydroxy ethyl starch (HES).

In some instances, C is a PEG moiety. In some instances, the PEG moiety is conjugated at the 5' terminus of the polynucleic acid molecule while the binding moiety is conjugated at the 3' terminus of the polynucleic acid molecule. In some instances, the PEG moiety is conjugated at the 3' terminus of the polynucleic acid molecule while the binding moiety is conjugated at the 5' terminus of the polynucleic acid molecule. In some instances, the PEG moiety is conjugated to an internal site of the polynucleic acid molecule. In some instances, the PEG moiety, the binding moiety, or a combination thereof, are conjugated to an internal site of the polynucleic acid molecule. In some instances, the conjugation is a direct conjugation. In some instances, the conjugation is via native ligation.

In some embodiments, the polyalkylene oxide (e.g., PEG) is a polydisperse or monodisperse compound. In some instances, polydisperse material comprises disperse distribution of different molecular weight of the material, characterized by mean weight (weight average) size and dispersity. In some instances, the monodisperse PEG comprises one size of molecules. In some embodiments, C is poly- or monodispersed polyalkylene oxide (e.g., PEG) and the indicated molecular weight represents an average of the molecular weight of the polyalkylene oxide, e.g., PEG, molecules.

In some embodiments, the molecular weight of the polyalkylene oxide (e.g., PEG) is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da.

In some embodiments, C is polyalkylene oxide (e.g., PEG) and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some embodiments, C is PEG and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some instances, the molecular weight of C is about 200 Da. In some instances, the molecular weight of C is about 300 Da. In some instances, the molecular weight of C is about 400 Da. In some instances, the molecular weight of C is about 500 Da. In some instances, the molecular weight of C is about 600 Da. In some instances, the molecular weight of C is about 700 Da. In some instances, the molecular weight of C is about 800 Da. In some instances, the molecular weight of C is about 900 Da. In some instances, the molecular weight of C is about 1000 Da. In some instances, the molecular weight of C is about 1100 Da. In some instances, the molecular weight of C is about 1200 Da. In some instances, the molecular weight of C is about 1300 Da. In some instances, the molecular weight of C is about 1400 Da. In some instances, the molecular weight of C is about 1450 Da. In some instances, the molecular weight of C is about 1500 Da. In some instances, the molecular weight of C is about 1600 Da. In some instances, the molecular weight of C is about 1700 Da. In some instances, the molecular weight of C is about 1800 Da. In some instances, the molecular weight of C is about 1900 Da. In some instances, the molecular weight of C is about 2000 Da. In some instances, the molecular weight of C is about 2100 Da. In some instances, the molecular weight of C is about 2200 Da. In some instances, the molecular weight of C is about 2300 Da. In some instances, the molecular weight of C is about 2400 Da. In some instances, the molecular weight of C is about 2500 Da. In some instances, the molecular weight of C is about 2600 Da. In some instances, the molecular weight of C is about 2700 Da. In some instances, the molecular weight of C is about 2800 Da. In some instances, the molecular weight of C is about 2900 Da. In some instances, the molecular weight of C is about 3000 Da. In some instances, the molecular weight of C is about 3250 Da. In some instances, the molecular weight of C is about 3350 Da. In some instances, the molecular weight of C is about 3500 Da. In some instances, the molecular weight of C is about 3750 Da. In some instances, the molecular weight of C is about 4000 Da. In some instances, the molecular weight of C is about 4250 Da. In some instances, the molecular weight of C is about 4500 Da. In some instances, the molecular weight of C is about 4600 Da. In some instances, the molecular weight of C is about 4750 Da. In some instances, the molecular weight of C is about 5000 Da. In some instances, the molecular weight of C is about 5500 Da. In some instances, the molecular weight of C is about 6000 Da. In some instances, the molecular weight of C is about 6500 Da. In some instances, the molecular weight of C is about 7000 Da. In some instances, the molecular weight of C is about 7500 Da. In some instances, the molecular weight of C is about 8000 Da. In some instances, the molecular weight of C is about 10,000 Da. In some instances, the molecular weight of C is about 12,000 Da. In some instances, the molecular weight of C is about 20,000 Da. In some instances, the molecular weight of C is about 35,000 Da. In some instances, the molecular weight of C is about 40,000 Da. In some instances, the molecular weight of C is about 50,000 Da. In some instances, the molecular weight of C is about 60,000 Da. In some instances, the molecular weight of C is about 100,000 Da.

In some embodiments, the polyalkylene oxide (e.g., PEG) comprises discrete ethylene oxide units (e.g., four to about 48 ethylene oxide units). In some instances, the polyalkylene oxide comprising the discrete ethylene oxide units is a linear chain. In other cases, the polyalkylene oxide comprising the discrete ethylene oxide units is a branched chain.

In some instances, the polymer moiety C is a polyalkylene oxide (e.g., PEG) comprising discrete ethylene oxide units. In some cases, the polymer moiety C comprises between about 4 and about 48 ethylene oxide units. In some cases, the polymer moiety C comprises about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, or about 48 ethylene oxide units.

In some instances, the polymer moiety C is a discrete PEG comprising, e.g., between about 4 and about 48 ethylene oxide units. In some cases, the polymer moiety C is a discrete PEG comprising, e.g., about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, or about 48 ethylene oxide units. In some cases, the polymer moiety C is a discrete PEG comprising, e.g., about 4 ethylene oxide units. In some cases, the polymer moiety C is a discrete PEG comprising, e.g., about 5 ethylene oxide units. In some cases, the polymer moiety C is a discrete PEG comprising, e.g., about 6 ethylene oxide units. In some cases, the polymer moiety C is a discrete PEG comprising, e.g., about 7 ethylene oxide units. In some cases, the polymer moiety C is a discrete PEG comprising, e.g., about 8 ethylene oxide units. In some cases, the polymer moiety C is a discrete PEG comprising, e.g., about 9 ethylene oxide units. In some cases, the polymer moiety C is a discrete PEG comprising, e.g., about 10 ethylene oxide units. In some cases, the polymer moiety C is a discrete PEG comprising, e.g., about 11 ethylene oxide units. In some cases, the polymer moiety C is a discrete PEG comprising, e.g., about 12 ethylene oxide units. In some cases, the polymer moiety C is a discrete PEG comprising, e.g., about 13 ethylene oxide units. In some cases, the polymer moiety C is a discrete PEG comprising, e.g., about 14 ethylene oxide units. In some cases, the polymer moiety C is a discrete PEG comprising, e.g., about 15 ethylene oxide units. In some cases, the polymer moiety C is a discrete PEG comprising, e.g., about 16 ethylene oxide units. In some cases, the polymer moiety C is a discrete PEG comprising, e.g., about 17 ethylene oxide units. In some cases, the polymer moiety C is a discrete PEG comprising, e.g., about 18 ethylene oxide units. In some cases, the polymer moiety C is a discrete PEG comprising, e.g., about 19 ethylene oxide units. In some cases, the polymer moiety C is a discrete PEG comprising, e.g., about 20 ethylene oxide units. In some cases, the polymer moiety C is a discrete PEG comprising, e.g., about 21 ethylene oxide units. In some cases, the polymer moiety C is a discrete PEG comprising, e.g., about 22 ethylene oxide units. In some cases, the polymer moiety C is a discrete PEG comprising, e.g., about 23 ethylene oxide units. In some cases, the polymer moiety C is a discrete PEG comprising, e.g., about 24 ethylene oxide units. In some cases, the polymer moiety C is a discrete PEG comprising, e.g., about 25 ethylene oxide units. In some cases, the polymer moiety C is a discrete PEG comprising, e.g., about 26 ethylene oxide units. In some cases, the polymer moiety C is a discrete PEG comprising, e.g., about 27 ethylene oxide units. In some cases, the polymer moiety C is a discrete PEG comprising, e.g., about 28 ethylene oxide units. In some cases, the polymer moiety C is a discrete PEG comprising, e.g., about 29 ethylene oxide units. In some cases, the polymer moiety C is a discrete PEG comprising, e.g., about 30 ethylene oxide units. In some cases, the polymer moiety C is a discrete PEG comprising, e.g., about 31 ethylene oxide units. In some cases, the polymer moiety C is a discrete PEG comprising, e.g., about 32 ethylene oxide units. In some cases, the polymer moiety C is a discrete PEG comprising, e.g., about 33 ethylene oxide units. In some cases, the polymer moiety C is a discrete PEG comprising, e.g., about 34 ethylene oxide units. In some cases, the polymer moiety C is a discrete PEG comprising, e.g., about 35 ethylene oxide units. In some cases, the polymer moiety C is a discrete PEG comprising, e.g., about 36 ethylene oxide units. In some cases, the polymer moiety C is a discrete PEG comprising, e.g., about 37 ethylene oxide units. In some cases, the polymer moiety C is a discrete PEG comprising, e.g., about 38 ethylene oxide units. In some cases, the polymer moiety C is a discrete PEG comprising, e.g., about 39 ethylene oxide units. In some cases, the polymer moiety C is a discrete PEG comprising, e.g., about 40 ethylene oxide units. In some cases, the polymer moiety C is a discrete PEG comprising, e.g., about 41 ethylene oxide units. In some cases, the polymer moiety C is a discrete PEG comprising, e.g., about 42 ethylene oxide units. In some cases, the polymer moiety C is a discrete PEG comprising, e.g., about 43 ethylene oxide units. In some cases, the polymer moiety C is a discrete PEG comprising, e.g., about 44 ethylene oxide units. In some cases, the polymer moiety C is a discrete PEG comprising, e.g., about 45 ethylene oxide units. In some cases, the polymer moiety C is a discrete PEG comprising, e.g., about 46 ethylene oxide units. In some cases, the polymer moiety C is a discrete PEG comprising, e.g., about 47 ethylene oxide units. In some cases, the polymer moiety C is a discrete PEG comprising, e.g., about 48 ethylene oxide units. In some cases, the polymer moiety C is dPEG® (Quanta Biodesign Ltd).

In some embodiments, the polymer moiety C comprises a cationic mucic acid-based polymer (cMAP). In some instances, cMAP comprises one or more subunit of at least one repeating subunit, and the subunit structure is represented as Formula (V):

Formula V

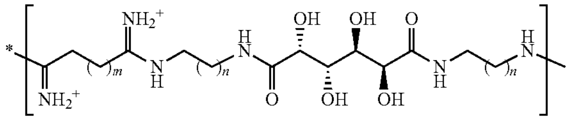

wherein m is independently at each occurrence 1, 2, 3, 4, 5, 6, 7, 8, 9, or 10, preferably 4-6 or 5; and n is independently at each occurrence 1, 2, 3, 4, or 5. In some embodiments, m and n are, for example, about 10.

In some instances, cMAP is further conjugated to a PEG moiety, generating a cMAP-PEG copolymer, an mPEG-cMAP-PEGm triblock polymer, or a cMAP-PEG-cMAP triblock polymer. In some instances, the PEG moiety is in a range of from about 500 Da to about 50,000 Da. In some instances, the PEG moiety is in a range of from about 500 Da to about 1000 Da, greater than 1000 Da to about 5000 Da, greater than 5000 Da to about 10,000 Da, greater than 10,000 to about 25,000 Da, greater than 25,000 Da to about 50,000 Da, or any combination of two or more of these ranges.

In some instances, the polymer moiety C is cMAP-PEG copolymer, an mPEG-cMAP-PEGm triblock polymer, or a cMAP-PEG-cMAP triblock polymer. In some cases, the polymer moiety Cis cMAP-PEG copolymer. In other cases, the polymer moiety C is an mPEG-cMAP-PEGm triblock polymer. In additional cases, the polymer moiety C is a cMAP-PEG-cMAP triblock polymer.

In some embodiments, the polymer moiety C is conjugated to the polynucleic acid molecule, the binding moiety, and optionally to the endosomolytic moiety as illustrated supra.

Endosomolytic or Cell Membrane Penetration Moiety

In some embodiments, a molecule of Formula (I): A-$X_1$-B-$X_2$-C, further comprises an additional conjugating moiety. In some instances, the additional conjugating moiety is an endosomolytic moiety and/or a cell membrane penetration moiety. In some cases, the endosomolytic moiety is a cellular compartmental release component, such as a compound capable of releasing from any of the cellular compartments known in the art, such as the endosome, lysosome, endoplasmic reticulum (ER), Golgi apparatus, microtubule, peroxisome, or other vesicular bodies with the cell. In some cases, the endosomolytic moiety comprises an endosomolytic polypeptide, an endosomolytic polymer, an endosomolytic lipid, or an endosomolytic small molecule. In some cases, the endosomolytic moiety comprises an endosomolytic polypeptide. In other cases, the endosomolytic moiety comprises an endosomolytic polymer. In some cases, the cell membrane penetration moiety comprises a cell penetrating peptide (CPP). In other cases, the cell membrane penetration moiety comprises a cell penetrating lipid. In other cases, the cell membrane penetration moiety comprises a cell penetrating small molecule.

Endosomolytic and Cell Membrane Penetration Polypeptides

In some embodiments, a molecule of Formula (I): A-$X_1$-B-$X_2$-C, is further conjugated with an endosomolytic polypeptide. In some cases, the endosomolytic polypeptide is a pH-dependent membrane active peptide. In some cases, the endosomolytic polypeptide is an amphipathic polypeptide. In additional cases, the endosomolytic polypeptide is a peptidomimetic. In some instances, the endosomolytic polypeptide comprises INF, melittin, meucin, or their respective derivatives thereof. In some instances, the endosomolytic polypeptide comprises INF or its derivatives thereof. In other cases, the endosomolytic polypeptide comprises melittin or its derivatives thereof. In additional cases, the endosomolytic polypeptide comprises meucin or its derivatives thereof.

In some instances, INF7 is a 24 residue polypeptide those sequence comprises CGIFGEIEELIEEGLENLIDWGNA (SEQ ID NO: 67), or GLFEAIEGFIENGWEGMIDGWYGC (SEQ ID NO: 68). In some instances, INF7 or its derivatives comprise a sequence of:

```
                                    (SEQ ID NO: 69)
GLFEAIEGFIENGWEGMIWDYGSGSCG,

WYG-(PEG)6-NH2
                                    (SEQ ID NO: 70)
GLFEAIEGFIENGWEGMIDG,
or
                                    (SEQ ID NO: 71)
GLFEAIEGFIENGWEGMIWDYG-SGSC-K(GalNAc)2.
```

In some cases, melittin is a 26 residue polypeptide those sequence comprises CLIGAILKVLATGLPTLISWIKNKRKQ (SEQ ID NO: 72), or GIGAVLKVLTTGLPALISWIKRKRQQ (SEQ ID NO: 73). In some instances, melittin comprises a polypeptide sequence as described in U.S. Pat. No. 8,501,930.

In some instances, meucin is an antimicrobial peptide (AMP) derived from the venom gland of the scorpion *Mesobuthus eupeus*. In some instances, meucin comprises of meucin-13 those sequence comprises IFGAIAGLLKNIF-$NH_2$ (SEQ ID NO: 74) and meucin-18 those sequence comprises FFGHLFKLATKIIPSLFQ (SEQ ID NO: 75).

In some instances, the endosomolytic polypeptide comprises a polypeptide in which its sequence is at least 50%, 60%, 70%, 80%, 90%, 95%, or 99% sequence identity to INF7 or its derivatives thereof, melittin or its derivatives thereof, or meucin or its derivatives thereof. In some instances, the endosomolytic moiety comprises INF7 or its derivatives thereof, melittin or its derivatives thereof, or meucin or its derivatives thereof.

In some instances, the endosomolytic moiety is INF7 or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 67-71. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 67. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 68-71. In some cases, the endosomolytic moiety comprises SEQ ID NO: 67. In some cases, the endosomolytic moiety comprises SEQ ID NO: 68-71. In some cases, the endosomolytic moiety consists of SEQ ID NO: 67. In some cases, the endosomolytic moiety consists of SEQ ID NO: 68-71.

In some instances, the endosomolytic moiety is melittin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 72 or 73. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 72. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 73. In some cases, the endosomolytic moiety comprises SEQ ID NO: 72. In some cases, the endosomolytic moiety comprises SEQ ID NO: 73. In some cases, the endosomolytic moiety consists of SEQ ID NO: 72. In some cases, the endosomolytic moiety consists of SEQ ID NO: 73.

In some instances, the endosomolytic moiety is meucin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 74 or 75. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 74. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 75. In some cases, the endosomolytic moiety comprises SEQ ID NO: 74. In some cases, the endosomolytic moiety comprises SEQ ID NO: 75. In some cases, the endosomolytic moiety consists of SEQ ID NO: 74. In some cases, the endosomolytic moiety consists of SEQ ID NO: 75.

In some instances, the endosomolytic moiety comprises a sequence as illustrated in Table 9.

TABLE 9

| NAME | ORIGIN | AMINO ACID SEQUENCE | SEQ ID NO: | TYPE |
|---|---|---|---|---|
| Pep-1 | NLS from Simian Virus 40 large antigen and Reverse transcriptase of HIV | KETWWETWWTEWSQPKKKRKV | 76 | Primary amphipathic |
| pVEC | VE-cadherin | LLIILRRRRIRKQAHAHSK | 77 | Primary amphipathic |
| VT5 | Synthetic peptide | DPKGDPKGVTVTVTVTVTGKGDP KPD | 78 | β-sheet amphipathic |
| C105Y | 1-antitrypsin | CSIPPEVKFNKPFVYLI | 116 | - |
| Transportan | Galanin and mastoparan | GWTLNSAGYLLGKINLKALAALA KKIL | 79 | Primary amphipathic |
| TP10 | Galanin and mastoparan | AGYLLGKINLKALAALAKKIL | 80 | Primary amphipathic |
| MPG | A hydrofobic domain from the fusion sequence of HIV gp41 and NLS of SV40 T antigen | GALFLGFLGAAGSTMGA | 81 | β-sheet amphipathic |
| gH625 | Glycoprotein gH of HSV type I | HGLASTLTRWAHYNALIRAF | 82 | Secondary amphipathic α-helical |
| CADY | PPTG1 peptide | GLWRALWRLLRSLWRLLWRA | 83 | Secondary amphipathic α-helical |
| GALA | Synthetic peptide | WEAALAEALAEALAEHLAEALAE ALEALAA | 84 | Secondary amphipathic α-helical |
| INF | Influenza HA2 fusion peptide | GLFEAIEGFIENGWEGMIDGWYGC | 85 | Secondary amphipathic α-helical/ pH-dependent membrane active peptide |
| HA2E5-TAT | Influenza HA2 subunit of influenza virus X31 strain fusion peptide | GLFGAIAGFIENGWEGMIDGWYG | 86 | Secondary amphipathic α-helical/ pH-dependent membrane active peptide |

TABLE 9-continued

| NAME | ORIGIN | AMINO ACID SEQUENCE | SEQ ID NO: | TYPE |
|---|---|---|---|---|
| HA2-penetratin | Influenza HA2 subunit of influenza virus X31 strain fusion peptide | GLFGAIAGFIENGWEGMIDGRQIKI WFQNRRMKW KK-amide | 87 | pH-dependent membrane active peptide |
| HA-K4 | Influenza HA2 subunit of influenza virus X31 strain fusion peptide | GLFGAIAGFIENGWEGMIDG-SSKKKK | 88 | pH-dependent membrane active peptide |
| HA2E4 | Influenza HA2 subunit of influenza virus X31 strain fusion peptide | GLFEAIAGFIENGWEGMIDGGGYC | 89 | pH-dependent membrane active peptide |
| H5WYG | HA2 analogue | GLFHAIAHFIHGGWH GLIHGWYG | 90 | pH-dependent membrane active peptide |
| GALA-INF3-(PEG)6-NH | INF3 fusion peptide | GLFEAIEGFIENGWEGLAEALAEAL EALAA-(PEG)6-NH2 | 91 | pH-dependent membrane active peptide |
| CM18-TAT11 | Cecropin-A-Melittin$_{2-12}$ ($CM_{18}$) fusion peptide | KWKLFKKIGAVLKVLTTG-YGRKKRRQRRR | 92 | pH-dependent membrane active peptide |

In some cases, the endosomolytic moiety comprises a Bak BH3 polypeptide which induces apoptosis through antagonization of suppressor targets such as Bcl-2 and/or Bcl-XL. In some instances, the endosomolytic moiety comprises a Bak BH3 polypeptide described in Albarran, et al., "Efficient intracellular delivery of a pro-apoptotic peptide with a pH-responsive carrier," *Reactive & Functional Polymers* 71:261-265 (2011).

In some instances, the endosomolytic moiety comprises a polypeptide (e.g., a cell-penetrating polypeptide) as described in PCT Publication Nos. WO2013/166155 or WO2015/069587.

Endosomolytic Lipids

In some embodiments, the endosomolytic moiety is a lipid (e.g., a fusogenic lipid). In some embodiments, a molecule of Formula (I): $A-X_1-B-X_2-C$, is further conjugated with an endosomolytic lipid (e.g., fusogenic lipid). Exemplary fusogenic lipids include 1,2-dileoyl-sn-3-phosphoethanolamine (DOPE), phosphatidylethanolamine (POPE), palmitoyloleoylphosphatidylcholine (POPC), (6Z,9Z,28Z,31Z)-heptatriaconta-6,9,28,31-tetraen-19-ol (Di-Lin), N-methyl (2,2-di((9Z,12Z)-octadeca-9,12-dienyl)-1,3-dioxolan-4-yl)methanamine (DLin-k-DMA) and N-methyl-2-(2,2-di((9Z, 12Z)-octadeca-9,12-dienyl)-1,3-dioxolan-4-yl)ethanamine (XTC).

In some instances, an endosomolytic moiety is a lipid (e.g., a fusogenic lipid) described in PCT Publication No. WO09/126,933.

Endosomolytic Small Molecules

In some embodiments, the endosomolytic moiety is a small molecule. In some embodiments, a molecule of Formula (I): $A-X_1-B-X_2-C$, is further conjugated with an endosomolytic small molecule. Exemplary small molecules suitable as endosomolytic moieties include, but are not limited to, quinine, chloroquine, hydroxychloroquines, amodiaquins (carnoquines), amopyroquines, primaquines, mefloquines, nivaquines, halofantrines, quinone imines, or a combination thereof. In some instances, quinoline endosomolytic moieties include, but are not limited to, 7-chloro-4-(4-diethylamino-1-methylbutyl-amino) quinoline (chloroquine); 7-chloro-4-(4-ethyl-(2-hydroxyethyl)-amino-1-methylbutyl-amino) quinoline (hydroxychloroquine); 7-fluoro-4-(4-diethylamino-1-methylbutyl-amino) quinoline; 4-(4-diethylamino-1-methylbutylamino) quinoline; 7-hydroxy-4-(4-diethyl-amino-1-methylbutylamino) quinoline; 7-chloro-4-(4-diethylamino-1-butylamino) quinoline (desmethylchloroquine); 7-fluoro-4-(4-diethylamino-1-butylamino) quinoline); 4-(4-diethyl-amino-1-butylamino) quinoline; 7-hydroxy-4-(4-diethylamino-1-butylamino) quinoline; 7-chloro-4-(1-carboxy-4-diethylamino-1-butylamino) quinoline; 7-fluoro-4-(1-carboxy-4-diethyl-amino-1-butylamino) quinoline; 4-(1-carboxy-4-diethylamino-1-butylamino) quinoline; 7-hydroxy-4-(1-carboxy-4-diethylamino-1-butylamino) quinoline; 7-chloro-4-(1-carboxy-4-diethylamino-1-methylbutylamino) quinoline; 7-fluoro-4-(1-carboxy-4-diethyl-amino-1-methylbutylamino) quinoline; 4-(1-carboxy-4-diethylamino-1-methylbutylamino) quinoline; 7-hydroxy-4-(1-carboxy-4-diethylamino-1-methylbutylamino) quinoline; 7-fluoro-4-(4-ethyl-(2-hydroxyethyl)-amino-1-methylbutylamino) quinoline; 4-(4-ethyl-(2-hydroxy-ethyl)-amino-1-methylbutylamino-) quinoline; 7-hydroxy-4-(4-ethyl-(2-hydroxyethyl)-amino-1- methylbutylamino) quinoline; hydroxychloroquine phosphate; 7-chloro-4-(4-ethyl-(2-hydroxyethyl-1)-amino-1-butylamino) quinoline (desmethylhydroxychloroquine); 7-fluoro-4-(4-ethyl-(2-hydroxyethyl)-amino-1-butylamino) quinoline; 4-(4-ethyl-(2-hydroxyethyl)-amino-1-butylamino) quinoline; 7-hydroxy-4-(4-ethyl-(2-hydroxyethyl)-amino-1-butylamino) quinoline; 7-chloro-4-(1-carboxy-4-ethyl-(2-hydroxyethyl)-amino-1-butylamino) quinoline; 7-fluoro-4-(1-carboxy-4-ethyl-(2-hydroxyethyl)-amino-1-butylamino) quinoline; 4-(1-carboxy-4-ethyl-(2-hydroxyethyl)-amino-1-butylamino) quinoline; 7-hydroxy-4-(1-carboxy-4-ethyl-(2-hydroxyethyl)-amino-1-butylamino) quinoline; 7-chloro-4-(1-carboxy-4-ethyl-(2-hydroxyethyl)-amino-1-methylbutylamino) quinoline; 7-fluoro-4-(1-carboxy-4-ethyl-(2-hydroxyethyl)-amino-1-methylbutylamino) quinoline; 4-(1-carboxy-4-ethyl-(2-hydroxyethyl)-amino-1-methylbutylamino) quinoline; 7-hydroxy-4-(1-carboxy-4-ethyl-(2-hydroxyethyl)-amino-1-methylbutylamino) quinoline; 8-[(4-aminopentyl)amino-6-methoxydihydrochloride quinoline; 1-acetyl-1,2,3,4-tetrahydroquinoline; 8-[(4-aminopentyl)amino]-6-methoxyquinoline dihydrochloride; 1-butyryl-1,2,3,4-tetrahydroquinoline; 3-chloro-4-(4-hydroxy-alpha, alpha'-bis(2-methyl-1-pyrrolidinyl)-2,5-xylidinoquinoline, 4-[(4-diethyl-amino)-1-methylbutyl-amino]-6-methoxyquinoline; 3-fluoro-4-(4-hydroxy-alpha,alpha'-bis (2-methyl-1-pyrrolidinyl)-2,5-xylidinoquinoline, 4-[(4-diethylamino)-1-methylbutyl-amino]-6-methoxyquinoline; 4-(4-hydroxy-alpha, alpha'-bis(2-methyl-1-pyrrolidinyl)-2, 5-xylidinoquinoline; 4-[(4-diethylamino)-1-methylbutyl-amino]-6-methoxyquinoline; 3,4-dihydro-1-(2H)-quinolinecarboxyaldehyde; 1,1'-pentamethylene diquinoleinium diiodide; 8-quinolinol sulfate and amino, aldehyde, carboxylic, hydroxyl, halogen, keto, sulfhydryl and vinyl derivatives or analogs thereof. In some instances, an endosomolytic moiety is a small molecule described in Naisbitt et al (1997, J Pharmacol Exp Therapy 280:884-893) and in U.S. Pat. No. 5,736,557.

Cell Penetrating Polypeptide (CPP)

In some embodiments, cell penetrating polypeptide comprises positively charged short peptides with 5-30 amino acids. In some embodiments, cell penetrating polypeptide comprises arginine or lysine rich amino acid sequences. In some embodiments, cell penetrating polypeptide includes any polypeptide or combination thereof listed in Table 10.

TABLE 10

| Peptide | Sequence | SEQ ID NO |
|---|---|---|
| Antennapedia Penetratin (43-58) | RQIKIWFQNRRMKWKK | 93 |
| HIV-1 TAT protein (48-60) | GRKKRRQRRRPPQ | 94 |
| pVEC Cadherin (615-632) | LLIILRRRIRKQAHAHSK | 95 |
| Transportan Galanine/Mastoparan | GWTLNSAGYLLGKINLKALAALAKKIL | 96 |
| MPG HIV-gp41/SV40 T-antigen | GALFLGFLGAAGSTMGAWSQPKKKRKV | 97 |
| Pep-1 HIV-reverse transcriptase/SV40 T-antigen | KETWWETWWTEWSQPKKKRKV | 98 |
| Polyarginines | R(n); 6 < n < 12 | 99 |
| MAP | KLALKLALKALKAALKLA | 100 |
| R6W3 | RRWWRRWRR | 101 |
| NLS | CGYGPKKKRKVGG | 102 |
| 8-lysines | KKKKKKKK | 103 |
| ARF(1-22) | MVRRFLVTLRIRRACGPPRVRV | 104 |
| Azurin-p28 | LSTAADMQGVVTDGMASGLDKDYLKPDD | 105 |

Linkers

In some embodiments, a linker described herein is a cleavable linker or a non-cleavable linker. In some instances, the linker is a cleavable linker. In other instances, the linker is a non-cleavable linker.

In some cases, the linker is a non-polymeric linker. A non-polymeric linker refers to a linker that does not contain a repeating unit of monomers generated by a polymerization process. Exemplary non-polymeric linkers include, but are not limited to, $C_1$-$C_6$ alkyl group (e.g., a $C_5$, $C_4$, $C_3$, $C_2$, or $C_1$ alkyl group), homobifunctional cross linkers, heterobifunctional cross linkers, peptide linkers, traceless linkers, self-immolative linkers, maleimide-based linkers, or combinations thereof. In some cases, the non-polymeric linker comprises a $C_1$-$C_6$ alkyl group (e.g., a $C_5$, $C_4$, $C_3$, $C_2$, or $C_1$ alkyl group), a homobifunctional cross linker, a heterobifunctional cross linker, a peptide linker, a traceless linker, a self-immolative linker, a maleimide-based linker, or a combination thereof. In additional cases, the non-polymeric linker does not comprise more than two of the same type of linkers, e.g., more than two homobifunctional cross linkers, or more than two peptide linkers. In further cases, the non-polymeric linker optionally comprises one or more reactive functional groups.

In some instances, the non-polymeric linker does not encompass a polymer that is described above. In some instances, the non-polymeric linker does not encompass a polymer encompassed by the polymer moiety C. In some cases, the non-polymeric linker does not encompass a polyalkylene oxide (e.g., PEG). In some cases, the non-polymeric linker does not encompass a PEG.

In some instances, the linker comprises a homobifunctional linker. Exemplary homobifunctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis (sulfosuccinimidyl) suberate (BS), disuccinimidyl tartrate (DST), disulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio) propionamido) butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis (iodoacetamide), or N,N'-hexamethylene-bis (iodoacetamide).

In some embodiments, the linker comprises a heterobifunctional linker. Exemplary heterobifunctional linker include, but are not limited to, amine-reactive and sulfhydryl cross-linkers such as N-succinimidyl 3-(2-pyridyldithio) propionate (sPDP), long-chain N-succinimidyl 3-(2-pyridyldithio) propionate (LC-sPDP), water-soluble-long-chain N-succinimidyl 3-(2-pyridyldithio) propionate (sulfo-LC-sPDP), succinimidyloxycarbonyl-a-methyl-α-(2-pyridyldithio) toluene (sMPT), sulfosuccinimidyl-6-[a-methyl-α-(2-pyridyldithio) toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl (4-iodoacteyl)aminobenzoate (sIAB), sulfosuccinimidyl (4-iodoacteyl)aminobenzoate (sulfo-sIAB), succinimidyl-4-(p-maleimidophenyl) butyrate (sMPB), sulfosuccinimidyl-4-(p-maleimidophenyl) butyrate (sulfo-sMPB), N-(Y-maleimidobutyryloxy) succinimide ester (GMBs), N-(y-maleimidobutyryloxy) sulfosuccinimide ester (sulfo-GMBs), succinimidyl 6-((iodoacetyl)amino) hexanoate (sIAX), succinimidyl 6-[6-(((iodoacetyl)amino) hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 ($M2C_2H$), 3-(2-pyridyldithio) propionyl hydrazide (PDPH), amine-reactive and photoreactive cross-linkers such as N-hydroxysuccinimidyl-4-azidosalicylic acid (NHS-AsA), N-hydroxysulfosuccinimidyl-4-azidosalicylic acid (sulfo-NHs-AsA), sulfosuccinimidyl-(4-azidosalicylamido) hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino) hexanoate (sANPAH), sulfosuccinimidyl-6-(4'-azido-2'-nitrophenylamino) hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4 (4-azidophenyl) 1,3'-dithiopropionate (sADP), N-sulfosuccinimidyl (4-azidophenyl)-1,3'-dithiopropionate (sulfo-sADP), sulfosuccinimidyl 4-(p-azidophenyl) butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), p-nitrophenyl diazopyruvate (pNPDP), p-nitrophenyl-2-diazo-3,3,3-trifluoropropionate (PNP-DTP), sulfhydryl-reactive and photoreactive cross-linkers such as1-(p-Azidosalicylamido)-4-(iodoacetamido) butane (AsIB), N-[4-(p-azidosalicylamido)butyl]-3'-(2'-pyridyldithio) propionamide (APDP), benzophenone-4-iodoacetamide, benzophenone-4-maleimide carbonyl-reactive and photoreactive cross-linkers such as p-azidobenzoyl hydrazide (ABH), carboxylate-reactive and photoreactive cross-linkers such as 4-(p-azidosalicylamido)butylamine (AsBA), and arginine-reactive and photoreactive cross-linkers such as p-azidophenyl glyoxal (APG).

In some instances, the linker comprises a reactive functional group. In some cases, the reactive functional group comprises a nucleophilic group that is reactive to an electrophilic group present on a binding moiety. Exemplary electrophilic groups include carbonyl groups-such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide.

In some embodiments, the linker comprises a maleimide group. In some instances, the maleimide group is also referred to as a maleimide spacer. In some instances, the maleimide group further encompasses a caproic acid, forming maleimidocaproyl (mc). In some cases, the linker comprises maleimidocaproyl (mc). In some cases, the linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon, et al., “Self-hydrolyzing maleimides improve the stability and pharmacological properties of antibody-drug conjugates,” Nat. Biotechnol. 32 (10): 1059-1062 (2014). In some instances, the linker comprises a self-stabilizing maleimide. In some instances, the linker is a self-stabilizing maleimide.

In some embodiments, the linker comprises a peptide moiety. In some instances, the peptide moiety comprises at least 2, 3, 4, 5, or 6 more amino acid residues. In some instances, the peptide moiety comprises at most 2, 3, 4, 5, 6, 7, or 8 amino acid residues. In some instances, the peptide moiety comprises about 2, about 3, about 4, about 5, or about 6 amino acid residues. In some instances, the peptide moiety is a cleavable peptide moiety (e.g., either enzymatically or chemically). In some instances, the peptide moiety is a non-cleavable peptide moiety. In some instances, the peptide moiety comprises Val-Cit (valine-citrulline), Gly-Gly-Phe-Gly (SEQ ID NO: 106), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 107), or Gly-Phe-Leu-Gly (SEQ ID NO: 108). In some instances, the linker comprises a peptide moiety such as: Val-Cit (valine-citrulline), Gly-Gly-Phe-Gly (SEQ ID NO: 106), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 107), or Gly-Phe-Leu-Gly (SEQ ID NO: 108). In some cases, the linker comprises Val-Cit. In some cases, the linker is Val-Cit.

In some embodiments, the linker comprises a benzoic acid group, or its derivatives thereof. In some instances, the benzoic acid group or its derivatives thereof comprise paraaminobenzoic acid (PABA). In some instances, the benzoic acid group or its derivatives thereof comprise gamma-aminobutyric acid (GABA).

In some embodiments, the linker comprises one or more of a maleimide group, a peptide moiety, and/or a benzoic acid group, in any combination. In some embodiments, the linker comprises a combination of a maleimide group, a peptide moiety, and/or a benzoic acid group. In some instances, the maleimide group is maleimidocaproyl (mc). In some instances, the peptide group is val-cit. In some instances, the benzoic acid group is PABA. In some instances, the linker comprises a mc-val-cit group. In some cases, the linker comprises a val-cit-PABA group. In additional cases, the linker comprises a mc-val-cit-PABA group.

In some embodiments, the linker is a self-immolative linker or a self-elimination linker. In some cases, the linker is a self-immolative linker. In other cases, the linker is a self-elimination linker (e.g., a cyclization self-elimination linker). In some instances, the linker comprises a linker described in U.S. Pat. No. 9,089,614 or PCT Publication No. WO2015038426.

In some embodiments, the linker is a dendritic type linker. In some instances, the dendritic type linker comprises a branching, multifunctional linker moiety. In some instances, the dendritic type linker is used to increase the molar ratio of polynucleotide B to the binding moiety A. In some instances, the dendritic type linker comprises PAMAM dendrimers.

In some embodiments, the linker is a traceless linker or a linker in which after cleavage does not leave behind a linker moiety (e.g., an atom or a linker group) to a binding moiety A, a polynucleotide B, a polymer C, or an endosomolytic moiety D. Exemplary traceless linkers include, but are not limited to, germanium linkers, silicium linkers, sulfur linkers, selenium linkers, nitrogen linkers, phosphorus linkers, boron linkers, chromium linkers, or phenylhydrazide linker. In some cases, the linker is a traceless aryl-triazene linker as described in Hejesen, et al., “A traceless aryl-triazene linker for DNA-directed chemistry,” *Org Biomol Chem* 11 (15): 2493-2497 (2013). In some instances, the linker is a traceless linker described in Blaney, et al., “Traceless solid-phase organic synthesis,” *Chem. Rev.* 102:2607-2024 (2002). In some instances, a linker is a traceless linker as described in U.S. Pat. No. 6,821,783.

In some instances, the linker is a linker described in U.S. Pat. Nos. 6,884,869; 7,498,298; 8,288,352; 8,609,105; or 8,697,688; U.S. Patent Publication Nos. 2014/0127239; 2013/028919; 2014/286970; 2013/0309256; 2015/037360; or 2014/0294851; or PCT Publication Nos. WO2015057699; WO2014080251; WO2014197854; WO2014145090; or WO2014177042.

In some embodiments, $X_1$ and $X_2$ are each independently a bond or a non-polymeric linker. In some instances, $X_1$ and $X_2$ are each independently a bond. In some cases, $X_1$ and $X_2$ are each independently a non-polymeric linker.

In some instances, $X_1$ is a bond or a non-polymeric linker. In some instances, $X_1$ is a bond. In some instances, $X_1$ is a non-polymeric linker. In some instances, the linker is a $C_1$-$C_6$ alkyl group. In some cases, $X_1$ is a $C_1$-$C_6$ alkyl group, such as for example, a $C_5$, $C_4$, $C_3$, $C_2$, or $C_1$ alkyl group. In some cases, the $C_1$-$C_6$ alkyl group is an unsubstituted $C_1$-$C_6$ alkyl group. As used in the context of a linker, and in particular in the context of $X_1$, alkyl means a saturated straight or branched hydrocarbon radical containing up to six carbon atoms. In some instances, $X_1$ includes a homobifunctional linker or a heterobifunctional linker described supra. In some cases, $X_1$ includes a heterobifunctional linker. In some cases, $X_1$ includes sMCC. In other instances, $X_1$ includes a heterobifunctional linker optionally conjugated to a $C_1$-$C_6$ alkyl group. In other instances, $X_1$ includes sMCC optionally conjugated to a $C_1$-$C_6$ alkyl group. In additional instances, $X_1$ does not include a homobifunctional linker or a heterobifunctional linker described supra.

In some instances, $X_2$ is a bond or a linker. In some instances, $X_2$ is a bond. In other cases, $X_2$ is a linker. In additional cases, $X_2$ is a non-polymeric linker. In some embodiments, $X_2$ is a $C_1$-$C_6$ alkyl group. In some instances, $X_2$ is a homobifunctional linker or a heterobifunctional linker described supra. In some instances, $X_2$ is a homobifunctional linker described supra. In some instances, $X_2$ is a heterobifunctional linker described supra. In some instances, $X_2$ comprises a maleimide group, such as maleimidocaproyl (mc) or a self-stabilizing maleimide group described above. In some instances, $X_2$ comprises a peptide moiety, such as Val-Cit. In some instances, $X_2$ comprises a benzoic acid group, such as PABA. In additional instances, $X_2$ comprises a combination of a maleimide group, a peptide moiety, and/or a benzoic acid group. In additional instances, $X_2$ comprises a mc group. In additional instances, $X_2$ comprises a mc-val-cit group. In additional instances, $X_2$ comprises a val-cit-PABA group. In additional instances, $X_2$ comprises a mc-val-cit-PABA group.

Methods of Use

Muscle dystrophy refers to a loss of muscle mass and/or to a progressive weakening and degeneration of muscles. In some cases, the loss of muscle mass and/or the progressive weakening and degeneration of muscles occurs due to a high rate of protein degradation, a low rate of protein synthesis, or a combination of both. In some cases, a high rate of muscle protein degradation is due to muscle protein catabolism (i.e., the breakdown of muscle protein in order to use amino acids as substrates for gluconeogenesis).

In one embodiment, muscle dystrophy refers to a significant loss in muscle strength. By significant loss in muscle strength is meant a reduction of strength in diseased, injured, or unused muscle tissue in a subject relative to the same muscle tissue in a control subject. In an embodiment, a significant loss in muscle strength is a reduction in strength of at least 10%, at least 15%, at least 20%, at least 25%, at least 30%, at least 35%, at least 40%, at least 45%, at least 50%, or more relative to the same muscle tissue in a control subject. In another embodiment, by significant loss in muscle strength is meant a reduction of strength in unused muscle tissue relative to the muscle strength of the same muscle tissue in the same subject prior to a period of nonuse. In an embodiment, a significant loss in muscle strength is a reduction of at least 10%, at least 15%, at least 20%, at least 25%, at least 30%, at least 35%, at least 40%, at least 45%, at least 50%, or more relative to the muscle strength of the same muscle tissue in the same subject prior to a period of nonuse.

In another embodiment, muscle dystrophy refers to a significant loss in muscle mass. By significant loss in muscle mass is meant a reduction of muscle volume in diseased, injured, or unused muscle tissue in a subject relative to the same muscle tissue in a control subject. In an embodiment, a significant loss of muscle volume is at least 10%, at least 15%, at least 20%, at least 25%, at least 30%, at least 35%, at least 40%, at least 45%, at least 50%, or more relative to the same muscle tissue in a control subject. In another embodiment, by significant loss in muscle mass is meant a reduction of muscle volume in unused muscle tissue relative to the muscle volume of the same muscle tissue in the same subject prior to a period of nonuse. In an embodiment, a significant loss in muscle tissue is at least 10%, at least 15%, at least 20%, at least 25%, at least 30%, at least 35%, at least 40%, at least 45%, at least 50%, or more relative to the muscle volume of the same muscle tissue in the same subject prior to a period of nonuse. Muscle volume is optionally measured by evaluating the cross-section area of a muscle such as by Magnetic Resonance Imaging (e.g., by a muscle volume/cross-section area (CSA) MRI method).

Myotonic dystrophy is a multisystemic neuromuscular disease comprising two main types: myotonic dystrophy type 1 (DM1) and myotonic dystrophy type 2 (DM2). DM1 is caused by a dominantly inherited "CTG" repeat expansion in the gene DM protein kinase (DMPK), which when transcribed into mRNA, forms hairpins that bind with high affinity to the Muscleblind-like (MBNL) family of proteins. MBNL proteins are involved in post-transcriptional splicing and polyadenylatin site regulation and loss of the MBNL protein functions lead to downstream accumulation of nuclear foci and increase in mis-splicing events and subsequently to myotonia and other clinical symptoms.

In some embodiments, described herein is a method of treating muscle dystrophy (e.g., DM1) in a subject, the method comprises providing a polynucleic acid molecule described herein or a polynucleic acid molecule conjugate described herein and administering to the subject a therapeutically effective amount of the polynucleic acid molecule or polynucleic acid molecule conjugate to the subject in need thereof to treat the muscular dystrophy, wherein the polynucleic acid conjugate reduces a quantity of the mRNA transcript of human DMPK. In some embodiments, administering the polynucleic acid molecule conjugate to the subject reduces the quantity of the mRNA transcript of human DMPK at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80% of DMPK mRNA expression level of a patient without the treatment with the polynucleic acid molecule conjugate.

Pharmaceutical Formulation

In some embodiments, the pharmaceutical formulations described herein are administered to a subject by multiple administration routes, including but not limited to, parenteral (e.g., intravenous, subcutaneous, intramuscular), oral, intranasal, buccal, rectal, or transdermal administration routes. In some instances, the pharmaceutical composition describe herein is formulated for parenteral (e.g., intravenous, subcutaneous, intramuscular, intra-arterial, intraperitoneal, intrathecal, intracerebral, intracerebroventricular, or intracranial) administration. In other instances, the pharmaceutical composition describe herein is formulated for oral administration. In still other instances, the pharmaceutical composition describe herein is formulated for intranasal administration.

In some embodiments, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some instances, the pharmaceutical formulation includes multiparticulate formulations. In some instances, the pharmaceutical formulation includes nanoparticle formulations. In some instances, nanoparticles comprise cMAP, cyclodextrin, or lipids. In some cases, nanoparticles comprise solid lipid nanoparticles, polymeric nanoparticles, self-emulsifying nanoparticles, liposomes, microemulsions, or micellar solutions. Additional exemplary nanoparticles include, but are not limited to, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. In some instances, a nanoparticle is a metal nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof.

In some instances, a nanoparticle includes a core or a core and a shell, as in a core-shell nanoparticle.

In some instances, a nanoparticle is further coated with molecules for attachment of functional elements (e.g., with one or more of a polynucleic acid molecule or binding moiety described herein). In some instances, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, a-chymotrypsin, polylysine, polyarginine, histone, protamine, ovalbumin or dextrin or cyclodextrin. In some instances, a nanoparticle comprises a graphene-coated nanoparticle.

In some cases, a nanoparticle has at least one dimension of less than about 500 nm, 400 nm, 300 nm, 200 nm, or 100 nm.

In some instances, the nanoparticle formulation comprises paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes or quantum dots. In some instances, a polynucleic acid molecule or a binding moiety described herein is conjugated either directly or indirectly to the nanoparticle. In some instances, at least 1, 5, 10, 15, 20, 30, 40, 50, 60, 70, 80, 90, 100 or more polynucleic acid molecules or binding moieties described herein are conjugated either directly or indirectly to a nanoparticle.

In some embodiments, the pharmaceutical formulation comprises a delivery vector, e.g., a recombinant vector, the delivery of the polynucleic acid molecule into cells. In some instances, the recombinant vector is DNA plasmid. In other instances, the recombinant vector is a viral vector. Exemplary viral vectors include vectors derived from adeno-associated virus, retrovirus, adenovirus, or alphavirus. In some instances, the recombinant vectors capable of expressing the polynucleic acid molecules provide stable expression in target cells. In additional instances, viral vectors are used that provide for transient expression of polynucleic acid molecules.

In some embodiments, the pharmaceutical formulation includes a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms* and Drug Delivery Systems, Seventh Ed. (Lippincott Williams & Wilkins 1999).

In some instances, the pharmaceutical formulation further includes pH adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some instances, the pharmaceutical formulation further includes diluent which are used to stabilize compounds because they provide a more stable environment. Salts dissolved in buffered solutions (which also provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-PacR (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In some cases, the pharmaceutical formulation includes disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema P100, Emcocel®, Vivacel®, Ming Tia®, and Solka-Flock®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulation includes filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol has a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Therapeutic Regimens

In some embodiments, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, once in two months, once in three months, once in four months, once in five months, once in six months or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some embodiments, one or more pharmaceutical compositions are administered simultaneously, sequentially, or at an interval period of time. In some embodiments, one or more pharmaceutical compositions are administered simultaneously. In some cases, one or more pharmaceutical compositions are administered sequentially. In additional cases, one or more pharmaceutical compositions are administered at an interval period of time (e.g., the first administration of a first pharmaceutical composition is on day one followed by an interval of at least 1, 2, 3, 4, 5, or more days prior to the administration of at least a second pharmaceutical composition).

In some embodiments, two or more different pharmaceutical compositions are co-administered. In some instances, the two or more different pharmaceutical compositions are co-administered simultaneously. In some cases, the two or more different pharmaceutical compositions are co-administered sequentially without a gap of time between administrations. In other cases, the two or more different pharmaceutical compositions are co-administered sequentially with a gap of about 0.5 hour, 1 hour, 2 hours, 3 hours, 12 hours, 1 day, 2 days, or more between administrations.

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages is altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more of the compositions and methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include target nucleic acid molecule described herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded, or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. The term "about" also includes the exact amount. Hence "about 5 μL" means "about 5 μL" and also "5 μL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g., constant or intermittent) of a health care worker (e.g. a doctor, a registered nurse, a nurse practitioner, a physician's assistant, an orderly or a hospice worker).

The term "therapeutically effective amount" relates to an amount of a polynucleic acid molecule conjugate that is sufficient to provide a desired therapeutic effect in a mammalian subject. In some cases, the amount is single or multiple dose administration to a patient (such as a human) for treating, preventing, preventing the onset of, curing, delaying, reducing the severity of, ameliorating at least one symptom of a disorder or recurring disorder, or prolonging the survival of the patient beyond that expected in the absence of such treatment. Naturally, dosage levels of the particular polynucleic acid molecule conjugate employed to provide a therapeutically effective amount vary in dependence of the type of injury, the age, the weight, the gender, the medical condition of the subject, the severity of the condition, the route of administration, and the particular inhibitor employed. In some instances, therapeutically effective amounts of polynucleic acid molecule conjugate, as described herein, is estimated initially from cell culture and animal models. For example, $IC_{50}$ values determined in cell culture methods optionally serve as a starting point in animal models, while $IC_{50}$ values determined in animal models are optionally used to find a therapeutically effective dose in humans.

Skeletal muscle, or voluntary muscle, is generally anchored by tendons to bone and is generally used to effect skeletal movement such as locomotion or in maintaining posture. Although some control of skeletal muscle is generally maintained as an unconscious reflex (e.g., postural muscles or the diaphragm), skeletal muscles react to conscious control. Smooth muscle, or involuntary muscle, is found within the walls of organs and structures such as the esophagus, stomach, intestines, uterus, urethra, and blood vessels.

Skeletal muscle is further divided into two broad types: Type I (or "slow twitch") and Type II (or "fast twitch"). Type I muscle fibers are dense with capillaries and are rich in mitochondria and myoglobin, which gives Type I muscle tissue a characteristic red color. In some cases, Type I muscle fibers carries more oxygen and sustain aerobic activity using fats or carbohydrates for fuel. Type I muscle fibers contract for long periods of time but with little force. Type II muscle fibers are further subdivided into three major subtypes (IIa, IIx, and IIb) that vary in both contractile speed and force generated. Type II muscle fibers contract quickly and powerfully but fatigue very rapidly, and therefore produce only short, anaerobic bursts of activity before muscle contraction becomes painful.

Unlike skeletal muscle, smooth muscle is not under conscious control.

Cardiac muscle is also an involuntary muscle but more closely resembles skeletal muscle in structure and is found only in the heart. Cardiac and skeletal muscles are striated in that they contain sarcomeres that are packed into highly regular arrangements of bundles. By contrast, the myofibrils of smooth muscle cells are not arranged in sarcomeres and therefore are not striated.

Muscle cells encompass any cells that contribute to muscle tissue. Exemplary muscle cells include myoblasts, satellite cells, myotubes, and myofibril tissues.

As used here, muscle force is proportional to the cross-sectional area (CSA), and muscle velocity is proportional to muscle fiber length. Thus, comparing the cross-sectional areas and muscle fibers between various kinds of muscles is capable of providing an indication of muscle atrophy. Various methods are known in the art to measure muscle strength and muscle weight, see, for example, "Musculoskeletal assessment: Joint range of motion and manual muscle strength" by Hazel M. Clarkson, published by Lippincott Williams & Wilkins, 2000. The production of tomographic images from selected muscle tissues by computed axial tomography and sonographic evaluation are additional methods of measuring muscle mass.

Examples

These examples are provided for illustrative purposes only and not to limit the scope of the claims provided herein.

Example 1. Antibody siRNA Conjugate

DMPK-AOC is an antibody-siRNA conjugate drug product formed by the conjugation of a human transferrin receptor 1 targeting humanized IgG1 antibody (anti-human transferrin receptor antibody) and one double stranded siRNA oligonucleotide (DMPK siRNA) targeting DMPK mRNA (FIG. 1). The SMCC maleimide linker is located on 5' end the passenger strand and it is conjugated to the antibody through one of the cysteines in the antibody amino acid sequence. The conjugate binds human transferrin receptor on the cell surface, internalizes into the cell and delivers the siRNA oligonucleotide to the intracellular compartment. Upon uptake by the cells, the siRNA loads into the RISC and hydrolyses the target pathogenic DMPK mRNA.

The anti-human transferrin receptor antibody and DMPK siRNA used in the creation of DMPK-AOC are produced using well established manufacturing processes by commercial, GMP compliant Contract Development and Manufacturing Organizations (CDMOs). Anti-human transferrin receptor antibody is produced using recombinant protein expression technology in CHO cells, and DMPK siRNA is produced using standard phosphoramidite solid phase synthetic chemistry. As used herein, DMPK siRNA is a double stranded siRNA oligonucleotide targeting DMPK mRNA that is also conjugated with the SMCC linker attached to the 5' end of the passenger strand. Each of these is fully characterized and formally released. DMPK-AOC is produced using a standard random cysteine bioconjugation reaction of the anti-human transferrin receptor antibody with the maleimide of DMPK siRNA followed by anion exchange chromatography purification to isolate bulk conjugate which is then converted into the finished DMPK-AOC. Finished DMPK-AOC is then formally released using standard methodology for protein therapeutics. Upon completion of manufacture, testing and release, each of the antibody and DMPK siRNA are bioconjugated together to form the drug substance.

Example 2. Manufacture of Antibody AV01mAb

Cell Bank-A stable research cell bank (RCB) of the stable cell line was constructed by using CHOK1SV host working cells and was confirmed to be free from contamination by mycoplasmas, bacteria, molds, and yeasts. A 200 vial master cell bank (MCB) has been prepared using a vial of the research cell bank.

Antibody Production from Master Cell Bank-Cells from an ampoule of the master cell bank were progressively increased in volume using protein-free medium prior to inoculation into the production bioreactor. Downstream Processing-Upon completion of the cell culture, cells, and cell debris were removed by filtration of the culture.

Example 3. Structural Characterization of Anti-Human Transferrin Receptor Antibody Structure—An amino acid sequence for both heavy and light chains has been determined from the translation of the nucleotide sequence of anti-human transferrin receptor antibody.

Heavy Chain Sequence of the anti-human transferrin receptor antibody - SEQ ID NO: 48

QVQLVQSGAEVKKPGASVKVSCKASGYTFTNYWMHWVRQAPGQGLEWIG

EINPINGRSNYAEKFQGRVTLTVDTSSSTAYMELSRLRSDDTAVYYCAR

GTRAMHYWGQGTLVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKRVEPKSCDKTHTCPPCPAPEAAGGPSVFLFPPK

PKDTLMISRTPEVTCVVVDVSHEDPEVKFNWYVDGVEVHNAKTKPREEQ

YNSTYRVVSVLTVLHQDWLNGKEYKCKVSNKARPAPIEKTISKAKGQPR

EPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLS

LSPG

Light Chain Sequence of the anti-human transferrin receptor antibody - SEQ ID NO: 63

DIQMTQSPSSLSASVGDRVTITCRTSENIYNNLAWYQQKPGKSPKLLIY

AATNLADGVPSRFSGSGSGTDYTLTISSLQPEDFATYYCQHFWGTPLTF

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Example 4: DMPK siRNA

DMPK siRNA is a synthetic duplex oligonucleotide that contains a 19-mer passenger strand and a complementary 21-mer guide strand with a two-nucleotide overhang at the 3'end of the guide strand. A C6-SMCC linker {4-(N-maleimidomethyl)cyclohexane-1-carboxyamide} is attached at the 5'end of the passenger strand to enable conjugation to the Antibody Intermediate. The nucleotide sequence and internucleotide linkages are shown in Table 11.

TABLE 11

| | |
|---|---|
| Molecule Sequence | Sense: 5' SMCC-AmC6-mC-(s)-mC-(s)-mC-mU-mA-mG-fA-fA-fC-mU-mG-mU-mC-mU-mU-mC-mG-(s)-mA-(s)-mA 3' (SEQ ID NO: 114)<br>Antisense: 5' mU-(s)-fU-(s)-mC-mG-mA-fA-mG-mA-mC-mA-mG-mU-mU-fC-mU-fA-mG-mG-mG-(s)-mU-(s)-mU 3' (SEQ ID NO: 115)<br>Where SMCC = 4-(N-maleimidomethyl) cyclohexane -1-amidate<br>AmC6 = 6-Amino-1-hexanol linker<br>mX = 2'-O-methyl ribonucleoside<br>fX = 2'-fluoro nucleoside<br>-(s)- = phosphorothioate internucleotide linkage<br>- = phosphodiester internucleotide linkages |
| Backbone | Mixture of Phosphodiester (PO) and Phosphorothioate (PS) |

Single strands of RNA (guide and passenger strands) are each produced individually via solid-phase synthesis, using well established phosphoramidite solid phase synthesis methods. The purified and lyophilized single strands are then duplexed at equimolar ratios to generate double-stranded siRNA. SMCC linker is conjugated to the primary amine conjugation handle on the 5'end of the sense strand of siRNA using standard N-hydroxy succinimide chemistry. Excess unreacted SMCC linker is removed using UF/DF step and the resultant SMCC-siRNA is released.

Example 5: Antibody Selection

Figure 3:
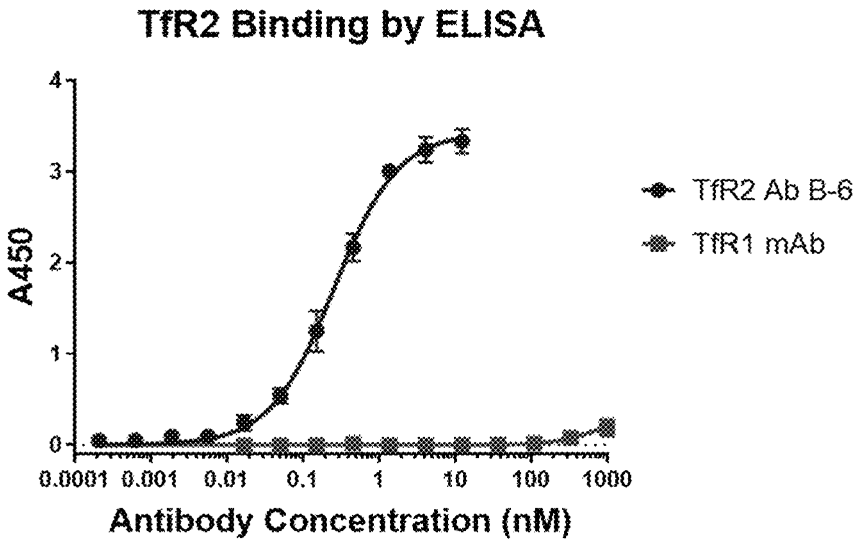
FIG. 3 illustrates a graph of TfR2 binding of anti-TfR antibodies by ELISA.
Figure 4:
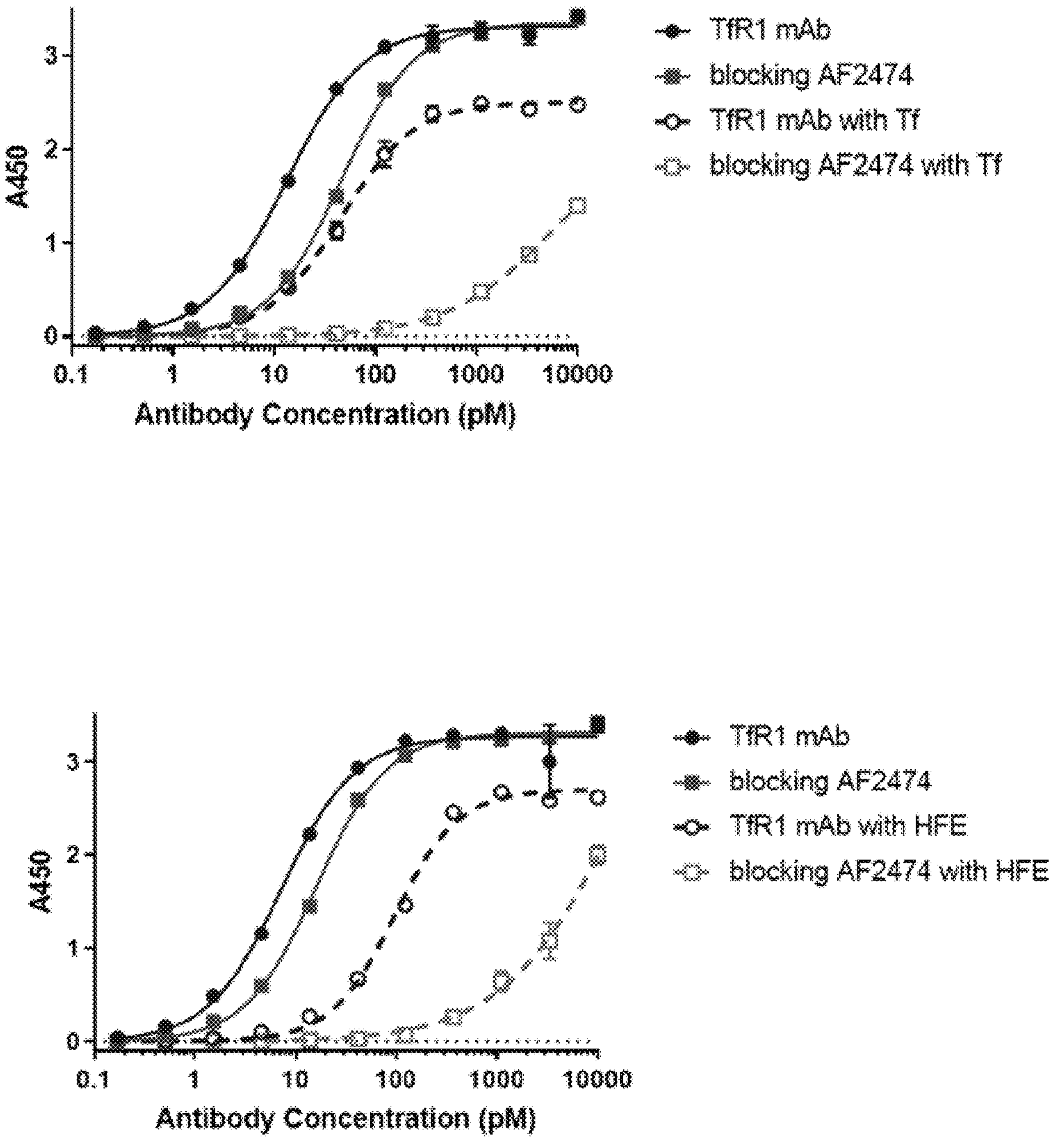
FIG. 4 illustrates graphs of anti-TfR antibodies' binding to TfR1 upon presence of cofactors.

Antibody Selection Criteria: Several anti-human transferrin receptor 1 (TfR1) antibodies were tested by ELISA and found to bind the receptor with high affinity. These antibodies were also tested for binding to cynomolgus monkey TfR 1 to ensure species cross-reactivity. A mouse IgG2a monoclonal antibody (mAb) that binds both human and cynomolgus monkey TfR1 was assessed for specificity by demonstrating a lack of binding to the closely related transferrin receptor 2 (TfR2) by ELISA (FIG. 3). Commercially Available Anti-TfR2 Antibody B-6 Displays Clear Binding to TfR2 by ELISA, While Mouse Anti-human TfR1 mAb Does Not Bind TfR2 at Concentrations Up to 10 μM. The mouse anti-human TfR1 mAb was also assessed for binding in the presence of TfR1-binding ligands transferrin (Tf) and homeostatic iron regulator (HFE), with the TfR1 mAb maintaining strong binding to TfR1 even in the presence of TfR1 ligands (FIG. 4). As shown in FIG. 4, antibodies were bound to TfR1 directly or TfR1 pre-bound to cofactors transferrin (Tf) or HFE. AF2474 is a commercially available antibody known to bind to the same TfR1 epitope as transferrin or HFE. The mouse anti-human TfR1 mAb shows some loss of binding between direct interaction with TfR 1 compared to the cofactor complex, but the change in affinity is minimal in comparison to AF2474. Importantly, competition of the TfR1 mAb with the natural ligands for TfR1 is expected to be toxic due to the potential for blockade of iron import into cells; therefore, the identified TfR1 mAb needed to bind to an epitope on TfR1 that would minimize competition with the natural ligands. Given that it met all of these selection criteria, the mouse IgG2a anti-human TfR1 mAb was moved into a humanization program to develop an antibody suitable for clinical development.

Example 6: In vivo Activity

Figure 5:
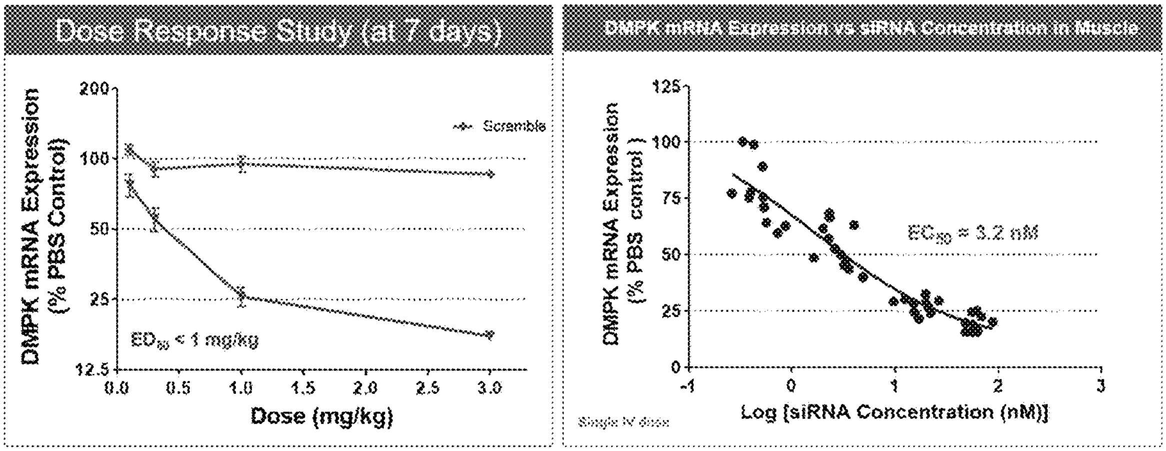
FIG. 5 illustrates graphs of in vivo dose response of AOC-mediated DMPK knockdown in mouse skeletal muscles.

DMPK-AOCs were utilized for in vivo studies in mice. In vivo studies of AOCs in mice utilized a surrogate anti-TfR1 antibody that binds to mouse TfR1 as the lead human antibody AV01Ab does not cross-react with mouse TfR1 (only human and monkey). Mouse cross-reactive siDMPK.36 was conjugated to anti-mouse TfR 1 mAb and the conjugates were administered into wild-type female CD-1 mice (n=4 per group) via IV injection, with tissues harvested and DMPK mRNA knockdown assessed 7 days post-dose. The AOCs were administered as a dose response of 3, 1, 0.3, and 0.1 mg/kg (based on the weight of the siRNA), resulting in 80% reduction in DMPK expression in skeletal muscles with the 3 mg/kg dose (FIG. 5). The DMPK-AOC showed robust activity with an ED50<1 mg/kg and EC50 of approximately 3 nM. The negative control scrambled sequence siRNA showed no DMPK mRNA knockdown, demonstrating the specificity of the DMPK-AOC activity.

Figure 6:
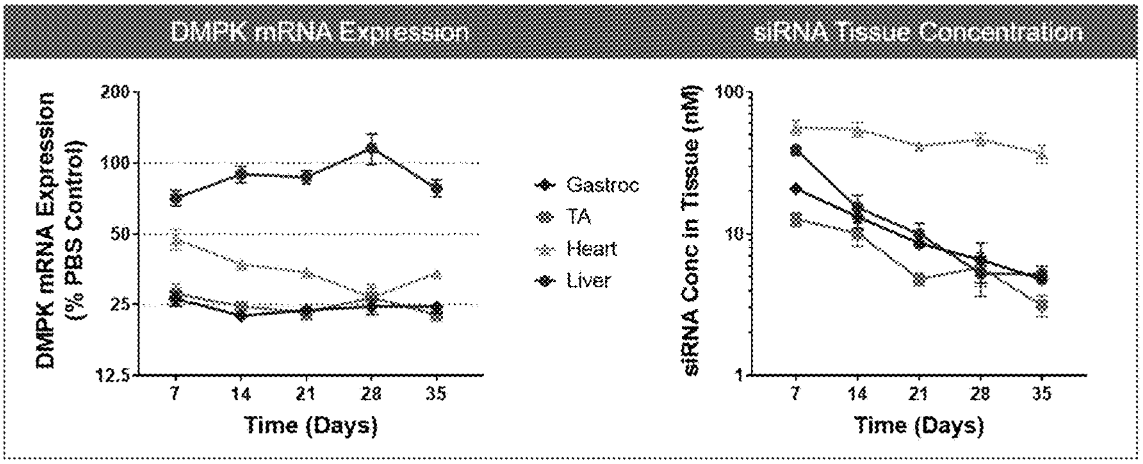
FIG. 6 illustrates graphs of time course of AOC-mediated DMPK knockdown in mouse tissues (left) and concentration of siDMPK.36 in mouse tissues over time (Right).

Mouse cross-reactive DMPK-AOC was conjugated to anti-mouse TfR1 mAb and the conjugate was administered into wild-type female CD-1 mice (n=4 per group) via IV injection at 3 mg/kg (based on siRNA weight). Tissues were harvested and DMPK mRNA knockdown was assessed every week out to 5 weeks post-dose (FIG. 6). From 7-35 d post-dose maximal DMPK knockdown (approximately 75%) was achieved in skeletal muscles. Slightly less DMPK knockdown was achieved in heart (approximately 65%), while no knockdown was observed in liver despite the presence of DMPK siRNA in liver. The long duration of activity following a single AOC dose should enable infrequent dosing in patients.

Figure 7:
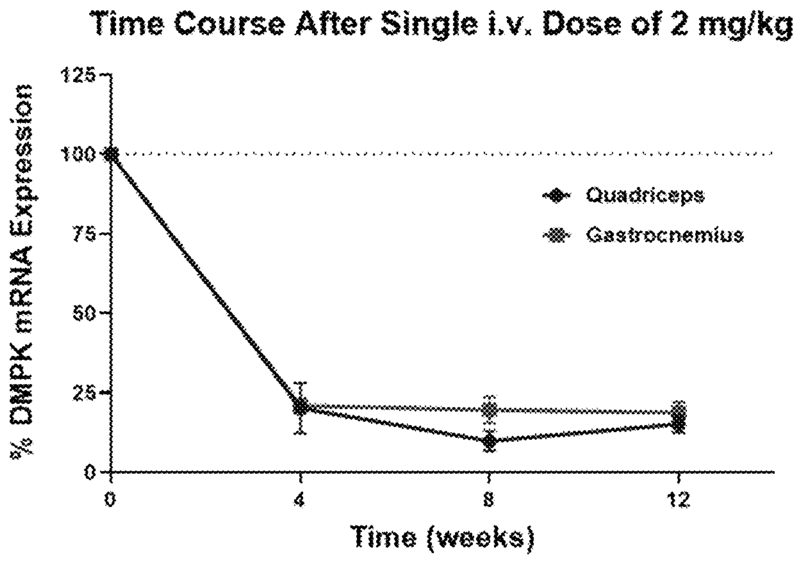
FIG. 7 illustrates a graph showing AOC-mediated DMPK knockdown in Cynomolgus Monkey Skeletal muscles over a time course out to 12 weeks post-dose.

In vivo Pharmacology Data in Non-Human Primates: DMPK-AOC was administered into wild-type male Cynomolgus monkeys (n=3 per group) via IV infusion over 30 minutes, followed by tissue collection for a period of 12 weeks post-dose. Skeletal muscles were surgically biopsied under anesthesia with Ketamine/Xylazine. Following final blood and muscle biopsy collection 12 weeks post-dose, sedated animals were euthanized by an overdose of euthanasia solution. Terminal tissue punch biopsies of multiple additional tissues were then collected. Following a single IV dose of AOC at 2 mg/kg (based on siRNA weight), the 75% reduction in DMPK expression was durable and sustained out to 12 weeks post-dose (FIG. 7).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A conjugate comprising (i) an anti-transferrin receptor antibody or antigen binding fragment thereof, (ii) an siRNA molecule, which comprises a guide strand and a passenger strand, and (iii) a linker;

wherein the anti-transferrin receptor antibody or antigen binding fragment thereof comprises a variable heavy chain (VH) region, which comprises an HCDR1 comprising the sequence of SEQ ID NO: 17; an HCDR2 comprising the sequence of SEQ ID NO: 20; and an HCDR3 comprising the sequence of SEQ ID NO: 19;

wherein the anti-transferrin receptor antibody or antigen binding fragment thereof comprises a variable light chain (VL) region, which comprises a LCDR1 comprising the sequence of SEQ ID NO: 22; a LCDR2 comprising the sequence of SEQ ID NO: 23; and a LCDR3 comprising the sequence of SEQ ID NO: 24; and wherein the passenger strand of the siRNA comprises the sequence of SEQ ID NO: 3 and the guide strand of the siRNA comprises the sequence of SEQ ID NO: 4; and wherein the linker comprises a maleimide group that conjugates the anti-transferrin receptor antibody or antigen binding fragment thereof to a terminus of the guide strand or the passenger strand.

2. The conjugate of claim 1, wherein the maleimide group is succinimidyl 4-(N-maleimidomethyl)cyclohexane-1-carboxylate (SMCC).

3. The conjugate of claim 1, wherein the linker conjugates the anti-transferrin receptor antibody or antigen binding fragment thereof to a 5' end terminus of the passenger strand.

4. The conjugate of claim 1, wherein the anti-transferrin receptor antibody or antigen binding fragment thereof is a full-length anti-transferrin receptor antibody.

5. The conjugate of claim 4, wherein the full-length anti-transferrin receptor antibody is a humanized anti-transferrin receptor antibody or a human anti-transferrin receptor antibody.

6. The conjugate of claim 4, wherein the full-length anti-transferrin receptor antibody further comprises a mutation in the heavy chain constant region selected from the group consisting of L233A, and L234A.

7. The conjugate of claim 4, wherein the full-length anti-transferrin receptor antibody further comprises mutations of L233A, and L234A,.

8. The conjugate of claim 1, wherein the anti-transferrin receptor antibody or antigen binding fragment thereof is selected from the group consisting of monovalent Fab', divalent Fab2, and single chain variable fragment (scFv).

9. A conjugate comprising (i) an anti-transferrin receptor antibody or antigen binding fragment thereof, (ii) an siRNA, which comprises a guide strand and a passenger strand, and (iii) a linker;

wherein the anti-transferrin receptor antibody or antigen binding fragment thereof comprises the variable heavy chain (VH) sequence of SEQ ID NO: 30 and the variable light chain (VL) sequence of SEQ ID NO: 34;

wherein the passenger strand of the siRNA comprises the sequence of SEQ ID NO: 3 and the guide strand of the siRNA comprises the sequence of SEQ ID NO: 4; and wherein the linker comprises a maleimide group that conjugates the anti-transferrin receptor antibody or antigen binding fragment thereof to a terminus of the guide strand or the passenger strand.

10. The conjugate of claim 9, wherein the maleimide group is succinimidyl 4-(N-maleimidomethyl)cyclohexane-1-carboxylate (SMCC).

11. The conjugate of claim 9, wherein the linker conjugates the anti-transferrin receptor antibody or antigen binding fragment thereof to a 5' end of the passenger strand.

12. The conjugate of claim 9, wherein the anti-transferrin receptor antibody or antigen binding fragment thereof is a full-length anti-transferrin receptor antibody.

13. The conjugate of claim 12, wherein the full-length anti-transferrin receptor antibody is a humanized anti-transferrin receptor antibody or a human anti-transferrin receptor antibody.

14. The conjugate of claim 12, wherein the full-length anti-transferrin receptor antibody further comprises a mutation in the heavy chain constant region selected from the group consisting of L233A, and L234A.

15. The conjugate of claim 12, wherein the full-length anti-transferrin receptor antibody further comprises the L233A, and L234A mutations in the heavy chain constant region.

16. The conjugate of claim 9, wherein the anti-transferrin receptor antibody or antigen binding fragment thereof is selected from the group consisting of monovalent Fab', divalent Fab2, and single chain variable fragment (scFv).

17. A conjugate comprising (i) an anti-transferrin receptor antibody, (ii) an siRNA molecule, which comprises a guide strand and a passenger strand, and (iii) a linker;

wherein the anti-transferrin receptor antibody comprises two heavy chains, each of which comprises SEQ ID NO:48, and two light chains, each of which comprises SEQ ID NO:63;

wherein the passenger strand of the siRNA comprises the sequence of SEQ ID NO: 3 and the guide strand of the siRNA comprises the sequence of SEQ ID NO: 4; and wherein the linker comprises a maleimide group that conjugates the anti-transferrin receptor antibody to a 5' end terminus of the passenger strand of the siRNA.

18. The conjugate of claim 17, wherein the maleimide group is succinimidyl 4-(N-maleimidomethyl)cyclohexane-1-carboxylate (SMCC).

* * * * *